US007026515B2

(12) United States Patent
Tsunoda et al.

(10) Patent No.: US 7,026,515 B2
(45) Date of Patent: Apr. 11, 2006

(54) OPTICALLY ACTIVE AMINE DERIVATIVES AND PREPARATION PROCESS THEREFOR

(75) Inventors: Hidetoshi Tsunoda, Mobara (JP); Kunio Okumura, Sodegaura (JP); Kengo Otsuka, Mobara (JP)

(73) Assignee: Mitsui Chemicals, Inc., Tokyo (JP)

( * ) Notice: Subject to any disclaimer, the term of this patent is extended or adjusted under 35 U.S.C. 154(b) by 143 days.

(21) Appl. No.: 10/416,185

(22) PCT Filed: Nov. 9, 2001

(86) PCT No.: PCT/JP01/09830

§ 371 (c)(1),
(2), (4) Date: May 9, 2003

(87) PCT Pub. No.: WO02/38532

PCT Pub. Date: May 16, 2002

(65) Prior Publication Data

US 2004/0030144 A1 Feb. 12, 2004

(51) Int. Cl.

*C07C 215/30* (2006.01)
*C07C 215/46* (2006.01)
*C07C 213/02* (2006.01)
*C07C 213/08* (2006.01)
*C07C 271/16* (2006.01)

(52) U.S. Cl. ...................... 564/487; 564/413; 564/502; 564/503; 560/24; 560/27; 560/30; 560/32; 560/157; 560/159; 548/228; 548/492; 548/503

(58) Field of Classification Search ................ 548/215
See application file for complete search history.

(56) References Cited

U.S. PATENT DOCUMENTS

| | | | | |
|---|---|---|---|---|
| 5,116,858 A | | 5/1992 | Hayashi et al. | |
| 5,449,694 A | * | 9/1995 | Yamazaki et al. | 514/653 |
| 6,770,642 B1 | * | 8/2004 | Cole et al. | 514/233.2 |

FOREIGN PATENT DOCUMENTS

| | | |
|---|---|---|
| CN | 1087079 A | 5/1994 |
| EP | 77983 A1 | 5/1983 |
| EP | 396973 A1 | 11/1990 |
| EP | 603414 A1 | 6/1994 |
| JP | 62-29998 | 12/1987 |
| WO | WO 95/09155 | 4/1995 |
| WO | WO 99/32483 A1 | 7/1999 |

OTHER PUBLICATIONS

Database CAPLUS on STN, Acc. No. 1982:115500, Glennon et al., Journal of Medicinal Chemistry (1982), 25(4), p. 393-7 (abstract).*

Draper, Richard W. et al., Novel Stereoselective Syntheses of the Fused Benzazepine Dopamine D1 Antagonist (6aS, 13bR)-11-Chloro-6, 6a, 7, 8, 9, 13b-hexahydro-7-methyl-5H-benzo [d] naphth [2, 1-b] azepin-12-ol: 2. L-Homophenylalanine-Based Syntheses, Org. Process Res. Dev., 1998, vol. 2. No. 3, pp. 186-193.

(Continued)

*Primary Examiner*—Brian Davis
(74) *Attorney, Agent, or Firm*—Buchanan Ingersoll PC

(57) ABSTRACT

A readily available and inexpensive natural α-amino acid is converted into a compound represented by formula (1), which is then reacted with an organometallic reagent represented by formula (2) to give an optically active 5-hydroxyoxazolidine represented by formula (3), which is then treated with an acid to provide an optically active aminoketone represented by formula (4). The product is then converted into an optically active aminoalcohol represented by formula (5) or (6) by, for example reduction.

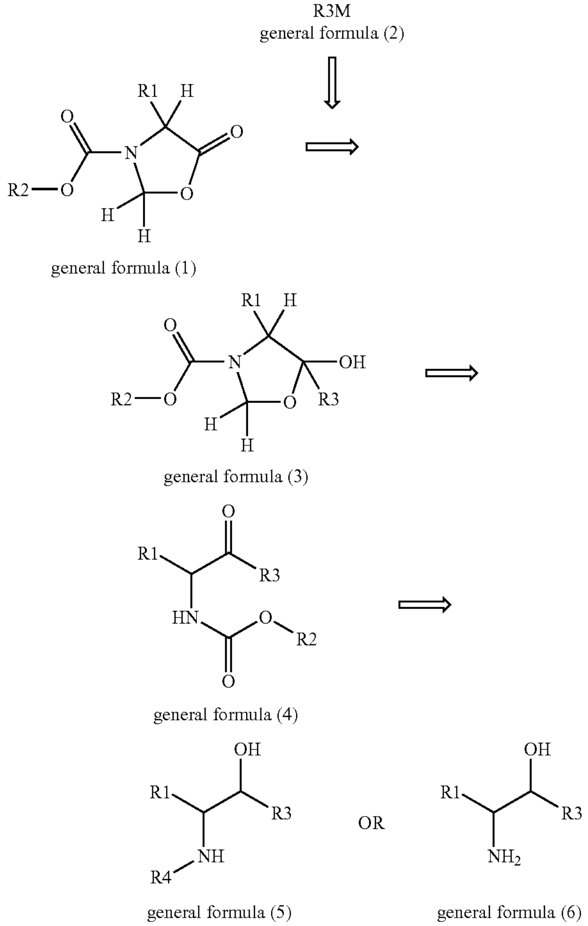

17 Claims, No Drawings

OTHER PUBLICATIONS

Howard E. Smith et al., "Agonist Effects of β-Phenethylamines on the Noradrenergic Cyclic Adenosine 3' ,5'-Monophosphate Generating System in Rat Limbic Forebrain. Stereoisomers of *p*-Hydroxynorephedrine", Journal of Medicinal Chemistry (1977) vol. 20, No. 7, pp. 978-981.

A. Miyashita et al., "Synthesis of 2,2'-Bis(diphenylphosphino)-1, 1'-binaphthyl (BINAP), an Atropisomeric Chiral Bis(triaryl)phosphine, and Its Use in the Rhodium(l)-Catalyzed Asymmetric Hydrogenation of α-(Acylamino)acrylic Acids", J. Am. Chem. Soc. (1980) vol. 102, pp. 7932-7934.

Magnus W. Walter et al., "Reaction of (Trifluoromethyl) trimethylsilane With Oxazolidin-5-ones: Synthesis of Peptidic and Nonpeptidic Trifluoromethyl Ketones", J. Org. Chem. (1998) vol. 63, pp. 5179-5192.

Thomas F. Buckley III et al. "α-Amino Acids as Chiral Educts for Asymmetric Products. Amino Acylation with *N*-Acylamino Acids", J. Am. Chem. Soc. (1981) vol. 103 pp. 6157-6163.

* cited by examiner

OPTICALLY ACTIVE AMINE DERIVATIVES AND PREPARATION PROCESS THEREFOR

BACKGROUND OF THE INVENTION

1. Field of the Invention

This invention relates to a process for preparing an optically active aminoalcohol derivative useful as a production intermediate for medicines, agricultural agents and so forth; for example, a process for preparing erythro-(1R,2S)-p-hydroxynorephedrine. This invention also relates to an optically active 5-hydroxyoxazolidine derivative as an important intermediate for production of the above optically active aminoalcohol derivative or a number of other optically active amine derivatives as well as a preparing process therefor. For example, an optically active 5-hydroxyoxazolidine derivative according to this invention is also very useful as a production intermediate for an azole antibacterial agent. A compound defined by general formula (1), (3) or (4) which has an asymmetric carbon having $R^1$ and an amino substituent represents a R— or S-form, but not a racemic mixture of the R and S forms. A compound defined by general formula (5) or (6) having two adjacent asymmetric carbons which have an amino and hydroxy substituents represents a R—S or S—R form, but not an R—R or S—S form.

2. Description of the Prior Art

Recently, optically active compounds have been increasingly needed in many applications including medicines and agricultural agents. For industrial applications, there has been strongly needed for a convenient and inexpensive process for preparing an optically active material.

The following three processes are those according to the prior art for preparing an optically active aminoalcohol derivative relating to this invention:

[1] A method, in which, after a racemic compound of the desired compound is chemically synthesized, it is then optically resolved via, for example, a diastereomer salt to give the desired optically active compound. [2] A method, in which a technique for chemical or biological asymmetric synthesis is employed to give an optically active compound from an optically inactive material.

[3] A method by a so-called "chiral pool method", in which it starts from an optically active material and the optical active compound is obtained under prevention of racemization.

Regarding the process in [1] as "A method, in which, after a racemic compound of the desired compound is chemically synthesized, it is then optically resolved via, for example, a diastereomer salt to give the desired optically active compound", an example may be a process according to the prior art for preparing erythro-(1R,2S)-p-hydroxynorephedrine within a category of desired optically active aminoalcohol derivatives in this invention, in which after a racemate having the desired structure is first chemically synthesized, its optical resolution is carried out using an optically active carboxylic acid such as D-tartaric acid (J. Med. Chem., 1977, 20, 7, 978).

However, as long as using a preparation process on the basis of optical resolution, it is theoretically impossible to increase the yield over 50%, unless an enantiomer is recovered and subject to a special treatment such as racemization. Furthermore, an optically active carboxylic acid and the other compounds required in resolution are generally expensive, and it is often necessary to repeat several times a process such as recrystallization. In other words, the optical resolution process requires an expensive resolving agent(s) and a multiple-stage operation, and is, therefore, industrially a high-cost preparation process.

The process in [2] as "A method, in which a technique for chemical or biological asymmetric synthesis is employed to give an optically active compound from an optically inactive material" has been significantly advanced. As examples, there are mentioned an asymmetric synthesis technique based on a chemical synthesis including the uses of asymmetric reduction catalysts or the other agents (J. Am. Chem. Soc., 1980, 102, 7932) and an asymmetric synthesis technique based on a biotechnological synthesis using an enzyme or the other agents (Japanese Patent Laid-open No. 62-29998). Unfortunately, specificity for each substrate is significantly involved in practical production and thus the process cannot be applied to all kinds of production. Furthermore, the process cannot be always inexpensive when requiring an expensive asymmetric catalyst. In practice, for an optically active aminoalcohol derivative as a desired compound in this invention, there has been available no industrially reasonable preparation processes on the basis of chemical or biotechnological technique as described above.

For the process in [3] as "A method by a so-called "chiral pool method", in which it starts from an optically active material and the optical active compound is obtained under prevention of racemization", there have been many problems to be solved; for example, control of racemization is difficult till now and furthermore, practical production requires multiple steps. Regarding the aminoalcohol derivatives as the desired compounds in the present invention, no processes have been reported till now, which is fully satisfactory in the industrial viewpoint.

Regarding the prior art techniques for production of the optically active aminoalcohol derivatives, only the processes, which are difficult in the industrial viewpoint and require considerably high cost. Therefore, a novel, inexpensive and more convenient processes for the production are strongly desired.

Furthermore, only the following processes [4] to [6] are known in the prior art for preparation of an optically active 5-hydroxyoxazolidine derivative as an important production intermediate in the process of this invention:

[4] A method, in which (4S)-N-(ethoxycarbonyl)-4-(2-phenylethyl)-5-oxazolidinone is reacted with 4-chloro-3-methoxyphenyl magnesium bromide (WO 95/09155).

[5] A method, in which a 5-oxazolidinone derivative is reacted with a halomethyl lithium (WO 00/53571).

[6] A method, in which a 5-oxazolidinone derivative is reacted with (trifluoromethyl)trimethylsilane (J. Org. Chem. 1998, 63 (15), 5179).

In the above [4], the compound as a starting material is a special synthetic, non-naturally, compound relating to amino-acids, which has a phenylethyl group in its side chain. The compound is, therefore, prepared by a multistep reaction and it is difficult to obtain the compound in general. In addition, it is not an inexpensive material in the viewpoint of its production cost and the process maintains a significant problem in raw material supply. Furthermore, in the above process [4], the process is extremely limited, as a single production example, to that of the compound having a 4-chloro-3-methoxyphenyl group at 5-position in the oxazolidinone ring as a principal structure, and the product is used only as a starting material for a limited application to produce a medicine (Sch39166). It cannot be said that the preparation process as an example described in [4] is a universal process, and that, regarding an optically active 5-hydroxyoxazolidine derivative, which is widely useful, its preparation process has been fully established.

Regarding the compounds described in above [5] or [6], a special functional group such as a haloalkyl group (for example, a chloromethyl group) and a trifluoromethyl group is reacted at the 5-position of the oxazolidine as a main structure, but neither aryl nor hetero ring, which are widely useful for an intermediate of a medicine and agricultural agent are not included.

Although an optically active aminoalcohol derivative having an aryl group or heterocycle has been increasingly demanded in many applications such as in the pharmaceutical and agricultural fields, no general production methods has been found in the prior art, regarding the optically active 5-hydroxyoxazolidine derivative having an aryl group or heterocycle at the 5-position as its important production intermediate.

As a known prior art for preparation of an optically active aminoketone relating to this invention, a process is known, which uses a reaction where a carboxyl group in an N-protected amino acid is converted into an acid chloride, which then undergoes Friedel-Crafts reaction (J. Am. Chem. Soc. 1981, 103, 6157). Acylation using Friedel-Crafts reaction is, however, not considered to be a general preparation method for the reasons that the reaction causes racemization, that the reaction is considerably restricted by a structure to be acylated and that sometimes an aminoketone produced cannot be isolated. Thus, an industrially practical process is needed.

SUMMARY OF THE INVENTION

An objective of this invention is to provide a stereoselective process for preparing an optically active aminoalcohol derivative represented by the general formula (5), which is useful as a production intermediate for a medicine or agricultural agent using a "readily available and inexpensive natural α-amino acid" as a starting material without racemization. Another objective is to provide technique to prepare the compound stably in a large scale with an adequate optical purity and a lower cost in an industrial viewpoint. Another objective is to provide a novel optically active 5-hydroxyoxazolidine derivative represented by general formula (3) and a novel aminoketone derivative represented by general formula (4) as important intermediates for production of the above optically active aminoalcohol derivative or many optically active amine derivatives other than the above compound as well as a novel preparation process therefor.

After intensive investigation to achieve the above objects, the present inventors have found a process for preparing an optically active aminoalcohol derivative represented by general formula (5), as a very important production intermediate for a medicine or agricultural agent, from an inexpensive and easily available starting material. Specifically, the present inventors have newly found a process for preparing the compound stereoselectively by a short process while preventing racemization, using a "natural α-L-amino acid which is industrially available with a lower cost in a large amount" and a "natural α-D-amino acid which is industrially available with a lower cost in a large amount by racemization and optical resolution of a natural α-L-amino acid or selective assimilation (Japanese Patent Laid-open No. 63-198997) as starting materials.

In other words, the present inventors have found an industrially very useful novel preparation process for an optically active aminoalcohol derivative, which is produced stably even in a large scale production, as well as with a higher optical purity and at a lower cost.

Furthermore, the present inventors have found a novel optically active 5-hydroxyoxazolidine derivative represented by general formula (3) having an aryl group or heterocycle at the 5-position in an oxazolidine ring, which is an important intermediate for preparing the above optically active aminoalcohol derivative and a novel preparation process therefore; and a novel aminoketone derivative represented by general formula (4) and a novel preparation process therefore.

Thus, the present invention has been completed.

This invention includes the following embodiments:

(I) A process for preparing an optically active aminoalcohol derivative, wherein an optically active 5-oxazolidinone derivative represented by a general formula (1):

(1)

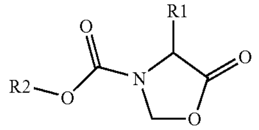

wherein $R^1$ represents an unprotected or optionally protected side chain in a natural α-amino acid; and $R^2$ represents optionally substituted alkyl, optionally substituted aryl or optionally substituted aralkyl; is reacted with an organometallic reagent represented by general formula (2):

$R^3$—M (2)

wherein $R^3$ represents optionally substituted aryl or optionally substituted heterocycle; M represents one selected from the group consisting of Li, MgX, ZnX, $TiX_3$ and CuX; and X represents halogen;

to form an optically active 5-hydroxyoxazolidine derivative represented by general formula (3):

(3)

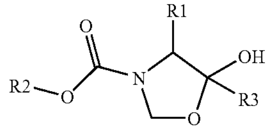

wherein $R^1$, $R^2$ and $R^3$ have the same meaning as defined above; which is then treated under acidic conditions to give an optically active aminoketone derivative represented by general formula (4):

(4)

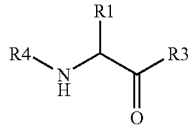

wherein $R^1$ and $R^3$ have the same meanings as defined above; and $R^4$ represents hydrogen or optionally substituted alkyloxycarbonyl, optionally substituted aryloxycarbonyl or optionally substituted aralkyloxycarbonyl as a protective group;

which is then treated with a reducing agent or catalytically hydrogenated with a metal catalyst to stereoselectively provide an optically active aminoalcohol derivative represented by general formula (5):

(5)

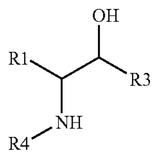

wherein $R^1$, $R^3$ and $R^4$ have the same meanings as defined above; provided that configuration of $R^1$ attached to the asymmetric carbon at 4-position and the substituent represented by a nitrogen atom in the optically active 5-oxazolidinone derivative represented by general formula (1) is not changed throughout these reactions and relative configuration between the amino group and the hydroxy group in the optically active aminoalcohol derivative represented by general formula (5) is an erythro configuration.

(II) A process for preparing an aminoalcohol derivative, wherein an optically active 5-oxazolidinone derivative represented by a general formula (1):

(1)

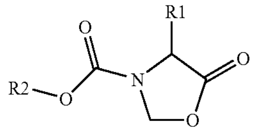

wherein $R^1$ represents an unprotected or optionally protected side chain in a natural α -amino acid; and $R^2$ represents optionally substituted alkyl, optionally substituted aryl or optionally substituted aralkyl; is reacted with an organometallic reagent represented by general formula (2):

$R^3$—M (2)

wherein $R^3$ represents optionally substituted aryl or optionally substituted heterocycle; M represents one selected from the group consisting of Li, MgX, ZnX, $TiX_3$ and CuX; and X represents halogen, to form an optically active 5-hydroxyoxazolidine represented derivative by general formula (3):

(3)

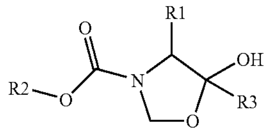

wherein $R^1$, $R^2$ and $R^3$ have the same meanings as defined above;

which is then treated under acidic conditions to give an optically active aminoketone derivative represented by general formula (4):

(4)

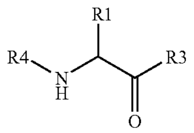

wherein $R^1$ and $R^3$ have the same meanings as defined above; and $R^4$ represents hydrogen or optionally substituted alkyloxycarbonyl, optionally substituted aryloxycarbonyl or optionally substituted aralkyloxycarbonyl as a protective group;

which is then treated with a reducing agent or catalytically hydrogenated with a metal catalyst to provide an optically active aminoalcohol derivative represented by general formula (5):

(5)

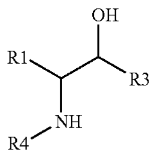

wherein $R^1$, $R^3$ and $R^4$ have the same meanings as defined above, and then, when $R^4$ is a protective group, the amino group in the product is deprotected to give an optically active aminoalcohol derivative represented by general formula (6):

(6)

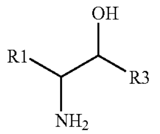

wherein $R^1$ and $R^3$ have the same meanings as defined above;

provided that configuration of $R^1$ attached to the asymmetric carbon at 4-position and the substituent represented by a nitrogen atom in the optically active 5-oxazolidinone derivative represented by general formula (1) is not changed throughout these reactions and relative configuration between the amino group and the hydroxy group in the optically active aminoalcohol derivative represented by general formula (6) is an erythro configuration.

(III) The process for preparing an optically active aminoalcohol derivative as described in (I) or (II), wherein $R^1$ represents methyl, isopropyl, isobutyl, benzyl, hydroxymethyl, benzyloxymethyl, phenylthiomethyl, methylthiomethyl, alkyloxycarbonylmethyl or alkyloxycarbonylethyl; $R^2$ represents benzyl, tert-butyl, methyl, ethyl, isopropyl or 9-fluorenylmethyl.

(IV) The process for preparing an optically active aminoalcohol as described in (I) or (II), wherein $R^3$ is represented by general formula (7):

(7)

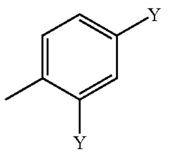

wherein Y represents halogen; or by general formula (8):

(8)

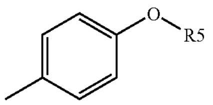

wherein $R^5$ represents hydrogen, optionally substituted alkyl, optionally substituted cycloalkyl, optionally substituted aralkyl, optionally substituted phenyl, optionally substituted heterocycle or optionally substituted heterocyclealkyl.

(V) The process for preparing an optically active aminoalcohol as described in (I) or (II) wherein $R^1$ represents methyl; and $R^3$ is represented by general formula (8).

(VI) An optically active 5-hydroxyoxazolidine derivative represented by general formula (3):

(3)

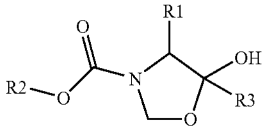

wherein $R^1$ represents an unprotected side chain or optionally protected side chain in a natural α-amino acid; $R^2$ represents optionally substituted alkyl, optionally substituted aryl or optionally substituted aralkyl; and $R^3$ represents optionally substituted aryl or optionally substituted heterocycle.

(VII) The optically active 5-hydroxyoxazolidine derivative as described in (VI), wherein $R^1$ represents methyl, isopropyl, isobutyl, benzyl, hydroxymethyl, benzyloxymethyl, phenylthiomethyl, methylthiomethyl, alkyloxycarbonylmethyl or alkyloxycarbonylethyl.

(VIII) The optically active 5-hydroxyoxazolidine derivative as described in (VI) or (VII) wherein $R^2$ represents benzyl, tert-butyl, methyl, ethyl, isopropyl or 9-fluorenylmethyl.

(IX) The optically active 5-hydroxyoxazolidine as described in (VIII) wherein $R^3$ is represented by general formula (7):

(7)

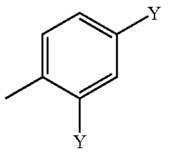

wherein Y represents halogen; or general formula (8):

(8)

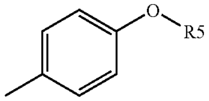

wherein $R^5$ represents hydrogen, optionally substituted alkyl, optionally substituted cycloalkyl, optionally substituted aralkyl, optionally substituted phenyl, optionally substituted heterocycle or optionally substituted heterocyclealkyl.

(X) The optically active 5-hydroxyoxazolidine as described in (IX) wherein $R^1$ is methyl.

(XI) A process for preparing an optically active 5-hydroxyoxazolidine wherein an optically active 5-oxazolidinone derivative represented by general formula (1):

(1)

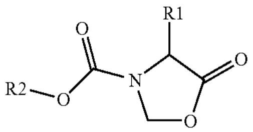

wherein $R^1$ represents an unprotected side chain or optionally protected side chain in a natural α-amino acid; $R^2$ represents optionally substituted alkyl, optionally substituted aryl or optionally substituted aralkyl;

is reacted with an organometallic reagent represented by general formula (2):

$$R^3\text{—}M \quad (2)$$

wherein $R^3$ represents optionally substituted aryl or optionally substituted heterocycle; M is one selected from the group consisting of Li, MgX, ZnX, $TiX_3$ and CuX; and X represents halogen; to provide an optically active 5-hydroxyoxazolidine derivative represented by general formula (3):

(3)

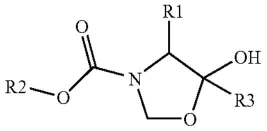

wherein $R^1$, $R^2$ and $R^3$ have the same meanings as defined above.

(XII) The process for preparing an optically active 5-hydroxyoxazolidine derivative as described in (XI) wherein $R^1$ represents methyl, isopropyl, isobutyl, benzyl, hydroxymethyl, benzyloxymethyl, phenylthiomethyl, methylthiomethyl, alkyloxycarbonylmethyl or alkyloxycarbonylethyl.

(XIII) The process for preparing an optically active 5-hydroxyoxazolidine derivative as described in (XI) or (XII) wherein $R^2$ represents benzyl, tert-butyl, methyl, ethyl, isopropyl or 9-fluorenylmethyl.

(XIV) The process for preparing an optically active 5-hydroxyoxazolidine derivative as described in (XIII) wherein $R^3$ is represented by general formula (7):

(7)

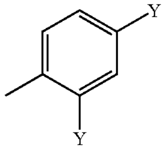

wherein Y represents halogen; or general formula (8):

(8)

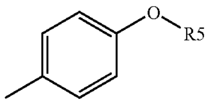

wherein $R^5$ represents hydrogen, optionally substituted alkyl, optionally substituted cycloalkyl, optionally substituted aralkyl, optionally substituted phenyl, optionally substituted heterocycle or optionally substituted heterocyclealkyl.

(XV) The process for preparing an optically active 5-hydroxyoxazolidine derivative as described in (XIV) wherein $R^1$ is methyl.

(XVI) The process for preparing an optically active 5-hydroxyoxazolidine derivative as described in (XI) or (XII) wherein M in general formula (2) is MgX wherein X is as defined above.

(XVII) An aminoketone represented by general formula (4a):

(4a)

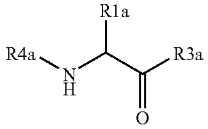

wherein $R^{1a}$ represents methyl: $R^{4a}$ represents hydrogen, benzyloxycarbonyl, tert-butoxycarbonyl or 9-fluorenylmethoxycarbonyl; $R^{3a}$ represents 4-benzyloxyphenyl, 4-methoxyphenyl, 2,4-difluorophenyl, 2,4-dichlorophenyl or 3-indolyl.

(XVIII) A process for preparing an aminoketone derivative wherein a 5-hydroxyoxazolidine derivative represented by general formula (3):

(3)

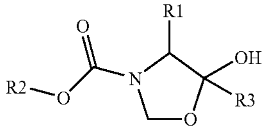

wherein $R^1$ represents an unprotected side chain or optionally protected side chain in a natural α-amino acid; $R^2$ represents optionally substituted alkyl, optionally substituted aryl or optionally substituted aralkyl; and $R^3$ represents optionally substituted aryl or optionally substituted heterocycle;

is treated under acidic conditions to form an aminoketone derivative represented by general formula (4):

(4)

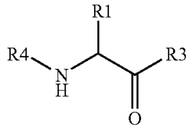

wherein $R^1$ and $R^3$ are as defined above; $R^4$ represents hydrogen or optionally substituted alkyloxycarbonyl, optionally substituted aryloxycarbonyl or optionally substituted aralkyloxycarbonyl as a protective group.

(XIX) An optically active alcohol derivative represented by general formula (5a):

(5a)

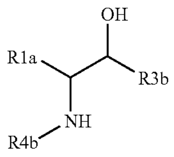

wherein $R^{1a}$ represents methyl; $R^{3b}$ represents 4-benzyloxyphenyl; $R^{4b}$ represents benzyloxycarbonyl; and configuration between the amino group and the hydroxy group is erythro.

(XX) A process for preparing an optically active aminoalcohol derivative wherein an optically active aminoketone represented by general formula (4b):

(4b)

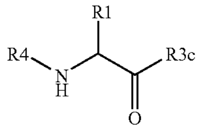

wherein $R^1$ represents an unprotected side chain or optionally protected side chain in a natural α-amino acid; $R^4$ represents hydrogen or optionally substituted alkyloxycarbonyl, optionally substituted aryloxycarbonyl or optionally substituted aralkyloxycarbonyl as a protective group; $R^{3c}$ is represented by general formula (8):

(8)

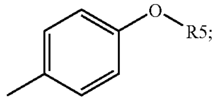

$R^5$ represents hydrogen, optionally substituted alkyl, optionally substituted cycloalkyl, optionally substituted aralkyl, optionally substituted phenyl, optionally substituted heterocycle or optionally substituted heterocyclealkyl;

is treated with a reducing agent or catalytically hydrogenated with a metal catalyst, to stereoselectively form an optically active aminoalcohol derivative represented by general formula (5b):

(5b)

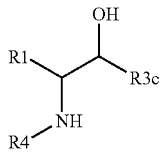

wherein $R^1$, $R^{3c}$ and $R^4$ are as defined above; provided that configuration of $R^1$ attached to the asymmetric carbon at the 2-position and the substituent represented by a nitrogen atom in the optically active aminoketone derivative represented by general formula (4b) is not changed throughout these reactions and relative configuration between the amino group and the hydroxy group in the optically active aminoalcohol derivative represented by general formula (5b) is erythro.

(XXI) A process for preparing an optically active aminoalcohol wherein an optically active aminoketone derivative represented by general formula (4b):

(4b)

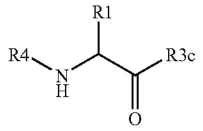

wherein $R^1$ represents an unprotected side chain or optionally protected side chain in a natural α-amino acid; $R^4$ represents hydrogen or optionally substituted alkyloxycarbonyl, optionally substituted aryloxycarbonyl or optionally substituted aralkyloxycarbonyl as a protective group; $R^{3c}$ is represented by general formula (8):

(8)

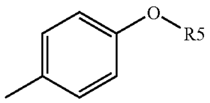

$R^5$ represents hydrogen, optionally substituted alkyl, optionally substituted cycloalkyl, optionally substituted aralkyl, optionally substituted phenyl, optionally substituted heterocycle or optionally substituted heterocyclealkyl;

is treated with a reducing agent or catalytically hydrogenated with a metal catalyst, to stereoselectively form an optically active aminoalcohol derivative represented by general formula (5b):

(5b)

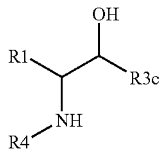

wherein $R^1$, $R^{3c}$ and $R^4$ are as defined above, and when $R^4$ is a protective group, the amino group in the product is deprotected to give an optically active aminoalcohol derivative represented by general formula (6a):

(6a)

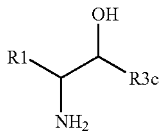

wherein $R^1$ and $R^{3c}$ are as defined above; provided that configuration of $R^1$ attached to the asymmetric carbon at the 2-position and the substituent represented by a nitrogen atom in the optically active aminoketone derivative represented by general formula (4b) is not changed throughout these reactions and relative configuration between the amino group and the hydroxy group in the optically active aminoalcohol derivative represented by general formula (6a) is erythro.

DETAILED DESCRIPTION OF PREFERRED EMBODIMENTS

This invention will be detailed.

The term "unprotected side chain or optionally protected side chain in a natural α-amino acid" as used herein refers to a side chain on an α-carbon such as alanine, valine, leucine, isoleucine, serine, threonine, aspartic acid, glutamic acid, asparagine, glutamine, lysine, hydroxylysine, arginine, cysteine, cystine, methionine, phenylalanine, tyrosine, tryptophan, histidine and ornithine for, for example, an "unprotected side chain in a natural α-amino acid".

An "optionally protected side chain" may be a side chain on an α-carbon in any of the above natural α-amino acid in which a given functional group is protected by a protective group. The protective group may be any of those commonly used in a process known by those skilled in the art. For example, it may be a protective group for an amino, thiol, hydroxy, phenol or carboxyl group used in common preparation of an amino acid.

An "optionally substituted alkyl" means a substituted alkyl at an optional position(s). Examples of the alkyl group include methyl, ethyl, isopropyl, tert-butyl, pentyl, hexyl, octyl, decyl and allyl. Examples of the substituents used include hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

An "optionally substituted aryl" means a substituted aryl at an optional position(s). Examples of the aryl group include phenyl, naphthyl, anthracenyl, fluorenyl and phenanthrenyl. Examples of a substituent(s) used include alkyls such as methyl, tert-butyl and benzyl; cycloalkyls such as cyclopropyl, cyclopentyl and cyclohexyl; phenyl; hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

An "optionally substituted aralkyl" means a substituted aralkyl at an optional position(s). Examples of the aralkyl group include benzyl, naphthylmethyl, phenylethyl and 9-fluorenylmethyl. Examples of a substituent(s) used include alkyls such as methyl, tert-butyl and benzyl; cycloalkyls such as cyclopropyl, cyclopentyl and cyclohexyl; phenyl; hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

An "optionally substituted heterocycle" means an substituted heterocycle at an optional position(s).

Examples of the heterocycle include tetrahydropyranyl, tetrahydrofuranyl, tetrahydrothienyl, piperidyl, morpholinyl, piperazinyl, pyrrolyl, furyl, thienyl, pyridyl, furfuryl, thenyl, pyridylmethyl, pyrimidyl, pyrazyl, imidazoyl, imidazoylmethyl, indolyl, indolylmethyl, isoquinolyl, quinolyl and thiazolyl. Examples of a substituent used include alkyls such as methyl, tert-butyl and benzyl; cycloalkyls such as cyclopropyl, cyclopentyl and cyclohexyl; phenyl; hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

A "heterocyclealkyl" in an optionally substituted heterocyclealkyl means an alkyl substituted with one or more heterocycles at one or more positions, and the "heterocyclealkyl" itself is optionally substituted. Examples of the heterocycle, the alkyl and the substituent therefor may be those described above for an "optionally substituted alkyl" and an "optionally substituted heterocycle".

An "optionally substituted alkyloxycarbonyl" means an optionally substituted alkyloxycarbonyl at given one or more positions. Examples of the alkyloxycarbonyl include methoxycarbonyl, ethoxycarbonyl, isopropoxycarbonyl, tert-butoxycarbonyl, pentyloxycarbonyl, hexyloxycarbonyl, octyloxycarbonyl, decyloxycarbonyl and allyloxycarbonyl. Examples of the substituent(s) used include hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

An "optionally substituted aryloxycarbonyl" means an optionally substituted aryloxycarbonyl at given one or more positions. Examples of the aryloxycarbonyl include phenoxycarbonyl, naphthyloxycarbonyl, anthracenyloxycarbonyl, fluorenyloxycarbonyl and phenanthrenyloxycarbonyl. Examples of the substituent(s) used include alkyls and aralkyls such as methyl, tert-butyl and benzyl; cycloalkyls derived from cyclopropane, cyclopentane and cyclohexane (for example, cyclopropyl, cyclopentyl and cyclohexyl); phenyl; hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

An "optionally substituted aralkyloxycarbonyl" means an optionally substituted aralkyloxycarbonyl at given one or more positions. Examples of the aralkyloxycarbonyl include benzyloxycarbonyl, naphthylmethyloxycarbonyl, phenylethyloxycarbonyl and 9-fluorenylmethyloxycarbonyl. Examples of the substituent(s) used include alkyls and aralkyls; such as methyl, tert-butyl and benzyl; cycloalkyls derived from cyclopropane, cyclopentane and cyclohexane (for example, cyclopropyl, cyclopentyl and cyclohexyl); phenyl; hydroxy; alkoxys such as methoxy, benzyloxy and methoxyethoxy; phenoxy; nitro; amino; amide; carboxyl; alkoxycarbonyl; phenoxycarbonyl; and halogens such as fluorine, chlorine, bromine and iodine.

Each of the above optionally substituted groups may have one or more substituents. When it has a plurality of substituents, each substituent may be independently selected from those described above.

A "halogen" may be fluorine, chlorine, bromine or iodine. Two "Ys" in general formula (7) may be the same or different.

A "reducing agent" means a reagent which can reduce a ketone moiety in the aminoketone derivative represented by general formula (4) into an alcohol moiety, including borane reagents such as borane-tetrahydrofuran complex; borohydride reagents such as sodium borohydride, zinc borohydride and sodium trimethoxy borohydride; alkylaluminum reagents such as diisopropylaluminum hydride; aluminum hydride reagents such as lithium aluminum hydride and lithium trialkoxyaluminum hydride; silane reagents such as trichlorosilane and triethylsilane; sodium metal in liquid ammonia; and magnesium metal in an alcohol.

"Catalytic hydrogenation with a metal catalyst" means reduction of a ketone moiety in the aminoketone derivative represented by general formula (4) into an alcohol moiety by catalytic hydrogenation in the presence of a metal catalyst. Examples of the metal catalyst include nickel catalysts such as Raney nickel, platinum catalysts such as platinum oxide, palladium catalysts such as palladium-carbon or rhodium catalysts such as chlorotris(triphenylphosphine)rhodium which is also known as a Wilkinson catalyst.

"Erythro configuration" is a term indicating a relative configuration of two adjacent asymmetric carbons. For a compound represented by general formula (5) or (6), when the amino and the hydroxy groups as substituents are in the same side in a Ficher projection formula, they have erythro configuration.

Tables 1 to 21 show representative optically active 5-hydroxyoxazolidine derivatives within general formula (3); Tables 22 to 27 show representative optically active aminoketone derivatives within general formula (4); and Tables 28 to 39 show representative optically active aminoalcohol derivatives within general formula (5) or (6), but this invention is not limited to these exemplified compounds. In these Tables, Ph is phenyl or phenylene; Me is methyl; Boc is tert-butoxycarbonyl as a protective group.

TABLE 1

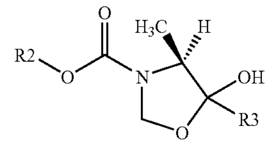

| Example Compound No. | R2— | R3— |
|---|---|---|
| 1001 | $PhCH_2$— | p-$PhCH_2OPh$— |
| 1002 | $CH_3$— | p-$PhCH_2OPh$— |
| 1003 | 9-Fluorenylmethyl- | p-$PhCH_2OPh$— |
| 1004 | $(CH_3)_3C$— | o-$PhCH_2OPh$— |
| 1005 | $CH_3$— | m-$PhCH_2OPh$— |
| 1006 | $PhCH_2$— | p-$NO_2Ph$— |
| 1007 | $(CH_3)_3C$— | p-MeOPh— |
| 1008 | $PhCH_2$— | p-HOPh— |
| 1009 | $(CH_3)_3C$— | Ph— |
| 1010 | $PhCH_2$— | p-FPh |
| 1011 | $PhCH_2$— | 3-Indolyl- |
| 1012 | $CH_3$— | 3-Indolyl- |
| 1013 | $PhCH_2$— | 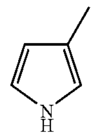 |
| 1014 | $PhCH_2$— | 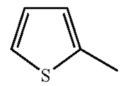 |
| 1015 | $(CH_3)_3C$— | p-$PhCH_2OPh$— |

TABLE 1-continued

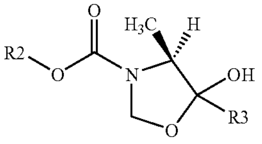

| Example Compound No. | R2— | R3— |
|---|---|---|
| 1016 | $CH_3CH_2$— | p-$PhCH_2OPh$— |
| 1017 | $PhCH_2$— | o-$PhCH_2OPh$— |
| 1018 | $(CH_3)_3C$— | m-$PhCH_2OPh$— |
| 1019 | $CH_3CH_2$— | o-$PhCH_2OPh$— |
| 1020 | $PhCH_2$— | p-MeOPh— |
| 1021 | $(CH_3)_3C$— | m-MeOPh— |
| 1022 | $PhCH_2$— | Ph |
| 1023 | $PhCH_2$— | p-$CH_3Ph$— |
| 1024 | $(CH_3)_3C$— | p-ClPh— |
| 1025 | $(CH_3)_3C$— | 3-Indolyl- |
| 1026 | 9-Fluorenylmethyl- | 3-Indolyl- |
| 1027 | $(CH_3)_3C$— | 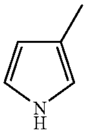 |
| 1028 | 9-Fluorenylmethyl- | 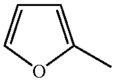 |
| 1029 | $(CH_3)_3C$— | 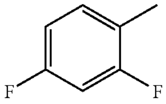 |
| 1030 | $PhCH_2$— | 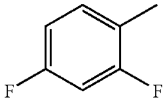 |
| 1031 | $(CH3)_2CH$— | 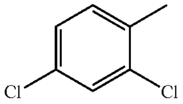 |

TABLE 2

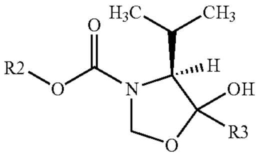

| Example Compound No. | R2— | R3— |
|---|---|---|
| 2001 | $PhCH_2$— | p-$PhCH_2OPh$— |
| 2002 | $CH_3$— | p-$PhCH_2OPh$— |
| 2003 | 9-Fluorenylmethyl- | p-$PhCH_2OPh$— |
| 2004 | $(CH_3)_3C$— | o-$PhCH_2OPh$— |
| 2005 | $CH_3$— | m-$PhCH_2OPh$— |
| 2006 | $PhCH_2$— | p-$NO_2Ph$— |
| 2007 | $(CH_3)_3C$— | p-MeOPh— |
| 2008 | $PhCH_2$— | p-HOPh— |
| 2009 | $(CH_3)_3C$— | Ph— |
| 2010 | $PhCH_2$— | p-FPh |
| 2011 | $PhCH_2$— | 3-Indolyl- |

TABLE 2-continued

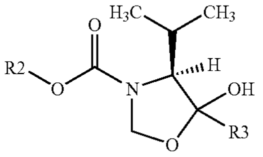

| Example Compound No. | R2— | R3— |
|---|---|---|
| 2012 | $CH_3$— | 3-Indolyl- |
| 2013 | $PhCH_2$— | 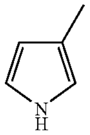 |
| 2014 | $PhCH_2$— | 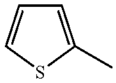 |
| 2015 | $(CH_3)_3C$— | p-$PhCH_2OPh$— |
| 2016 | $CH_3CH_2$— | p-$PhCH_2OPh$— |
| 2017 | $PhCH_2$— | o-$PhCH_2OPh$— |
| 2018 | $(CH_3)_3C$— | m-$PhCH_2OPh$— |
| 2019 | $CH_3CH_2$— | o-$PhCH_2OPh$— |
| 2020 | $PhCH_2$— | p-MeOPh— |
| 2021 | $(CH_3)_3C$— | m-MeOPh— |
| 2022 | $PhCH_2$— | Ph |
| 2023 | $PhCH_2$— | p-$CH_3Ph$— |
| 2024 | $(CH_3)_3C$— | p-ClPh— |
| 2025 | $(CH_3)_3C$— | 3-Indolyl- |
| 2026 | 9-Fluorenylmethyl- | 3-Indolyl- |
| 2027 | $(CH_3)_3C$— | 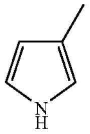 |
| 2028 | 9-Fluorenylmethyl- | 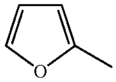 |
| 2029 | $(CH_3)_3C$— | 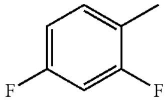 |
| 2030 | $PhCH_2$— | 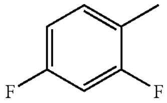 |
| 2031 | $(CH3)_2CH$— | 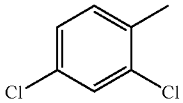 |

TABLE 3

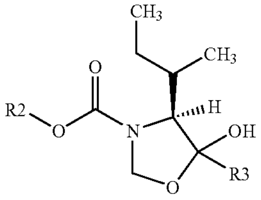

| Example Compound No. | R2— | R3— |
|---|---|---|
| 3001 | $PhCH_2$— | p-$PhCH_2OPh$— |
| 3002 | $CH_3$— | p-$PhCH_2OPh$— |
| 3003 | 9-Fluorenylmethyl- | p-$PhCH_2OPh$— |
| 3004 | $(CH_3)_3C$— | o-$PhCH_2OPh$— |
| 3005 | $CH_3$— | m-$PhCH_2OPh$— |
| 3006 | $PhCH_2$— | p-$NO_2Ph$— |
| 3007 | $(CH_3)_3C$— | p-MeOPh— |
| 3008 | $PhCH_2$— | p-HOPh— |
| 3009 | $(CH_3)_3C$— | Ph— |
| 3010 | $PhCH_2$— | p-FPh |
| 3011 | $PhCH_2$— | 3-Indolyl- |
| 3012 | $CH_3$— | 3-Indolyl- |
| 3013 | $PhCH_2$— | 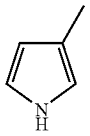 |
| 3014 | $PhCH_2$— | 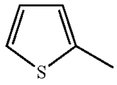 |
| 3015 | $(CH_3)_3C$— | p-$PhCH_2OPh$— |
| 3016 | $CH_3CH_2$— | p-$PhCH_2OPh$— |
| 3017 | $PhCH_2$— | o-$PhCH_2OPh$— |
| 3018 | $(CH_3)_3C$— | m-$PhCH_2OPh$— |
| 3019 | $CH_3CH_2$— | o-$PhCH_2OPh$— |
| 3020 | $PhCH_2$— | p-MeOPh— |
| 3021 | $(CH_3)_3C$— | m-MeOPh— |
| 3022 | $PhCH_2$— | Ph |
| 3023 | $PhCH_2$— | p-$CH_3Ph$— |
| 3024 | $(CH_3)_3C$— | p-ClPh— |
| 3025 | $(CH_3)_3C$— | 3-Indolyl- |
| 3026 | 9-Fluorenylmethyl- | 3-Indolyl- |
| 3027 | $(CH_3)_3C$— | 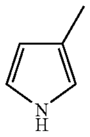 |
| 3028 | 9-Fluorenylmethyl- | 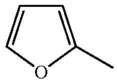 |
| 3029 | $(CH_3)_3C$— | 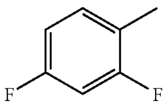 |
| 3030 | $PhCH_2$— | 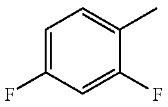 |

TABLE 3-continued

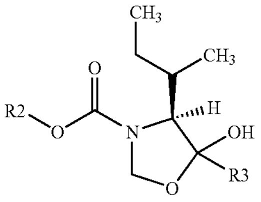

| Example Compound No. | R2— | R3— |
|---|---|---|
| 3031 | $(CH3)_2CH$— | 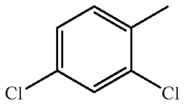 |

TABLE 4

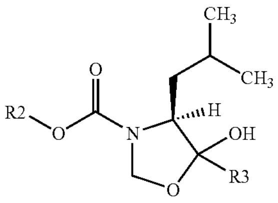

| Example Compound No. | R2— | R3— |
|---|---|---|
| 4001 | $PhCH_2$— | p-$PhCH_2OPh$— |
| 4002 | $CH_3$— | p-$PhCH_2OPh$— |
| 4003 | 9-Fluorenylmethyl- | p-$PhCH_2OPh$— |
| 4004 | $(CH_3)_3C$— | o-$PhCH_2OPh$— |
| 4005 | $CH_3$— | m-$PhCH_2OPh$— |
| 4006 | $PhCH_2$— | p-$NO_2Ph$— |
| 4007 | $(CH_3)_3C$— | p-MeOPh— |
| 4008 | $PhCH_2$— | p-HOPh— |
| 4009 | $(CH_3)_3C$— | Ph— |
| 4010 | $PhCH_2$— | p-FPh |
| 4011 | $PhCH_2$— | 3-Indolyl- |
| 4012 | $CH_3$— | 3-Indolyl- |
| 4013 | $PhCH_2$— | 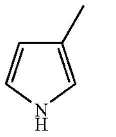 |
| 4014 | $PhCH_2$— | 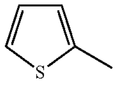 |
| 4015 | $(CH_3)_3C$— | p-$PhCH_2OPh$— |
| 4016 | $CH_3CH_2$— | p-$PhCH_2OPh$— |
| 4017 | $PhCH_2$— | o-$PhCH_2OPh$— |
| 4018 | $(CH_3)_3C$— | m-$PhCH_2OPh$— |
| 4019 | $CH_3CH_2$— | o-$PhCH_2OPh$— |
| 4020 | $PhCH_2$— | p-MeOPh— |
| 4021 | $(CH_3)_3C$— | m-MeOPh— |
| 4022 | $PhCH_2$— | Ph |
| 4023 | $PhCH_2$— | p-$CH_3Ph$— |
| 4024 | $(CH_3)_3C$— | p-ClPh— |
| 4025 | $(CH_3)_3C$— | 3-Indolyl- |
| 4026 | 9-Fluorenylmethyl- | 3-Indolyl- |

TABLE 4-continued

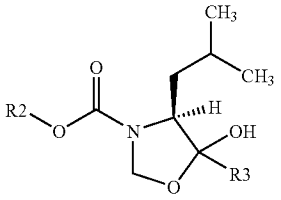

| Example Compound No. | R2— | R3— |
|---|---|---|
| 4027 | $(CH_3)_3C$— | 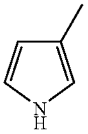 |
| 4028 | 9-Fluorenylmethyl- | 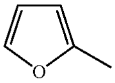 |
| 4029 | $(CH_3)_3C$— | 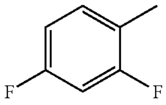 |
| 4030 | $PhCH_2$— | 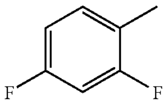 |
| 4031 | $(CH3)_2CH$— | 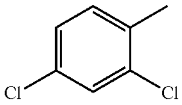 |

TABLE 5

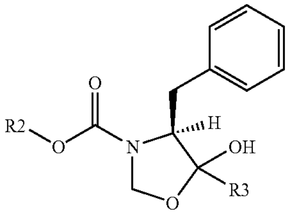

| Example Compound No. | R2— | R3— |
|---|---|---|
| 5001 | $PhCH_2$— | p-$PhCH_2OPh$— |
| 5002 | $CH_3$— | p-$PhCH_2OPh$— |
| 5003 | 9-Fluorenylmethyl- | p-$PhCH_2OPh$— |
| 5004 | $(CH_3)_3C$— | o-$PhCH_2OPh$— |
| 5005 | $CH_3$— | m-$PhCH_2OPh$— |
| 5006 | $PhCH_2$— | p-$NO_2Ph$— |
| 5007 | $(CH_3)_3C$— | p-MeOPh— |
| 5008 | $PhCH_2$— | p-HOPh— |
| 5009 | $(CH_3)_3C$— | Ph— |
| 5010 | $PhCH_2$— | p-FPh |
| 5011 | $PhCH_2$— | 3-Indolyl- |
| 5012 | $CH_3$— | 3-Indolyl- |

TABLE 5-continued

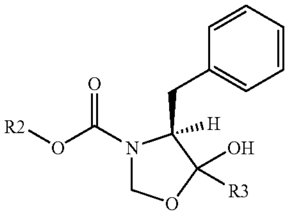

| Example Compound No. | R2— | R3— |
|---|---|---|
| 5013 | $PhCH_2$— | 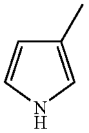 |
| 5014 | $PhCH_2$— | 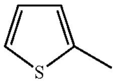 |
| 5015 | $(CH_3)_3C$— | p-$PhCH_2OPh$— |
| 5016 | $CH_3CH_2$— | p-$PhCH_2OPh$— |
| 5017 | $PhCH_2$— | o-$PhCH_2OPh$— |
| 5018 | $(CH_3)_3C$— | m-$PhCH_2OPh$— |
| 5019 | $CH_3CH_2$— | o-$PhCH_2OPh$— |
| 5020 | $PhCH_2$— | p-MeOPh— |
| 5021 | $(CH_3)_3C$— | m-MeOPh— |
| 5022 | $PhCH_2$— | Ph |
| 5023 | $PhCH_2$— | p-$CH_3Ph$— |
| 5024 | $(CH_3)_3C$— | p-ClPh— |
| 5025 | $(CH_3)_3C$— | 3-Indolyl- |
| 5026 | 9-Fluorenylmethyl- | 3-Indolyl- |
| 5027 | $(CH_3)_3C$— | 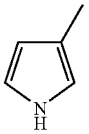 |
| 5028 | 9-Fluorenylmethyl- | 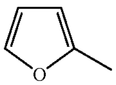 |
| 5029 | $(CH_3)_3C$— | 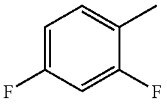 |
| 5030 | $PhCH_2$— | 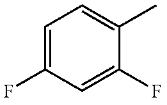 |
| 5031 | $(CH3)_2CH$— | 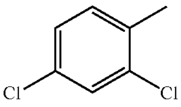 |

TABLE 6

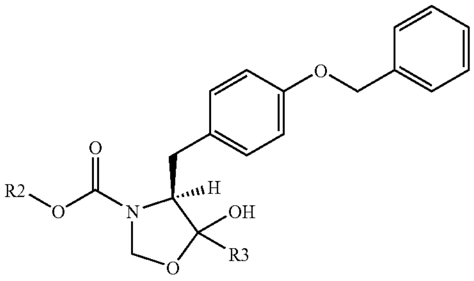

| Example Compound No. | R2— | R3— |
|---|---|---|
| 6001 | $PhCH_2$— | p-$PhCH_2OPh$— |
| 6002 | $CH_3$— | p-$PhCH_2OPh$— |
| 6003 | 9-Fluorenylmethyl- | p-$PhCH_2OPh$— |
| 6004 | $(CH_3)_3C$— | o-$PhCH_2OPh$— |
| 6005 | $CH_3$— | m-$PhCH_2OPh$— |
| 6006 | $PhCH_2$— | p-$NO_2Ph$— |
| 6007 | $(CH_3)_3C$— | p-MeOPh— |
| 6008 | $PhCH_2$— | p-HOPh— |
| 6009 | $(CH_3)_3C$— | Ph— |
| 6010 | $PhCH_2$— | p-FPh |
| 6011 | $PhCH_2$— | 3-Indolyl- |
| 6012 | $CH_3$— | 3-Indolyl- |
| 6013 | $PhCH_2$— | 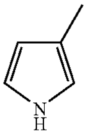 |
| 6014 | $PhCH_2$— | 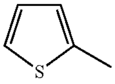 |
| 6015 | $(CH_3)_3C$— | p-$PhCH_2OPh$— |
| 6016 | $CH_3CH_2$— | p-$PhCH_2OPh$— |
| 6017 | $PhCH_2$— | o-$PhCH_2OPh$— |
| 6018 | $(CH_3)_3C$— | m-$PhCH_2OPh$— |
| 6019 | $CH_3CH_2$— | o-$PhCH_2OPh$— |
| 6020 | $PhCH_2$— | p-MeOPh— |
| 6021 | $(CH_3)_3C$— | m-MeOPh— |
| 6022 | $PhCH_2$— | Ph |
| 6023 | $PhCH_2$— | p-$CH_3Ph$— |
| 6024 | $(CH_3)_3C$— | p-ClPh— |
| 6025 | $(CH_3)_3C$— | 3-Indolyl- |
| 6026 | 9-Fluorenylmethyl- | 3-Indolyl- |
| 6027 | $(CH_3)_3C$— | 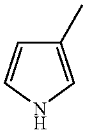 |
| 6028 | 9-Fluorenylmethyl- | 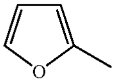 |
| 6029 | $(CH_3)_3C$— | 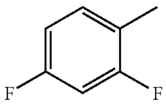 |
| 6030 | $PhCH_2$— | 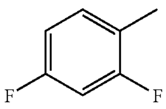 |

TABLE 6-continued

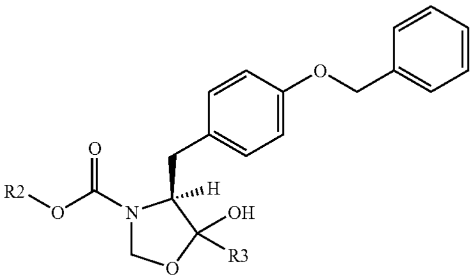

| Example Compound No. | R2— | R3— |
|---|---|---|
| 6031 | $(CH3)_2CH$— | 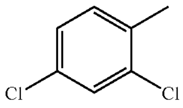 |

TABLE 7

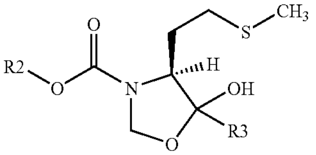

| Example Compound No. | R2— | R3— |
|---|---|---|
| 7001 | $PhCH_2$— | p-$PhCH_2OPh$— |
| 7002 | $CH_3$— | p-$PhCH_2OPh$— |
| 7003 | 9-Fluorenylmethyl- | p-$PhCH_2OPh$— |
| 7004 | $(CH_3)_3C$— | o-$PhCH_2OPh$— |
| 7005 | $CH_3$— | m-$PhCH_2OPh$— |
| 7006 | $PhCH_2$— | p-$NO_2Ph$— |
| 7007 | $(CH_3)_3C$— | p-MeOPh— |
| 7008 | $PhCH_2$— | p-HOPh— |
| 7009 | $(CH_3)_3C$— | Ph— |
| 7010 | $PhCH_2$— | p-FPh |
| 7011 | $PhCH_2$— | 3-Indolyl- |
| 7012 | $CH_3$— | 3-Indolyl- |
| 7013 | $PhCH_2$— | 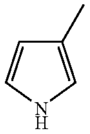 |
| 7014 | $PhCH_2$— | 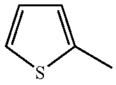 |
| 7015 | $(CH_3)_3C$— | p-$PhCH_2OPh$— |
| 7016 | $CH_3CH_2$— | p-$PhCH_2OPh$— |
| 7017 | $PhCH_2$— | o-$PhCH_2OPh$— |
| 7018 | $(CH_3)_3C$— | m-$PhCH_2OPh$— |
| 7019 | $CH_3CH_2$— | o-$PhCH_2OPh$— |
| 7020 | $PhCH_2$— | p-MeOPh— |
| 7021 | $(CH_3)_3C$— | m-MeOPh— |
| 7022 | $PhCH_2$— | Ph |
| 7023 | $PhCH_2$— | p-$CH_3Ph$— |
| 7024 | $(CH_3)_3C$— | p-ClPh— |
| 7025 | $(CH_3)_3C$— | 3-Indolyl- |
| 7026 | 9-Fluorenylmethyl- | 3-Indolyl- |

TABLE 7-continued

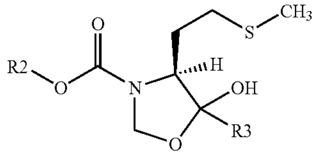

| Example Compound No. | R2— | R3— |
|---|---|---|
| 7027 | $(CH_3)_3C$— | 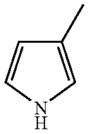 |
| 7028 | 9-Fluorenylmethyl- | 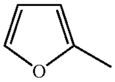 |
| 7029 | $(CH_3)_3C$— | 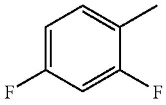 |
| 7030 | $PhCH_2$— | 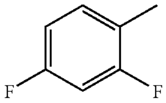 |
| 7031 | $(CH3)_2CH$— | 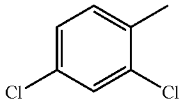 |

TABLE 8

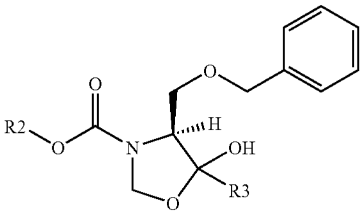

| Example Compound No. | R2— | R3— |
|---|---|---|
| 8001 | $PhCH_2$— | p-$PhCH_2OPh$— |
| 8002 | $CH_3$— | p-$PhCH_2OPh$— |
| 8003 | 9-Fluorenylmethyl- | p-$PhCH_2OPh$— |
| 8004 | $(CH_3)_3C$— | o-$PhCH_2OPh$— |
| 8005 | $CH_3$— | m-$PhCH_2OPh$— |
| 8006 | $PhCH_2$— | p-$NO_2Ph$— |
| 8007 | $(CH_3)_3C$— | p-MeOPh— |
| 8008 | $PhCH_2$— | p-HOPh— |
| 8009 | $(CH_3)_3C$— | Ph— |
| 8010 | $PhCH_2$— | p-FPh |
| 8011 | $PhCH_2$— | 3-Indolyl- |
| 8012 | $CH_3$— | 3-Indolyl- |
| 8013 | $PhCH_2$— | 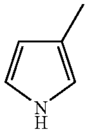 |

TABLE 8-continued

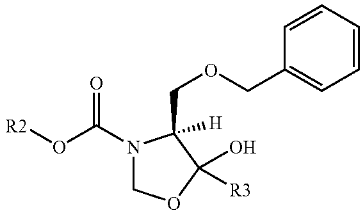

| Example Compound No. | R2— | R3— |
|---|---|---|
| 8014 | $PhCH_2$— | 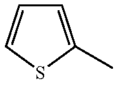 |
| 8015 | $(CH_3)_3C$— | p-$PhCH_2OPh$— |
| 8016 | $CH_3CH_2$— | p-$PhCH_2OPh$— |
| 8017 | $PhCH_2$— | o-$PhCH_2OPh$— |
| 8018 | $(CH_3)_3C$— | m-$PhCH_2OPh$— |
| 8019 | $CH_3CH_2$— | o-$PhCH_2OPh$— |
| 8020 | $PhCH_2$— | p-MeOPh— |
| 8021 | $(CH_3)_3C$— | m-MeOPh— |
| 8022 | $PhCH_2$— | Ph |
| 8023 | $PhCH_2$— | p-$CH_3Ph$— |
| 8024 | $(CH_3)_3C$— | p-ClPh— |
| 8025 | $(CH_3)_3C$— | 3-Indolyl- |
| 8026 | 9-Fluorenylmethyl- | 3-Indolyl- |
| 8027 | $(CH_3)_3C$— | 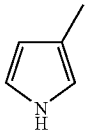 |
| 8028 | 9-Fluorenylmethyl- | 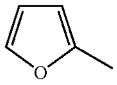 |
| 8029 | $(CH_3)_3C$— | 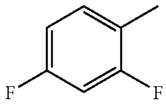 |
| 8030 | $PhCH_2$— | 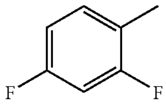 |
| 8031 | $(CH3)_2CH$— | 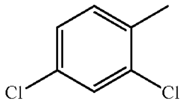 |

TABLE 9

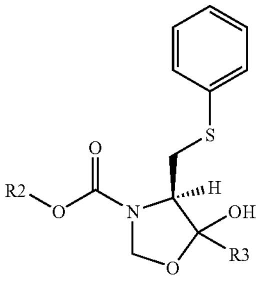

| Example Compound No. | R2— | R3— |
|---|---|---|
| 9001 | $PhCH_2$— | p-$PhCH_2OPh$— |
| 9002 | $CH_3$— | p-$PhCH_2OPh$— |
| 9003 | 9-Fluorenylmethyl- | p-$PhCH_2OPh$— |
| 9004 | $(CH_3)_3C$— | o-$PhCH_2OPh$— |
| 9005 | $CH_3$— | m-$PhCH_2OPh$— |
| 9006 | $PhCH_2$— | p-$NO_2Ph$— |
| 9007 | $(CH_3)_3C$— | p-MeOPh— |
| 9008 | $PhCH_2$— | p-HOPh— |
| 9009 | $(CH_3)_3C$— | Ph— |
| 9010 | $PhCH_2$— | p-FPh |
| 9011 | $PhCH_2$— | 3-Indolyl- |
| 9012 | $CH_3$— | 3-Indolyl- |
| 9013 | $PhCH_2$— | 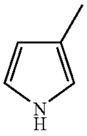 |
| 9014 | $PhCH_2$— | 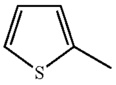 |
| 9015 | $(CH_3)_3C$— | p-$PhCH_2OPh$— |
| 9016 | $CH_3CH_2$— | p-$PhCH_2OPh$— |
| 9017 | $PhCH_2$— | o-$PhCH_2OPh$— |
| 9018 | $(CH_3)_3C$— | m-$PhCH_2OPh$— |
| 9019 | $CH_3CH_2$— | o-$PhCH_2OPh$— |
| 9020 | $PhCH_2$— | p-MeOPh— |
| 9021 | $(CH_3)_3C$— | m-MeOPh— |
| 9022 | $PhCH_2$— | Ph |
| 9023 | $PhCH_2$— | p-$CH_3Ph$— |
| 9024 | $(CH_3)_3C$— | p-ClPh— |
| 9025 | $(CH_3)_3C$— | 3-Indolyl- |
| 9026 | 9-Fluorenylmethyl- | 3-Indolyl- |
| 9027 | $(CH_3)_3C$— | 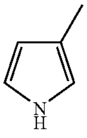 |
| 9028 | 9-Fluorenylmethyl- | 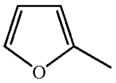 |
| 9029 | $(CH_3)_3C$— | 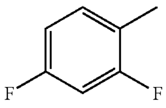 |
| 9030 | $PhCH_2$— | 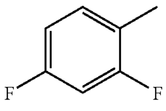 |

TABLE 9-continued

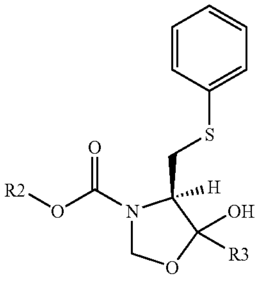

| Example Compound No. | R2— | R3— |
|---|---|---|
| 9031 | $(CH3)_2CH$— | 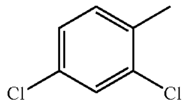 |

TABLE 10

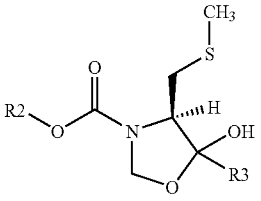

| Example Compound No. | R2— | R3— |
|---|---|---|
| 10001 | $PhCH_2$— | p-$PhCH_2OPh$— |
| 10002 | $CH_3$— | p-$PhCH_2OPh$— |
| 10003 | 9-Fluorenylmethyl- | p-$PhCH_2OPh$— |
| 10004 | $(CH_3)_3C$— | o-$PhCH_2OPh$— |
| 10005 | $CH_3$— | m-$PhCH_2OPh$— |
| 10006 | $PhCH_2$— | p-$NO_2Ph$— |
| 10007 | $(CH_3)_3C$— | p-MeOPh— |
| 10008 | $PhCH_2$— | p-HOPh— |
| 10009 | $(CH_3)_3C$— | Ph— |
| 10010 | $PhCH_2$— | p-FPh |
| 10011 | $PhCH_2$— | 3-Indolyl- |
| 10012 | $CH_3$— | 3-Indolyl- |
| 10013 | $PhCH_2$— | 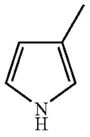 |
| 10014 | $PhCH_2$— | 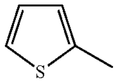 |
| 10015 | $(CH_3)_3C$— | p-$PhCH_2OPh$— |
| 10016 | $CH_3CH_2$— | p-$PhCH_2OPh$— |
| 10017 | $PhCH_2$— | o-$PhCH_2OPh$— |
| 10018 | $(CH_3)_3C$— | m-$PhCH_2OPh$— |
| 10019 | $CH_3CH_2$— | o-$PhCH_2OPh$— |
| 10020 | $PhCH_2$— | p-MeOPh— |
| 10021 | $(CH_3)_3C$— | m-MeOPh— |
| 10022 | $PhCH_2$— | Ph |
| 10023 | $PhCH_2$— | p-$CH_3Ph$— |
| 10024 | $(CH_3)_3C$— | p-ClPh— |
| 10025 | $(CH_3)_3C$— | 3-Indolyl- |
| 10026 | 9-Fluorenylmethyl- | 3-Indolyl- |

TABLE 10-continued

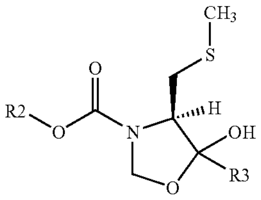

| Example Compound No. | R2— | R3— |
| --- | --- | --- |
| 10027 | $(CH_3)_3C$— | 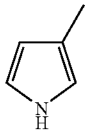 |
| 10028 | 9-Fluorenylmethyl- | 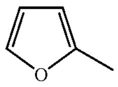 |
| 10029 | $(CH_3)_3C$— | 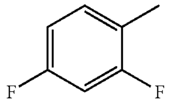 |
| 10030 | $PhCH_2$— | 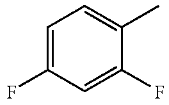 |
| 10031 | $(CH3)_2CH$— | 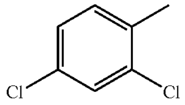 |

TABLE 11

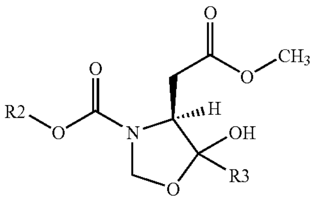

| Example Compound No. | R2— | R3— |
| --- | --- | --- |
| 11001 | $PhCH_2$— | p-$PhCH_2OPh$— |
| 11002 | $CH_3$— | p-$PhCH_2OPh$— |
| 11003 | 9-Fluorenylmethyl- | p-$PhCH_2OPh$— |
| 11004 | $(CH_3)_3C$— | o-$PhCH_2OPh$— |
| 11005 | $CH_3$— | m-$PhCH_2OPh$— |
| 11006 | $PhCH_2$— | p-$NO_2Ph$— |
| 11007 | $(CH_3)_3C$— | p-MeOPh— |
| 11008 | $PhCH_2$— | p-HOPh— |
| 11009 | $(CH_3)_3C$— | Ph— |
| 11010 | $PhCH_2$— | p-FPh |
| 11011 | $PhCH_2$— | 3-Indolyl- |
| 11012 | $CH_3$— | 3-Indolyl- |

TABLE 11-continued

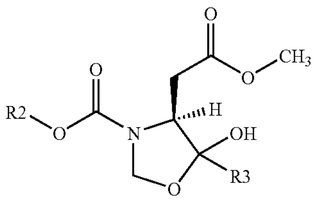

| Example Compound No. | R2— | R3— |
| --- | --- | --- |
| 11013 | $PhCH_2$— | 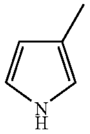 |
| 11014 | $PhCH_2$— | 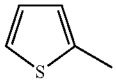 |
| 11015 | $(CH_3)_3C$— | p-$PhCH_2OPh$— |
| 11016 | $CH_3CH_2$— | p-$PhCH_2OPh$— |
| 11017 | $PhCH_2$— | o-$PhCH_2OPh$— |
| 11018 | $(CH_3)_3C$— | m-$PhCH_2OPh$— |
| 11019 | $CH_3CH_2$— | o-$PhCH_2OPh$— |
| 11020 | $PhCH_2$— | p-MeOPh— |
| 11021 | $(CH_3)_3C$— | m-MeOPh— |
| 11022 | $PhCH_2$— | Ph |
| 11023 | $PhCH_2$— | p-$CH_3Ph$— |
| 11024 | $(CH_3)_3C$— | p-ClPh— |
| 11025 | $(CH_3)_3C$— | 3-Indolyl- |
| 11026 | 9-Fluorenylmethyl- | 3-Indolyl- |
| 11027 | $(CH_3)_3C$— | 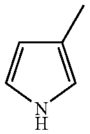 |
| 11028 | 9-Fluorenylmethyl- | 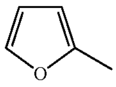 |
| 11029 | $(CH_3)_3C$— | 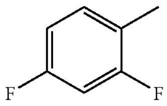 |
| 11030 | $PhCH_2$— | 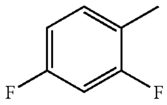 |
| 11031 | $(CH3)_2CH$— | 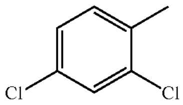 |

TABLE 12

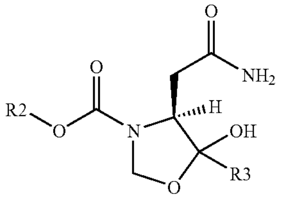

| Example Compound No. | R2— | R3— |
|---|---|---|
| 12001 | $PhCH_2$— | p-$PhCH_2OPh$— |
| 12002 | $CH_3$— | p-$PhCH_2OPh$— |
| 12003 | 9-Fluorenylmethyl- | p-$PhCH_2OPh$— |
| 12004 | $(CH_3)_3C$— | o-$PhCH_2OPh$— |
| 12005 | $CH_3$— | m-$PhCH_2OPh$— |
| 12006 | $PhCH_2$— | p-$NO_2Ph$— |
| 12007 | $(CH_3)_3C$— | p-MeOPh— |
| 12008 | $PhCH_2$— | p-HOPh— |
| 12009 | $(CH_3)_3C$— | Ph— |
| 12010 | $PhCH_2$— | p-FPh |
| 12011 | $PhCH_2$— | 3-Indolyl- |
| 12012 | $CH_3$— | 3-Indolyl- |
| 12013 | $PhCH_2$— | 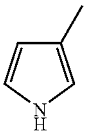 |
| 12014 | $PhCH_2$— | 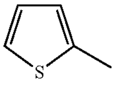 |
| 12015 | $(CH_3)_3C$— | p-$PhCH_2OPh$— |
| 12016 | $CH_3CH_2$— | p-$PhCH_2OPh$— |
| 12017 | $PhCH_2$— | o-$PhCH_2OPh$— |
| 12018 | $(CH_3)_3C$— | m-$PhCH_2OPh$— |
| 12019 | $CH_3CH_2$— | o-$PhCH_2OPh$— |
| 12020 | $PhCH_2$— | p-MeOPh— |
| 12021 | $(CH_3)_3C$— | m-MeOPh— |
| 12022 | $PhCH_2$— | Ph |
| 12023 | $PhCH_2$— | p-$CH_3Ph$— |
| 12024 | $(CH_3)_3C$— | p-ClPh— |
| 12025 | $(CH_3)_3C$— | 3-Indolyl- |
| 12026 | 9-Fluorenylmethyl- | 3-Indolyl- |
| 12027 | $(CH_3)_3C$— | 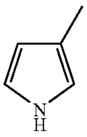 |
| 12028 | 9-Fluorenylmethyl- | 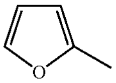 |
| 12029 | $(CH_3)_3C$— | 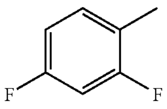 |
| 12030 | $PhCH_2$— | 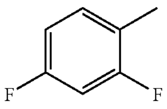 |

TABLE 12-continued

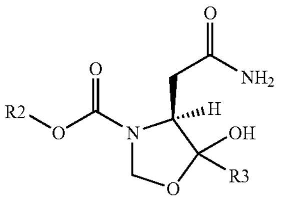

| Example Compound No. | R2— | R3— |
|---|---|---|
| 12031 | $(CH3)_2CH$— | 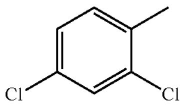 |

TABLE 13

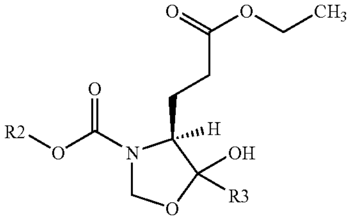

| Example Compound No. | R2— | R3— |
|---|---|---|
| 13001 | $PhCH_2$— | p-$PhCH_2OPh$— |
| 13002 | $CH_3$— | p-$PhCH_2OPh$— |
| 13003 | 9-Fluorenylmethyl- | p-$PhCH_2OPh$— |
| 13004 | $(CH_3)_3C$— | o-$PhCH_2OPh$— |
| 13005 | $CH_3$— | m-$PhCH_2OPh$— |
| 13006 | $PhCH_2$— | p-$NO_2Ph$— |
| 13007 | $(CH_3)_3C$— | p-MeOPh— |
| 13008 | $PhCH_2$— | p-HOPh— |
| 13009 | $(CH_3)_3C$— | Ph— |
| 13010 | $PhCH_2$— | p-FPh |
| 13011 | $PhCH_2$— | 3-Indolyl- |
| 13012 | $CH_3$— | 3-Indolyl- |
| 13013 | $PhCH_2$— | 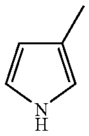 |
| 13014 | $PhCH_2$— | 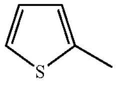 |
| 13015 | $(CH_3)_3C$— | p-$PhCH_2OPh$— |
| 13016 | $CH_3CH_2$— | p-$PhCH_2OPh$— |
| 13017 | $PhCH_2$— | o-$PhCH_2OPh$— |
| 13018 | $(CH_3)_3C$— | m-$PhCH_2OPh$— |
| 13019 | $CH_3CH_2$— | o-$PhCH_2OPh$— |
| 13020 | $PhCH_2$— | p-MeOPh— |
| 13021 | $(CH_3)_3C$— | m-MeOPh— |
| 13022 | $PhCH_2$— | Ph |
| 13023 | $PhCH_2$— | p-$CH_3Ph$— |
| 13024 | $(CH_3)_3C$— | p-ClPh— |
| 13025 | $(CH_3)_3C$— | 3-Indolyl- |
| 13026 | 9-Fluorenylmethyl- | 3-Indolyl- |

TABLE 13-continued

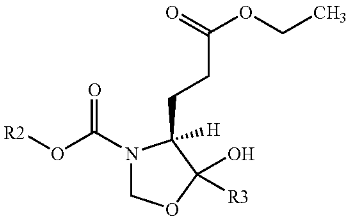

| Example Compound No. | R2— | R3— |
|---|---|---|
| 13027 | $(CH_3)_3C$— | 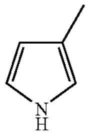 |
| 13028 | 9-Fluorenylmethyl- | 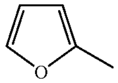 |
| 13029 | $(CH_3)_3C$— | 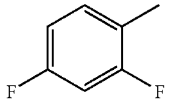 |
| 13030 | $PhCH_2$— | 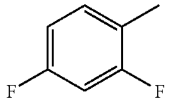 |
| 13031 | $(CH3)_2CH$— | 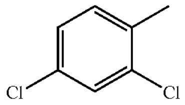 |

TABLE 14

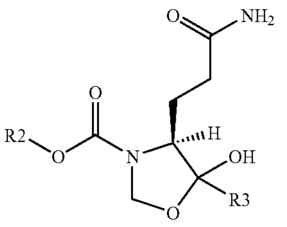

| Example Compound No. | R2— | R3— |
|---|---|---|
| 14001 | $PhCH_2$— | p-$PhCH_2OPh$— |
| 14002 | $CH_3$— | p-$PhCH_2OPh$— |
| 14003 | 9-Fluorenylmethyl- | p-$PhCH_2OPh$— |
| 14004 | $(CH_3)_3C$— | o-$PhCH_2OPh$— |
| 14005 | $CH_3$— | m-$PhCH_2OPh$— |
| 14006 | $PhCH_2$— | p-$NO_2Ph$— |
| 14007 | $(CH_3)_3C$— | p-MeOPh— |
| 14008 | $PhCH_2$— | p-HOPh— |
| 14009 | $(CH_3)_3C$— | Ph— |
| 14010 | $PhCH_2$— | p-FPh |
| 14011 | $PhCH_2$— | 3-Indolyl- |
| 14012 | $CH_3$— | 3-Indolyl- |

TABLE 14-continued

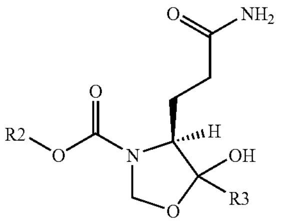

| Example Compound No. | R2— | R3— |
|---|---|---|
| 14013 | $PhCH_2$— | 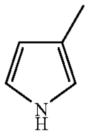 |
| 14014 | $PhCH_2$— | 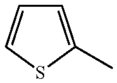 |
| 14015 | $(CH_3)_3C$— | p-$PhCH_2OPh$— |
| 14016 | $CH_3CH_2$— | p-$PhCH_2OPh$— |
| 14017 | $PhCH_2$— | o-$PhCH_2OPh$— |
| 14018 | $(CH_3)_3C$— | m-$PhCH_2OPh$— |
| 14019 | $CH_3CH_2$— | o-$PhCH_2OPh$— |
| 14020 | $PhCH_2$— | p-MeOPh— |
| 14021 | $(CH_3)_3C$— | m-MeOPh— |
| 14022 | $PhCH_2$— | Ph |
| 14023 | $PhCH_2$— | p-$CH_3Ph$— |
| 14024 | $(CH_3)_3C$— | p-ClPh— |
| 14025 | $(CH_3)_3C$— | 3-Indolyl- |
| 14026 | 9-Fluorenylmethyl- | 3-Indolyl- |
| 14027 | $(CH_3)_3C$— | 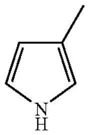 |
| 14028 | 9-Fluorenylmethyl- | 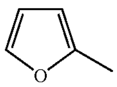 |
| 14029 | $(CH_3)_3C$— | 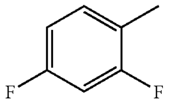 |
| 14030 | $PhCH_2$— | 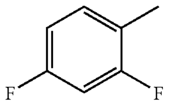 |
| 14031 | $(CH3)_2CH$— | 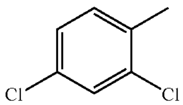 |

TABLE 15

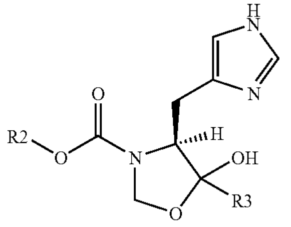

| Example Compound No. | R2— | R3— |
|---|---|---|
| 15001 | $PhCH_2$— | p-$PhCH_2OPh$— |
| 15002 | $CH_3$— | p-$PhCH_2OPh$— |
| 15003 | 9-Fluorenylmethyl- | p-$PhCH_2OPh$— |
| 15004 | $(CH_3)_3C$— | o-$PhCH_2OPh$— |
| 15005 | $CH_3$— | m-$PhCH_2OPh$— |
| 15006 | $PhCH_2$— | p-$NO_2Ph$— |
| 15007 | $(CH_3)_3C$— | p-MeOPh— |
| 15008 | $PhCH_2$— | p-HOPh— |
| 15009 | $(CH_3)_3C$— | Ph— |
| 15010 | $PhCH_2$— | p-FPh |
| 15011 | $PhCH_2$— | 3-Indolyl- |
| 15012 | $CH_3$— | 3-Indolyl- |
| 15013 | $PhCH_2$— | 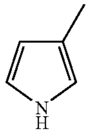 |
| 15014 | $PhCH_2$— | 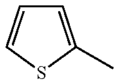 |
| 15015 | $(CH_3)_3C$— | p-$PhCH_2OPh$— |
| 15016 | $CH_3CH_2$— | p-$PhCH_2OPh$— |
| 15017 | $PhCH_2$— | o-$PhCH_2OPh$— |
| 15018 | $(CH_3)_3C$— | m-$PhCH_2OPh$— |
| 15019 | $CH_3CH_2$— | o-$PhCH_2OPh$— |
| 15020 | $PhCH_2$— | p-MeOPh— |
| 15021 | $(CH_3)_3C$— | m-MeOPh— |
| 15022 | $PhCH_2$— | Ph |
| 15023 | $PhCH_2$— | p-$CH_3Ph$— |
| 15024 | $(CH_3)_3C$— | p-ClPh— |
| 15025 | $(CH_3)_3C$— | 3-Indolyl- |
| 15026 | 9-Fluorenylmethyl- | 3-Indolyl- |
| 15027 | $(CH_3)_3C$— | 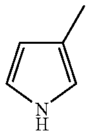 |
| 15028 | 9-Fluorenylmethyl- | 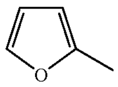 |
| 15029 | $(CH_3)_3C$— | 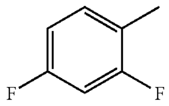 |
| 15030 | $PhCH_2$— | 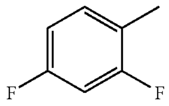 |

TABLE 15-continued

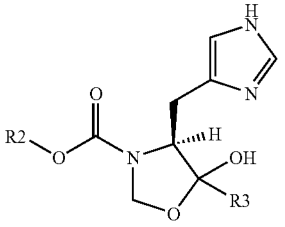

| Example Compound No. | R2— | R3— |
|---|---|---|
| 15031 | $(CH3)_2CH$— | 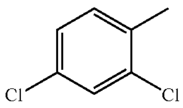 |

TABLE 16

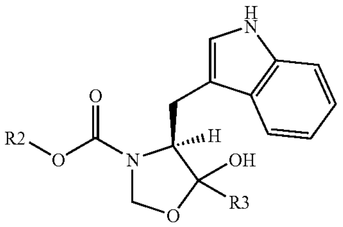

| Example Compound No. | R2— | R3— |
|---|---|---|
| 16001 | $PhCH_2$— | p-$PhCH_2OPh$— |
| 16002 | $CH_3$— | p-$PhCH_2OPh$— |
| 16003 | 9-Fluorenylmethyl- | p-$PhCH_2OPh$— |
| 16004 | $(CH_3)_3C$— | o-$PhCH_2OPh$— |
| 16005 | $CH_3$— | m-$PhCH_2OPh$— |
| 16006 | $PhCH_2$— | p-$NO_2Ph$— |
| 16007 | $(CH_3)_3C$— | p-MeOPh— |
| 16008 | $PhCH_2$— | p-HOPh— |
| 16009 | $(CH_3)_3C$— | Ph— |
| 16010 | $PhCH_2$— | p-FPh |
| 16011 | $PhCH_2$— | 3-Indolyl- |
| 16012 | $CH_3$— | 3-Indolyl- |
| 16013 | $PhCH_2$— | 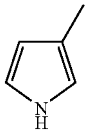 |
| 16014 | $PhCH_2$— | 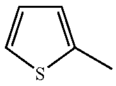 |
| 16015 | $(CH_3)_3C$— | p-$PhCH_2OPh$— |
| 16016 | $CH_3CH_2$— | p-$PhCH_2OPh$— |
| 16017 | $PhCH_2$— | o-$PhCH_2OPh$— |
| 16018 | $(CH_3)_3C$— | m-$PhCH_2OPh$— |
| 16019 | $CH_3CH_2$— | o-$PhCH_2OPh$— |
| 16020 | $PhCH_2$— | p-MeOPh— |
| 16021 | $(CH_3)_3C$— | m-MeOPh— |
| 16022 | $PhCH_2$— | Ph |
| 16023 | $PhCH_2$— | p-$CH_3Ph$— |
| 16024 | $(CH_3)_3C$— | p-ClPh— |
| 16025 | $(CH_3)_3C$— | 3-Indolyl- |
| 16026 | 9-Fluorenylmethyl- | 3-Indolyl- |

TABLE 16-continued

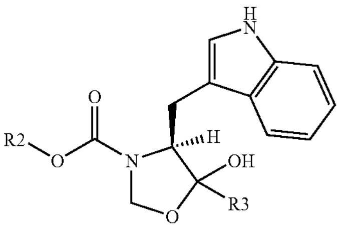

| Example Compound No. | R2— | R3— |
|---|---|---|
| 16027 | $(CH_3)_3C$— | 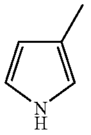 |
| 16028 | 9-Fluorenylmethyl- | 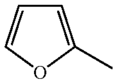 |
| 16029 | $(CH_3)_3C$— | 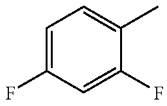 |
| 16030 | $PhCH_2$— | 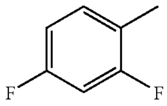 |
| 16031 | $(CH3)_2CH$— | 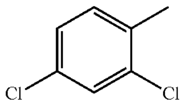 |

TABLE 17

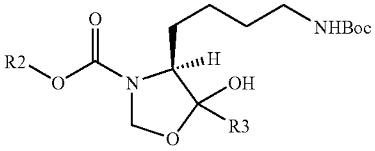

| Example Compound No. | R2— | R3— |
|---|---|---|
| 17001 | $PhCH_2$— | p-$PhCH_2OPh$— |
| 17002 | $CH_3$— | p-$PhCH_2OPh$— |
| 17003 | 9-Fluorenylmethyl- | p-$PhCH_2OPh$— |
| 17004 | $(CH_3)_3C$— | o-$PhCH_2OPh$— |
| 17005 | $CH_3$— | m-$PhCH_2OPh$— |
| 17006 | $PhCH_2$— | p-$NO_2Ph$— |
| 17007 | $(CH_3)_3C$— | p-MeOPh— |
| 17008 | $PhCH_2$— | p-HOPh— |
| 17009 | $(CH_3)_3C$— | Ph— |
| 17010 | $PhCH_2$— | p-FPh |
| 17011 | $PhCH_2$— | 3-Indolyl- |
| 17012 | $CH_3$— | 3-Indolyl- |
| 17013 | $PhCH_2$— | 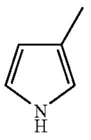 |

TABLE 17-continued

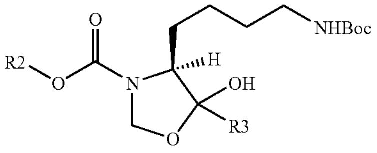

| Example Compound No. | R2— | R3— |
|---|---|---|
| 17014 | $PhCH_2$— | 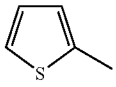 |
| 17015 | $(CH_3)_3C$— | p-$PhCH_2OPh$— |
| 17016 | $CH_3CH_2$— | p-$PhCH_2OPh$— |
| 17017 | $PhCH_2$— | o-$PhCH_2OPh$— |
| 17018 | $(CH_3)_3C$— | m-$PhCH_2OPh$— |
| 17019 | $CH_3CH_2$— | o-$PhCH_2OPh$— |
| 17020 | $PhCH_2$— | p-MeOPh— |
| 17021 | $(CH_3)_3C$— | m-MeOPh— |
| 17022 | $PhCH_2$— | Ph |
| 17023 | $PhCH_2$— | p-$CH_3Ph$— |
| 17024 | $(CH_3)_3C$— | p-ClPh— |
| 17025 | $(CH_3)_3C$— | 3-Indolyl- |
| 17026 | 9-Fluorenylmethyl- | 3-Indolyl- |
| 17027 | $(CH_3)_3C$— | 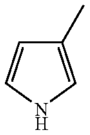 |
| 17028 | 9-Fluorenylmethyl- | 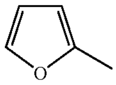 |
| 17029 | $(CH_3)_3C$— | 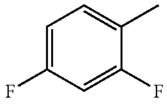 |
| 17030 | $PhCH_2$— | 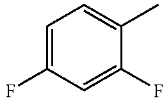 |
| 17031 | $(CH3)_2CH$— | 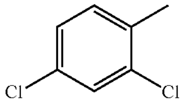 |

TABLE 18

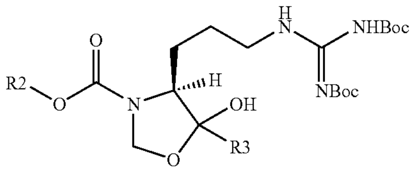

| Example Compound No. | R2— | R3— |
|---|---|---|
| 18001 | $PhCH_2$— | p-$PhCH_2OPh$— |
| 18002 | $CH_3$— | p-$PhCH_2OPh$— |
| 18003 | 9-Fluorenylmethyl- | p-$PhCH_2OPh$— |

TABLE 18-continued

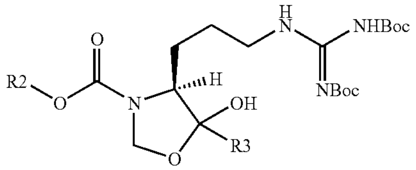

| Example Compound No. | R2— | R3— |
|---|---|---|
| 18004 | $(CH_3)_3C$— | o-$PhCH_2OPh$— |
| 18005 | $CH_3$— | m-$PhCH_2OPh$— |
| 18006 | $PhCH_2$— | p-$NO_2Ph$— |
| 18007 | $(CH_3)_3C$— | p-MeOPh— |
| 18008 | $PhCH_2$— | p-HOPh— |
| 18009 | $(CH_3)_3C$— | Ph— |
| 18010 | $PhCH_2$— | p-FPh |
| 18011 | $PhCH_2$— | 3-Indolyl- |
| 18012 | $CH_3$— | 3-Indolyl- |
| 18013 | $PhCH_2$— | 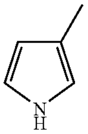 |
| 18014 | $PhCH_2$— | 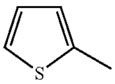 |
| 18015 | $(CH_3)_3C$— | p-$PhCH_2OPh$— |
| 18016 | $CH_3CH_2$— | p-$PhCH_2OPh$— |
| 18017 | $PhCH_2$— | o-$PhCH_2OPh$— |
| 18018 | $(CH_3)_3C$— | m-$PhCH_2OPh$— |
| 18019 | $CH_3CH_2$— | o-$PhCH_2OPh$— |
| 18020 | $PhCH_2$— | p-MeOPh— |
| 18021 | $(CH_3)_3C$— | m-MeOPh— |
| 18022 | $PhCH_2$— | Ph |
| 18023 | $PhCH_2$— | p-$CH_3Ph$— |
| 18024 | $(CH_3)_3C$— | p-ClPh— |
| 18025 | $(CH_3)_3C$— | 3-Indolyl- |
| 18026 | 9-Fluorenylmethyl- | 3-Indolyl- |
| 18027 | $(CH_3)_3C$— | 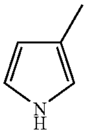 |
| 18028 | 9-Fluorenylmethyl- | 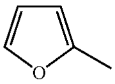 |
| 18029 | $(CH_3)_3C$— | 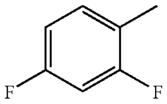 |
| 18030 | $PhCH_2$— | 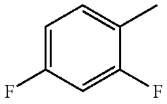 |
| 18031 | $(CH3)_2CH$— | 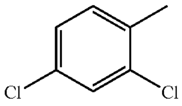 |

TABLE 19

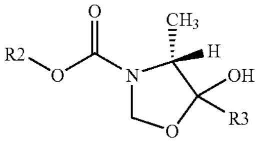

| Example Compound No. | R2— | R3— |
|---|---|---|
| 19001 | $PhCH_2$— | p-$PhCH_2OPh$— |
| 19002 | $CH_3$— | p-$PhCH_2OPh$— |
| 19003 | 9-Fluorenylmethyl- | p-$PhCH_2OPh$— |
| 19004 | $(CH_3)_3C$— | o-$PhCH_2OPh$— |
| 19005 | $CH_3$— | m-$PhCH_2OPh$— |
| 19006 | $PhCH_2$— | p-$NO_2Ph$— |
| 19007 | $(CH_3)_3C$— | p-MeOPh— |
| 19008 | $PhCH_2$— | p-HOPh— |
| 19009 | $(CH_3)_3C$— | Ph— |
| 19010 | $PhCH_2$— | p-FPh |
| 19011 | $PhCH_2$— | 3-Indolyl- |
| 19012 | $CH_3$— | 3-Indolyl- |
| 19013 | $PhCH_2$— | 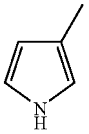 |
| 19014 | $PhCH_2$— | 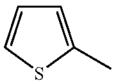 |
| 19015 | $(CH_3)_3C$— | p-$PhCH_2OPh$— |
| 19016 | $CH_3CH_2$— | p-$PhCH_2OPh$— |
| 19017 | $PhCH_2$— | o-$PhCH_2OPh$— |
| 19018 | $(CH_3)_3C$— | m-$PhCH_2OPh$— |
| 19019 | $CH_3CH_2$— | o-$PhCH_2OPh$— |
| 19020 | $PhCH_2$— | p-MeOPh— |
| 19021 | $(CH_3)_3C$— | m-MeOPh— |
| 19022 | $PhCH_2$— | Ph |
| 19023 | $PhCH_2$— | p-$CH_3Ph$— |
| 19024 | $(CH_3)_3C$— | p-ClPh— |
| 19025 | $(CH_3)_3C$— | 3-Indolyl- |
| 19026 | 9-Fluorenylmethyl- | 3-Indolyl- |
| 19027 | $(CH_3)_3C$— | 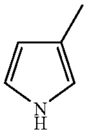 |
| 19028 | 9-Fluorenylmethyl- | 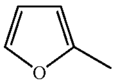 |
| 19029 | $(CH_3)_3C$— | 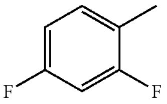 |
| 19030 | $PhCH_2$— | 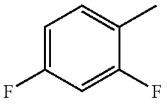 |
| 19031 | $(CH3)_2CH$— | 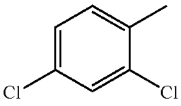 |

TABLE 20

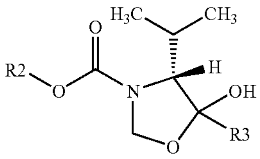

| Example Compound No. | R2— | R3— |
|---|---|---|
| 20001 | $PhCH_2$— | p-$PhCH_2OPh$— |
| 20002 | $CH_3$— | p-$PhCH_2OPh$— |
| 20003 | 9-Fluorenylmethyl- | p-$PhCH_2OPh$— |
| 20004 | $(CH_3)_3C$— | o-$PhCH_2OPh$— |
| 20005 | $CH_3$— | m-$PhCH_2OPh$— |
| 20006 | $PhCH_2$— | p-$NO_2Ph$— |
| 20007 | $(CH_3)_3C$— | p-MeOPh— |
| 20008 | $PhCH_2$— | p-HOPh— |
| 20009 | $(CH_3)_3C$— | Ph— |
| 20010 | $PhCH_2$— | p-FPh |
| 20011 | $PhCH_2$— | 3-Indolyl- |
| 20012 | $CH_3$— | 3-Indolyl- |
| 20013 | $PhCH_2$— | 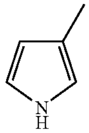 |
| 20014 | $PhCH_2$— | 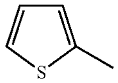 |
| 20015 | $(CH_3)_3C$— | p-$PhCH_2OPh$— |
| 20016 | $CH_3CH_2$— | p-$PhCH_2OPh$— |
| 20017 | $PhCH_2$— | o-$PhCH_2OPh$— |
| 20018 | $(CH_3)_3C$— | m-$PhCH_2OPh$— |
| 20019 | $CH_3CH_2$— | o-$PhCH_2OPh$— |
| 20020 | $PhCH_2$— | p-MeOPh— |
| 20021 | $(CH_3)_3C$— | m-MeOPh— |
| 20022 | $PhCH_2$— | Ph |
| 20023 | $PhCH_2$— | p-$CH_3Ph$— |
| 20024 | $(CH_3)_3C$— | p-ClPh— |
| 20025 | $(CH_3)_3C$— | 3-Indolyl- |
| 20026 | 9-Fluorenylmethyl- | 3-Indolyl- |
| 20027 | $(CH_3)_3C$— | 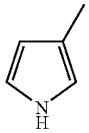 |
| 20028 | 9-Fluorenylmethyl- | 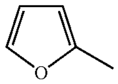 |
| 20029 | $(CH_3)_3C$— | 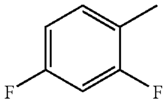 |
| 20030 | $PhCH_2$— | 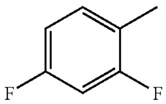 |
| 20031 | $(CH3)_2CH$— | 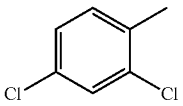 |

TABLE 21

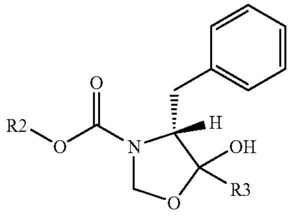

| Example Compound No. | R2— | R3— |
|---|---|---|
| 21001 | $PhCH_2$— | p-$PhCH_2OPh$— |
| 21002 | $CH_3$— | p-$PhCH_2OPh$— |
| 21003 | 9-Fluorenylmethyl- | p-$PhCH_2OPh$— |
| 21004 | $(CH_3)_3C$— | o-$PhCH_2OPh$— |
| 21005 | $CH_3$— | m-$PhCH_2OPh$— |
| 21006 | $PhCH_2$— | p-$NO_2Ph$— |
| 21007 | $(CH_3)_3C$— | p-MeOPh— |
| 21008 | $PhCH_2$— | p-HOPh— |
| 21009 | $(CH_3)_3C$— | Ph— |
| 21010 | $PhCH_2$— | p-FPh |
| 21011 | $PhCH_2$— | 3-Indolyl- |
| 21012 | $CH_3$— | 3-Indolyl- |
| 21013 | $PhCH_2$— | 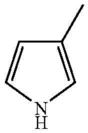 |
| 21014 | $PhCH_2$— | 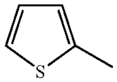 |
| 21015 | $(CH_3)_3C$— | p-$PhCH_2OPh$— |
| 21016 | $CH_3CH_2$— | p-$PhCH_2OPh$— |
| 21017 | $PhCH_2$— | o-$PhCH_2OPh$— |
| 21018 | $(CH_3)_3C$— | m-$PhCH_2OPh$— |
| 21019 | $CH_3CH_2$— | o-$PhCH_2OPh$— |
| 21020 | $PhCH_2$— | p-MeOPh— |
| 21021 | $(CH_3)_3C$— | m-MeOPh— |
| 21022 | $PhCH_2$— | Ph |
| 21023 | $PhCH_2$— | p-$CH_3Ph$— |
| 21024 | $(CH_3)_3C$— | p-ClPh— |
| 21025 | $(CH_3)_3C$— | 3-Indolyl- |
| 21026 | 9-Fluorenylmethyl- | 3-Indolyl- |
| 21027 | $(CH_3)_3C$— | 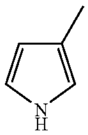 |
| 21028 | 9-Fluorenylmethyl- | 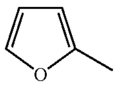 |
| 21029 | $(CH_3)_3C$— | 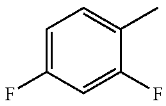 |
| 21030 | $PhCH_2$— | 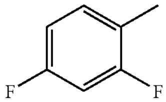 |

TABLE 21-continued

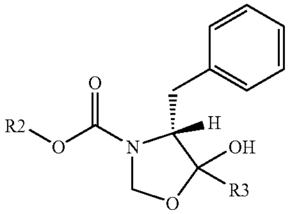

| Example Compound No. | R2— | R3— |
|---|---|---|
| 21031 | $(CH3)_2CH$— | 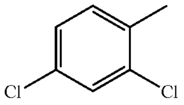 |

TABLE 22

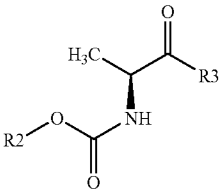

| Example Compound No. | R2— | R3— |
|---|---|---|
| 22001 | $PhCH_2$— | p-$PhCH_2OPh$— |
| 22002 | $CH_3$— | p-$PhCH_2OPh$— |
| 22003 | 9-Fluorenylmethyl- | p-$PhCH_2OPh$— |
| 22004 | $(CH_3)_3C$— | o-$PhCH_2OPh$— |
| 22005 | $CH_3$— | m-$PhCH_2OPh$— |
| 22006 | $PhCH_2$— | p-$NO_2Ph$— |
| 22007 | $(CH_3)_3C$— | p-MeOPh— |
| 22008 | $PhCH_2$— | p-HOPh— |
| 22009 | $(CH_3)_3C$— | Ph— |
| 22010 | $PhCH_2$— | p-FPh |
| 22011 | $PhCH_2$— | 3-Indolyl- |
| 22012 | $CH_3$— | 3-Indolyl- |
| 22013 | $PhCH_2$— | 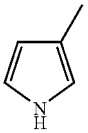 |
| 22014 | $PhCH_2$— | 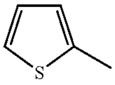 |
| 22015 | H— | p-$PhCH_2OPh$— |
| 22016 | $CH_3CH_2$— | p-$PhCH_2OPh$— |
| 22017 | $PhCH_2$— | o-$PhCH_2OPh$— |
| 22018 | $(CH_3)_3C$— | m-$PhCH_2OPh$— |
| 22019 | $CH_3CH_2$— | o-$PhCH_2OPh$— |
| 22020 | $PhCH_2$— | p-MeOPh— |
| 22021 | $(CH_3)_3C$— | m-MeOPh— |
| 22022 | $PhCH_2$— | Ph |
| 22023 | $PhCH_2$— | p-$CH_3Ph$— |
| 22024 | $(CH_3)_3C$— | p-ClPh— |
| 22025 | $(CH_3)_3C$— | 3-Indolyl- |
| 22026 | 9-Fluorenylmethyl- | 3-Indolyl- |

TABLE 22-continued

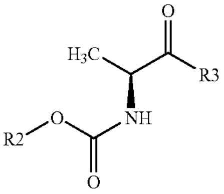

| Example Compound No. | R2— | R3— |
|---|---|---|
| 22027 | $(CH_3)_3C$— | 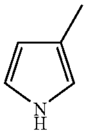 |
| 22028 | 9-Fluorenylmethyl- | 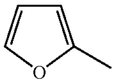 |
| 22029 | $(CH_3)_3C$— | 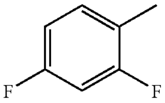 |
| 22030 | $PhCH_2$— | 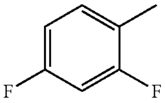 |
| 22031 | $(CH3)_2CH$— | 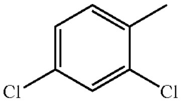 |

TABLE 23

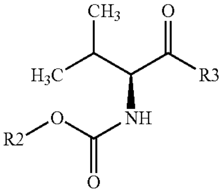

| Example Compound No. | R2— | R3— |
|---|---|---|
| 23001 | $PhCH_2$— | p-$PhCH_2OPh$— |
| 23002 | $CH_3$— | p-$PhCH_2OPh$— |
| 23003 | 9-Fluorenylmethyl- | p-$PhCH_2OPh$— |
| 23004 | $(CH_3)_3C$— | o-$PhCH_2OPh$— |
| 23005 | $CH_3$— | m-$PhCH_2OPh$— |
| 23006 | $PhCH_2$— | p-$NO_2Ph$— |
| 23007 | $(CH_3)_3C$— | p-MeOPh— |
| 23008 | $PhCH_2$— | p-HOPh— |
| 23009 | $(CH_3)_3C$— | Ph— |
| 23010 | $PhCH_2$— | p-FPh |

TABLE 23-continued

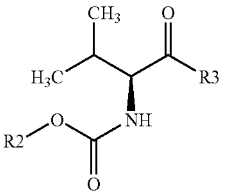

| Example Compound No. | R2— | R3— |
|---|---|---|
| 23011 | $PhCH_2$— | 3-Indolyl- |
| 23012 | $CH_3$— | 3-Indolyl- |
| 23013 | $PhCH_2$— | 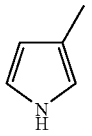 |
| 23014 | $PhCH_2$— | 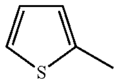 |
| 23015 | H— | p-$PhCH_2OPh$— |
| 23016 | $CH_3CH_2$— | p-$PhCH_2OPh$— |
| 23017 | $PhCH_2$— | o-$PhCH_2OPh$— |
| 23018 | $(CH_3)_3C$— | m-$PhCH_2OPh$— |
| 23019 | $CH_3CH_2$— | o-$PhCH_2OPh$— |
| 23020 | $PhCH_2$— | p-MeOPh— |
| 23021 | $(CH_3)_3C$— | m-MeOPh— |
| 23022 | $PhCH_2$— | Ph |
| 23023 | $PhCH_2$— | p-$CH_3Ph$— |
| 23024 | $(CH_3)_3C$— | p-ClPh— |
| 23025 | $(CH_3)_3C$— | 3-Indolyl- |
| 23026 | 9-Fluorenylmethyl- | 3-Indolyl- |
| 23027 | $(CH_3)_3C$— | 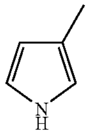 |
| 23028 | 9-Fluorenylmethyl- | 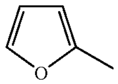 |
| 23029 | $(CH_3)_3C$— | 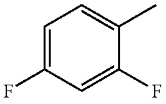 |
| 23030 | $PhCH_2$— | 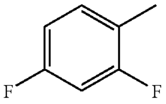 |
| 23031 | $(CH3)_2CH$— | 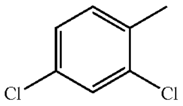 |

TABLE 24

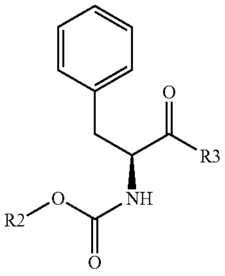

| Example Compound No. | R2— | R3— |
|---|---|---|
| 24001 | $PhCH_2$— | p-$PhCH_2OPh$— |
| 24002 | $CH_3$— | p-$PhCH_2OPh$— |
| 24003 | 9-Fluorenylmethyl- | p-$PhCH_2OPh$— |
| 24004 | $(CH_3)_3C$— | o-$PhCH_2OPh$— |
| 24005 | $CH_3$— | m-$PhCH_2OPh$— |
| 24006 | $PhCH_2$— | p-$NO_2Ph$— |
| 24007 | $(CH_3)_3C$— | p-MeOPh— |
| 24008 | $PhCH_2$— | p-HOPh— |
| 24009 | $(CH_3)_3C$— | Ph— |
| 24010 | $PhCH_2$— | p-FPh |
| 24011 | $PhCH_2$— | 3-Indolyl- |
| 24012 | $CH_3$— | 3-Indolyl- |
| 24013 | $PhCH_2$— | 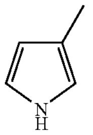 |
| 24014 | $PhCH_2$— | 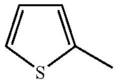 |
| 24015 | H— | p-$PhCH_2OPh$— |
| 24016 | $CH_3CH_2$— | p-$PhCH_2OPh$— |
| 24017 | $PhCH_2$— | o-$PhCH_2OPh$— |
| 24018 | $(CH_3)_3C$— | m-$PhCH_2OPh$— |
| 24019 | $CH_3CH_2$— | o-$PhCH_2OPh$— |
| 24020 | $PhCH_2$— | p-MeOPh— |
| 24021 | $(CH_3)_3C$— | m-MeOPh— |
| 24022 | $PhCH_2$— | Ph |
| 24023 | $PhCH_2$— | p-$CH_3Ph$— |
| 24024 | $(CH_3)_3C$— | p-ClPh— |
| 24025 | $(CH_3)_3C$— | 3-Indolyl- |
| 24026 | 9-Fluorenylmethyl- | 3-Indolyl- |
| 24027 | $(CH_3)_3C$— | 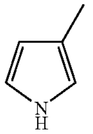 |
| 24028 | 9-Fluorenylmethyl- | 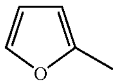 |
| 24029 | $(CH_3)_3C$— | 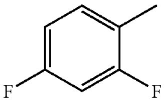 |
| 24030 | $PhCH_2$— | 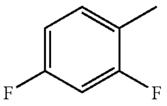 |

TABLE 24-continued

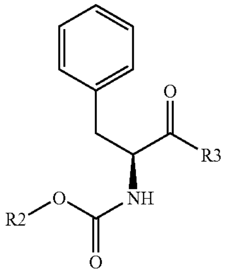

| Example Compound No. | R2— | R3— |
|---|---|---|
| 24031 | (CH3)$_2$CH— | 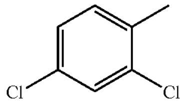 |

TABLE 25

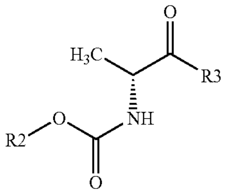

| Example Compound No. | R2— | R3— |
|---|---|---|
| 25001 | $PhCH_2$— | p-$PhCH_2OPh$— |
| 25002 | $CH_3$— | p-$PhCH_2OPh$— |
| 25003 | 9-Fluorenylmethyl- | p-$PhCH_2OPh$— |
| 25004 | $(CH_3)_3C$— | o-$PhCH_2OPh$— |
| 25005 | $CH_3$— | m-$PhCH_2OPh$— |
| 25006 | $PhCH_2$— | p-$NO_2Ph$— |
| 25007 | $(CH_3)_3C$— | p-MeOPh— |
| 25008 | $PhCH_2$— | p-HOPh— |
| 25009 | $(CH_3)_3C$— | Ph— |
| 25010 | $PhCH_2$— | p-FPh |
| 25011 | $PhCH_2$— | 3-Indolyl- |
| 25012 | $CH_3$— | 3-Indolyl- |
| 25013 | $PhCH_2$— | 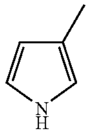 |
| 25014 | $PhCH_2$— | 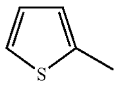 |
| 25015 | H— | p-$PhCH_2OPh$— |
| 25016 | $CH_3CH_2$— | p-$PhCH_2OPh$— |
| 25017 | $PhCH_2$— | o-$PhCH_2OPh$— |
| 25018 | $(CH_3)_3C$— | m-$PhCH_2OPh$— |
| 25019 | $CH_3CH_2$— | o-$PhCH_2OPh$— |
| 25020 | $PhCH_2$— | p-MeOPh— |
| 25021 | $(CH_3)_3C$— | m-MeOPh— |
| 25022 | $PhCH_2$— | Ph |
| 25023 | $PhCH_2$— | p-$CH_3Ph$— |
| 25024 | $(CH_3)_3C$— | p-ClPh— |
| 25025 | $(CH_3)_3C$— | 3-Indolyl- |
| 25026 | 9-Fluorenylmethyl- | 3-Indolyl- |

TABLE 25-continued

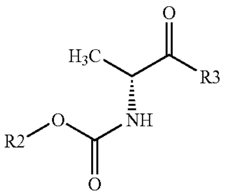

| Example Compound No. | R2— | R3— |
|---|---|---|
| 25027 | $(CH_3)_3C$— | 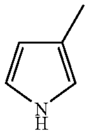 |
| 25028 | 9-Fluorenylmethyl- | 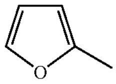 |
| 25029 | $(CH_3)_3C$— | 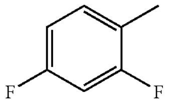 |
| 25030 | $PhCH_2$— | 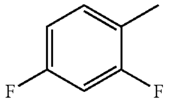 |
| 25031 | (CH3)$_2$CH— | 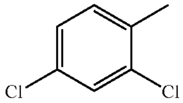 |

TABLE 26

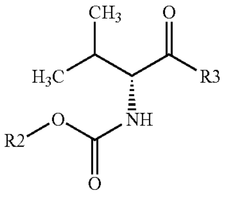

| Example Compound No. | R2— | R3— |
|---|---|---|
| 26001 | $PhCH_2$— | p-$PhCH_2OPh$— |
| 26002 | $CH_3$— | p-$PhCH_2OPh$— |
| 26003 | 9-Fluorenylmethyl- | p-$PhCH_2OPh$— |
| 26004 | $(CH_3)_3C$— | o-$PhCH_2OPh$— |
| 26005 | $CH_3$— | m-$PhCH_2OPh$— |
| 26006 | $PhCH_2$— | p-$NO_2Ph$— |
| 26007 | $(CH_3)_3C$— | p-MeOPh— |
| 26008 | $PhCH_2$— | p-HOPh— |
| 26009 | $(CH_3)_3C$— | Ph— |
| 26010 | $PhCH_2$— | p-FPh |
| 26011 | $PhCH_2$— | 3-Indolyl- |

TABLE 26-continued

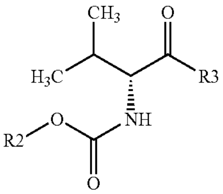

| Example Compound No. | R2— | R3— |
|---|---|---|
| 26012 | $CH_3$— | 3-Indolyl- |
| 26013 | $PhCH_2$— | 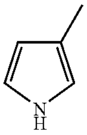 |
| 26014 | $PhCH_2$— | 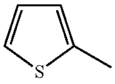 |
| 26015 | H— | p-$PhCH_2OPh$— |
| 26016 | $CH_3CH_2$— | p-$PhCH_2OPh$— |
| 26017 | $PhCH_2$— | o-$PhCH_2OPh$— |
| 26018 | $(CH_3)_3C$— | m-$PhCH_2OPh$— |
| 26019 | $CH_3CH_2$— | o-$PhCH_2OPh$— |
| 26020 | $PhCH_2$— | p-MeOPh— |
| 26021 | $(CH_3)_3C$— | m-MeOPh— |
| 26022 | $PhCH_2$— | Ph |
| 26023 | $PhCH_2$— | p-$CH_3Ph$— |
| 26024 | $(CH_3)_3C$— | p-ClPh— |
| 26025 | $(CH_3)_3C$— | 3-Indolyl- |
| 26026 | 9-Fluorenylmethyl- | 3-Indolyl- |
| 26027 | $(CH_3)_3C$— | 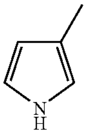 |
| 26028 | 9-Fluorenylmethyl- | 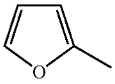 |
| 26029 | $(CH_3)_3C$— | 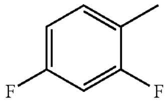 |
| 26030 | $PhCH_2$— | 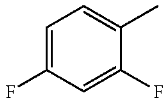 |
| 26031 | $(CH3)_2CH$— | 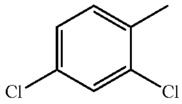 |

TABLE 27

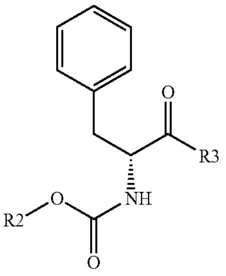

| Example Compound No. | R2— | R3— |
|---|---|---|
| 27001 | $PhCH_2$— | p-$PhCH_2OPh$— |
| 27002 | $CH_3$— | p-$PhCH_2OPh$— |
| 27003 | 9-Fluorenylmethyl- | p-$PhCH_2OPh$— |
| 27004 | $(CH_3)_3C$— | o-$PhCH_2OPh$— |
| 27005 | $CH_3$— | m-$PhCH_2OPh$— |
| 27006 | $PhCH_2$— | p-$NO_2Ph$— |
| 27007 | $(CH_3)_3C$— | p-MeOPh— |
| 27008 | $PhCH_2$— | p-HOPh— |
| 27009 | $(CH_3)_3C$— | Ph— |
| 27010 | $PhCH_2$— | p-FPh |
| 27011 | $PhCH_2$— | 3-Indolyl- |
| 27012 | $CH_3$— | 3-Indolyl- |
| 27013 | $PhCH_2$— | 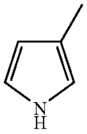 |
| 27014 | $PhCH_2$— | 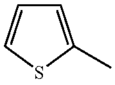 |
| 27015 | H— | p-$PhCH_2OPh$— |
| 27016 | $CH_3CH_2$— | p-$PhCH_2OPh$— |
| 27017 | $PhCH_2$— | o-$PhCH_2OPh$— |
| 27018 | $(CH_3)_3C$— | m-$PhCH_2OPh$— |
| 27019 | $CH_3CH_2$— | o-$PhCH_2OPh$— |
| 27020 | $PhCH_2$— | p-MeOPh— |
| 27021 | $(CH_3)_3C$— | m-MeOPh— |
| 27022 | $PhCH_2$— | Ph |
| 27023 | $PhCH_2$— | p-$CH_3Ph$— |
| 27024 | $(CH_3)_3C$— | p-ClPh— |
| 27025 | $(CH_3)_3C$— | 3-Indolyl- |
| 27026 | 9-Fluorenylmethyl- | 3-Indolyl- |
| 27027 | $(CH_3)_3C$— | 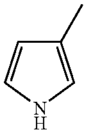 |
| 27028 | 9-Fluorenylmethyl- | 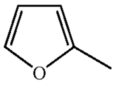 |
| 27029 | $(CH_3)_3C$— | 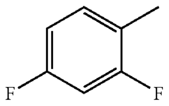 |
| 27030 | $PhCH_2$— | 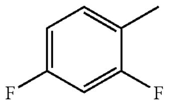 |

TABLE 27-continued

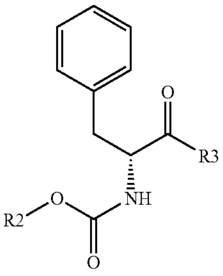

| Example Compound No. | R2— | R3— |
|---|---|---|
| 27031 | $(CH3)_2CH$— | 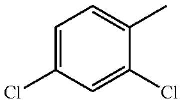 |

TABLE 28

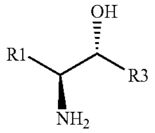

| Example Compound No. | R1— | R3— |
|---|---|---|
| 28001 | $CH_3$— | p-HOPh— |
| 28002 | $CH_3$— | o-HOPh— |
| 28003 | $CH_3$— | m-HOPh— |
| 28004 | $CH_3$— | p-MeOPh— |
| 28005 | $CH_3$— | o-MeOPh— |
| 28006 | $CH_3$— | m-MeOPh— |
| 28007 | $CH_3$— | p-MePh— |
| 28008 | $CH_3$— | p-$(CH_3)_2$NPh— |
| 28009 | $CH_3$— | Ph— |
| 28010 | $CH_3$— | p-FPh |
| 28011 | $CH_3$— | 3-Indolyl- |
| 28012 | $CH_3$— | p-AcNHPh |
| 28013 | $CH_3$— | 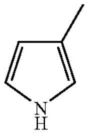 |
| 28014 | $CH_3$— | 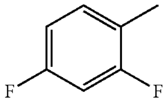 |
| 28015 | $CH_3$— | 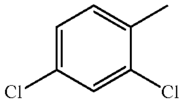 |
| 28016 | $(CH_3)_2CH$— | p-HOPh— |
| 28017 | $(CH_3)_2CH$— | o-HOPh— |
| 28018 | $(CH_3)_2CH$— | m-HOPh— |
| 28019 | $(CH_3)_2CH$— | p-MeOPh— |
| 28020 | $(CH_3)_2CH$— | o-MeOPh— |
| 28021 | $(CH_3)_2CH$— | m-MeOPh— |
| 28022 | $(CH_3)_2CH$— | p-MePh— |
| 28023 | $(CH_3)_2CH$— | p-$(CH_3—)_2$NPh— |
| 28024 | $(CH_3)_2CH$— | Ph— |

TABLE 28-continued

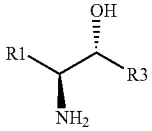

| Example Compound No. | R1— | R3— |
|---|---|---|
| 28025 | $(CH_3)_2CH$— | p-FPh |
| 28026 | $(CH_3)_2CH$— | 3-Indolyl- |
| 28027 | $(CH_3)_2CH$— | p-AcNHPh |
| 28028 | $(CH_3)_2CH$— | 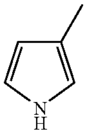 |
| 28029 | $(CH_3)_2CH$— | 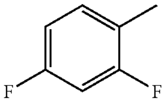 |
| 28030 | $(CH_3)_2CH$— | 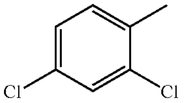 |

TABLE 29

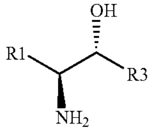

| Example Compound No. | R1— | R3— |
|---|---|---|
| 29001 | $PhCH_2$— | p-HOPh— |
| 29002 | $PhCH_2$— | o-HOPh— |
| 29003 | $PhCH_2$— | m-HOPh— |
| 29004 | $PhCH_2$— | p-MeOPh— |
| 29005 | $PhCH_2$— | o-MeOPh— |
| 29006 | $PhCH_2$— | m-MeOPh— |
| 29007 | $PhCH_2$— | p-MePh— |
| 29008 | $PhCH_2$— | p-$(CH_3)_2$NPh— |
| 29009 | $PhCH_2$— | Ph— |
| 29010 | $PhCH_2$— | p-FPh |
| 29011 | $PhCH_2$— | 3-Indolyl- |
| 29012 | $PhCH_2$— | p-AcNHPh |
| 29013 | $PhCH_2$— | 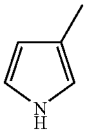 |
| 29014 | $PhCH_2$— | 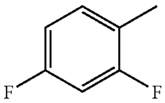 |

TABLE 29-continued

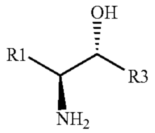

| Example Compound No. | R1— | R3— |
|---|---|---|
| 29015 | $PhCH_2$— | 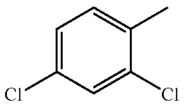 |
| 29016 | $HOCH_2$— | p-HOPh— |
| 29017 | $HOCH_2$— | o-HOPh— |
| 29018 | $HOCH_2$— | m-HOPh— |
| 29019 | $HOCH_2$— | p-MeOPh— |
| 29020 | $HOCH_2$— | o-MeOPh— |
| 29021 | $HOCH_2$— | m-MeOPh— |
| 29022 | $HOCH_2$— | p-MePh— |
| 29023 | $HOCH_2$— | p-$(CH_3)_2$NPh— |
| 29024 | $HOCH_2$— | Ph— |
| 29025 | $HOCH_2$— | p-FPh |
| 29026 | $HOCH_2$— | 3-Indolyl- |
| 29027 | $HOCH_2$— | p-AcNHPh |
| 29028 | $HOCH_2$— | 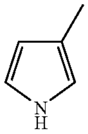 |
| 29029 | $HOCH_2$— | 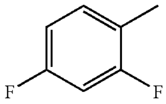 |
| 29030 | $HOCH_2$— | 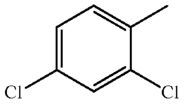 |

TABLE 30

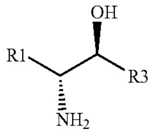

| Example Compound No. | R1— | R3— |
|---|---|---|
| 30001 | $CH_3$— | p-HOPh— |
| 30002 | $CH_3$— | o-HOPh— |
| 30003 | $CH_3$— | m-HOPh— |
| 30004 | $CH_3$— | p-MeOPh— |
| 30005 | $CH_3$— | o-MeOPh— |
| 30006 | $CH_3$— | m-MeOPh— |
| 30007 | $CH_3$— | p-MePh— |
| 30008 | $CH_3$— | p-$(CH_3)_2$NPh— |
| 30009 | $CH_3$— | Ph— |
| 30010 | $CH_3$— | p-FPh |
| 30011 | $CH_3$— | 3-Indolyl- |
| 30012 | $CH_3$— | p-AcNHPh |

TABLE 30-continued

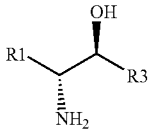

| Example Compound No. | R1— | R3— |
|---|---|---|
| 30013 | $CH_3$— | 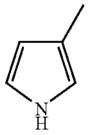 |
| 30014 | $CH_3$— | 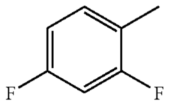 |
| 30015 | $CH_3$— | 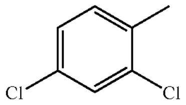 |
| 30016 | $(CH_3)_2CH$— | p-HOPh— |
| 30017 | $(CH_3)_2CH$— | o-HOPh— |
| 30018 | $(CH_3)_2CH$— | m-HOPh— |
| 30019 | $(CH_3)_2CH$— | p-MeOPh— |
| 30020 | $(CH_3)_2CH$— | o-MeOPh— |
| 30021 | $(CH_3)_2CH$— | m-MeOPh— |
| 30022 | $(CH_3)_2CH$— | p-MePh— |
| 30023 | $(CH_3)_2CH$— | p-$(CH_3)_2$NPh— |
| 30024 | $(CH_3)_2CH$— | Ph— |
| 30025 | $(CH_3)_2CH$— | p-FPh |
| 30026 | $(CH_3)_2CH$— | 3-Indolyl- |
| 30027 | $(CH_3)_2CH$— | p-AcNHPh |
| 30028 | $(CH_3)_2CH$— | 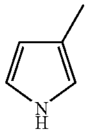 |
| 30029 | $(CH_3)_2CH$— | 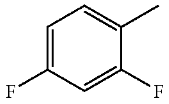 |
| 30030 | $(CH_3)_2CH$— | 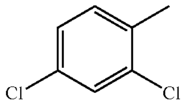 |

TABLE 31

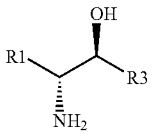

| Example Compound No. | R1— | R3— |
|---|---|---|
| 31001 | $PhCH_2$— | p-HOPh— |
| 31002 | $PhCH_2$— | o-HOPh— |
| 31003 | $PhCH_2$— | m-HOPh— |
| 31004 | $PhCH_2$— | p-MeOPh— |

TABLE 31-continued

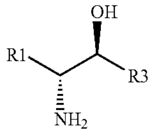

| Example Compound No. | R1— | R3— |
|---|---|---|
| 31005 | $PhCH_2$— | o-MeOPh— |
| 31006 | $PhCH_2$— | m-MeOPh— |
| 31007 | $PhCH_2$— | p-MePh— |
| 31008 | $PhCH_2$— | p-$(CH_3)_2$NPh— |
| 31009 | $PhCH_2$— | Ph— |
| 31010 | $PhCH_2$— | p-FPh |
| 31011 | $PhCH_2$— | 3-Indolyl- |
| 31012 | $PhCH_2$— | p-AcNHPh |
| 31013 | $PhCH_2$— | 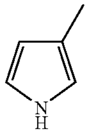 |
| 31014 | $PhCH_2$— | 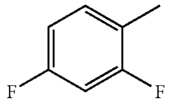 |
| 31015 | $PhCH_2$— | 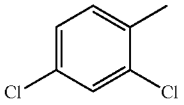 |
| 31016 | $HOCH_2$— | p-HOPh— |
| 31017 | $HOCH_2$— | o-HOPh— |
| 31018 | $HOCH_2$— | m-HOPh— |
| 31019 | $HOCH_2$— | p-MeOPh— |
| 31020 | $HOCH_2$— | o-MeOPh— |
| 31021 | $HOCH_2$— | m-MeOPh— |
| 31022 | $HOCH_2$— | p-MePh— |
| 31023 | $HOCH_2$— | p-$(CH_3)_2$NPh— |
| 31024 | $HOCH_2$— | Ph— |
| 31025 | $HOCH_2$— | p-FPh |
| 31026 | $HOCH_2$— | 3-Indolyl- |
| 31027 | $HOCH_2$— | p-AcNHPh |
| 31028 | $HOCH_2$— | 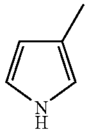 |
| 31029 | $HOCH_2$— | 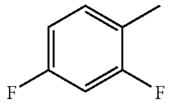 |
| 31030 | $HOCH_2$— | 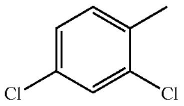 |

TABLE 32

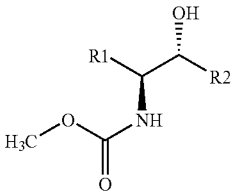

| Example Compound No. | R1— | R3— |
|---|---|---|
| 32001 | $CH_3$— | p-HOPh— |
| 32002 | $CH_3$— | p-$PhCH_2OPh$— |
| 32003 | $CH_3$— | p-$MeOCH_2CH_2OPh$— |
| 32004 | $CH_3$— | p-MeOPh— |
| 32005 | $CH_3$— | o-MeOPh— |
| 32006 | $CH_3$— | m-MeOPh— |
| 32007 | $CH_3$— | p-MePh— |
| 32008 | $CH_3$— | p-$(CH_3)_2$NPh— |
| 32009 | $CH_3$— | Ph— |
| 32010 | $CH_3$— | p-FPh |
| 32011 | $CH_3$— | 3-Indolyl- |
| 32012 | $CH_3$— | p-AcNHPh |
| 32013 | $CH_3$— | 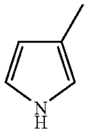 |
| 32014 | $CH_3$— | 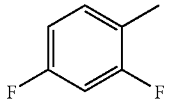 |
| 32015 | $CH_3$— | 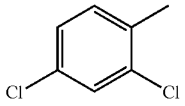 |
| 32016 | $(CH_3)_2CH$— | p-HOPh— |
| 32017 | $(CH_3)_2CH$— | p-$PhCH_2OPh$— |
| 32018 | $(CH_3)_2CH$— | p-$MeOCH_2CH_2OPh$— |
| 32019 | $(CH_3)_2CH$— | p-MeOPh— |
| 32020 | $(CH_3)_2CH$— | o-MeOPh— |
| 32021 | $(CH_3)_2CH$— | m-MeOPh— |
| 32022 | $(CH_3)_2CH$— | p-MePh— |
| 32023 | $(CH_3)_2CH$— | p-$(CH_3)_2$NPh— |
| 32024 | $(CH_3)_2CH$— | Ph— |
| 32025 | $(CH_3)_2CH$— | p-FPh |
| 32026 | $(CH_3)_2CH$— | 3-Indolyl- |
| 32027 | $(CH_3)_2CH$— | p-AcNHPh |
| 32028 | $(CH_3)_2CH$— | 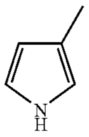 |
| 32029 | $(CH_3)_2CH$— | 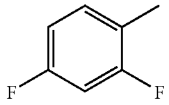 |
| 32030 | $(CH_3)_2CH$— | 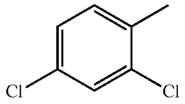 |

TABLE 33

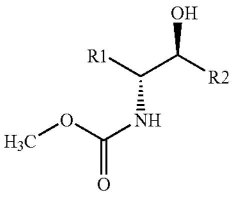

| Example Compound No. | R1— | R3— |
|---|---|---|
| 33001 | $PhCH_2$— | p-HOPh— |
| 33002 | $PhCH_2$— | p-$PhCH_2OPh$— |
| 33003 | $PhCH_2$— | p-$MeOCH_2CH_2OPh$— |
| 33004 | $PhCH_2$— | p-MeOPh— |
| 33005 | $PhCH_2$— | o-MeOPh— |
| 33006 | $PhCH_2$— | m-MeOPh— |
| 33007 | $PhCH_2$— | p-MePh— |
| 33008 | $PhCH_2$— | p-$(CH_3)_2NPh$— |
| 33009 | $PhCH_2$— | Ph— |
| 33010 | $PhCH_2$— | p-FPh |
| 33011 | $PhCH_2$— | 3-Indolyl- |
| 33012 | $PhCH_2$— | p-AcNHPh |
| 33013 | $PhCH_2$— | 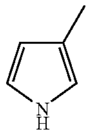 |
| 33014 | $PhCH_2$— | 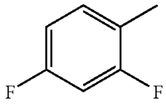 |
| 33015 | $PhCH_2$— | 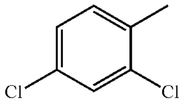 |
| 33016 | $HOCH_2$— | p-HOPh— |
| 33017 | $HOCH_2$— | p-$PhCH_2OPh$— |
| 33018 | $HOCH_2$— | p-$MeOCH_2CH_2OPh$— |
| 33019 | $HOCH_2$— | p-MeOPh— |
| 33020 | $HOCH_2$— | o-MeOPh— |
| 33021 | $HOCH_2$— | m-MeOPh— |
| 33022 | $HOCH_2$— | p-MePh— |
| 33023 | $HOCH_2$— | p-$(CH_3)_2NPh$— |
| 33024 | $HOCH_2$— | Ph— |
| 33025 | $HOCH_2$— | p-FPh |
| 33026 | $HOCH_2$— | 3-Indolyl- |
| 33027 | $HOCH_2$— | p-AcNHPh |
| 33028 | $HOCH_2$— | 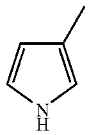 |
| 33029 | $HOCH_2$— | 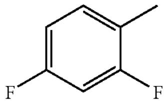 |
| 33030 | $HOCH_2$— | 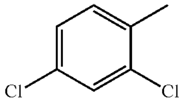 |

TABLE 34

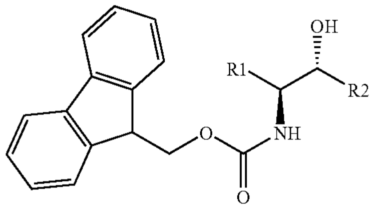

| Example Compound No. | R1— | R3— |
|---|---|---|
| 34001 | $CH_3$— | p-HOPh— |
| 34002 | $CH_3$— | p-$PhCH_2OPh$— |
| 34003 | $CH_3$— | p-$MeOCH_2CH_2OPh$— |
| 34004 | $CH_3$— | p-MeOPh— |
| 34005 | $CH_3$— | o-MeOPh— |
| 34006 | $CH_3$— | m-MeOPh— |
| 34007 | $CH_3$— | p-MePh— |
| 34008 | $CH_3$— | p-$(CH_3)_2NPh$— |
| 34009 | $CH_3$— | Ph— |
| 34010 | $CH_3$— | p-FPh |
| 34011 | $CH_3$— | 3-Indolyl- |
| 34012 | $CH_3$— | p-AcNHPh |
| 34013 | $CH_3$— | 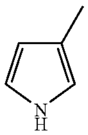 |
| 34014 | $CH_3$— | 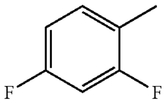 |
| 34015 | $CH_3$— | 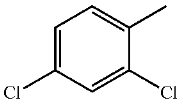 |
| 34016 | $(CH_3)_2CH$— | p-HOPh— |
| 34017 | $(CH_3)_2CH$— | p-$PhCH_2OPh$— |
| 34018 | $(CH_3)_2CH$— | p-$MeOCH_2CH_2OPh$— |
| 34019 | $(CH_3)_2CH$— | p-MeOPh— |
| 34020 | $(CH_3)_2CH$— | o-MeOPh— |
| 34021 | $(CH_3)_2CH$— | m-MeOPh— |
| 34022 | $(CH_3)_2CH$— | p-MePh— |
| 34023 | $(CH_3)_2CH$— | p-$(CH_3)_2NPh$— |
| 34024 | $(CH_3)_2CH$— | Ph— |
| 34025 | $(CH_3)_2CH$— | p-FPh |
| 34026 | $(CH_3)_2CH$— | 3-Indolyl- |
| 34027 | $(CH_3)_2CH$— | p-AcNHPh |
| 34028 | $(CH_3)_2CH$— | 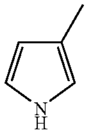 |
| 34029 | $(CH_3)_2CH$— | 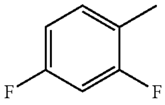 |
| 34030 | $(CH_3)_2CH$— | 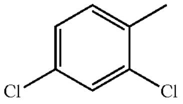 |

TABLE 35

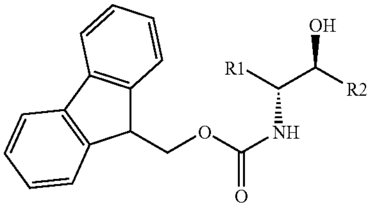

| Example Compound No. | R1— | R3— |
|---|---|---|
| 35001 | $PhCH_2$— | p-HOPh— |
| 35002 | $PhCH_2$— | p-$PhCH_2OPh$— |
| 35003 | $PhCH_2$— | p-$MeOCH_2CH_2OPh$— |
| 35004 | $PhCH_2$— | p-MeOPh— |
| 35005 | $PhCH_2$— | o-MeOPh— |
| 35006 | $PhCH_2$— | m-MeOPh— |
| 35007 | $PhCH_2$— | p-MePh— |
| 35008 | $PhCH_2$— | p-$(CH_3)_2NPh$— |
| 35009 | $PhCH_2$— | Ph— |
| 35010 | $PhCH_2$— | p-FPh |
| 35011 | $PhCH_2$— | 3-Indolyl- |
| 35012 | $PhCH_2$— | p-AcNHPh |
| 35013 | $PhCH_2$— | 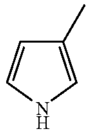 |
| 35014 | $PhCH_2$— | 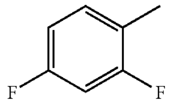 |
| 35015 | $PhCH_2$— | 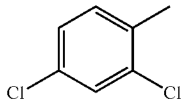 |
| 35016 | $HOCH_2$— | p-HOPh— |
| 35017 | $HOCH_2$— | p-$PhCH_2OPh$— |
| 35018 | $HOCH_2$— | p-$MeOCH_2CH_2OPh$— |
| 35019 | $HOCH_2$— | p-MeOPh— |
| 35020 | $HOCH_2$— | o-MeOPh— |
| 35021 | $HOCH_2$— | m-MeOPh— |
| 35022 | $HOCH_2$— | p-MePh— |
| 35023 | $HOCH_2$— | p-$(CH_3)_2NPh$— |
| 35024 | $HOCH_2$— | Ph— |
| 35025 | $HOCH_2$— | p-FPh |
| 35026 | $HOCH_2$— | 3-Indolyl- |
| 35027 | $HOCH_2$— | p-AcNHPh |
| 35028 | $HOCH_2$— | 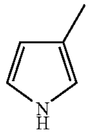 |
| 35029 | $HOCH_2$— | 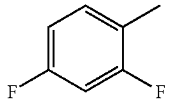 |
| 35030 | $HOCH_2$— | 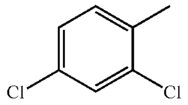 |

TABLE 36

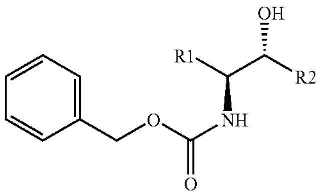

| Example Compound No. | R1— | R3— |
|---|---|---|
| 36001 | $CH_3$— | p-HOPh— |
| 36002 | $CH_3$— | p-$PhCH_2OPh$— |
| 36003 | $CH_3$— | p-$MeOCH_2CH_2OPh$— |
| 36004 | $CH_3$— | p-MeOPh— |
| 36005 | $CH_3$— | o-MeOPh— |
| 36006 | $CH_3$— | m-MeOPh— |
| 36007 | $CH_3$— | p-MePh— |
| 36008 | $CH_3$— | p-$(CH_3)_2NPh$— |
| 36009 | $CH_3$— | Ph— |
| 36010 | $CH_3$— | p-FPh |
| 36011 | $CH_3$— | 3-Indolyl- |
| 36012 | $CH_3$— | p-AcNHPh |
| 36013 | $CH_3$— | 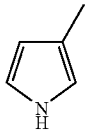 |
| 36014 | $CH_3$— | 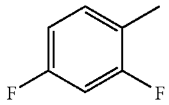 |
| 36015 | $CH_3$— | 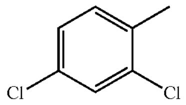 |
| 36016 | $(CH_3)_2CH$— | p-HOPh— |
| 36017 | $(CH_3)_2CH$— | p-$PhCH_2OPh$— |
| 36018 | $(CH_3)_2CH$— | p-$MeOCH_2CH_2OPh$— |
| 36019 | $(CH_3)_2CH$— | p-MeOPh— |
| 36020 | $(CH_3)_2CH$— | o-MeOPh— |
| 36021 | $(CH_3)_2CH$— | m-MeOPh— |
| 36022 | $(CH_3)_2CH$— | p-MePh— |
| 36023 | $(CH_3)_2CH$— | p-$(CH_3)_2NPh$— |
| 36024 | $(CH_3)_2CH$— | Ph— |
| 36025 | $(CH_3)_2CH$— | p-FPh |
| 36026 | $(CH_3)_2CH$— | 3-Indolyl- |
| 36027 | $(CH_3)_2CH$— | p-AcNHPh |
| 36028 | $(CH_3)_2CH$— | 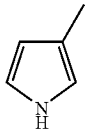 |
| 36029 | $(CH_3)_2CH$— | 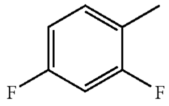 |
| 36030 | $(CH_3)_2CH$— | 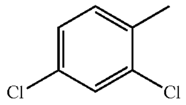 |

TABLE 37

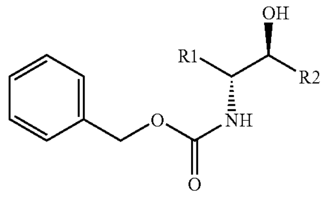

| Example Compound No. | R1— | R3— |
|---|---|---|
| 37001 | $PhCH_2$— | p-HOPh— |
| 37002 | $PhCH_2$— | p-$PhCH_2OPh$— |
| 37003 | $PhCH_2$— | p-$MeOCH_2CH_2OPh$— |
| 37004 | $PhCH_2$— | p-MeOPh— |
| 37005 | $PhCH_2$— | o-MeOPh— |
| 37006 | $PhCH_2$— | m-MeOPh— |
| 37007 | $PhCH_2$— | p-MePh— |
| 37008 | $PhCH_2$— | p-$(CH_3)_2NPh$— |
| 37009 | $PhCH_2$— | Ph— |
| 37010 | $PhCH_2$— | p-FPh |
| 37011 | $PhCH_2$— | 3-Indolyl- |
| 37012 | $PhCH_2$— | p-AcNHPh |
| 37013 | $PhCH_2$— | 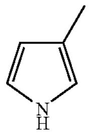 |
| 37014 | $PhCH_2$— | 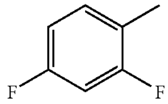 |
| 37015 | $PhCH_2$— | 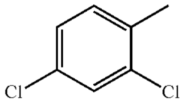 |
| 37016 | $HOCH_2$— | p-HOPh— |
| 37017 | $HOCH_2$— | p-$PhCH_2OPh$— |
| 37018 | $HOCH_2$— | p-$MeOCH_2CH_2OPh$— |
| 37019 | $HOCH_2$— | p-MeOPh— |
| 37020 | $HOCH_2$— | o-MeOPh— |
| 37021 | $HOCH_2$— | m-MeOPh— |
| 37022 | $HOCH_2$— | p-MePh— |
| 37023 | $HOCH_2$— | p-$(CH_3)_2NPh$— |
| 37024 | $HOCH_2$— | Ph— |
| 37025 | $HOCH_2$— | p-FPh |
| 37026 | $HOCH_2$— | 3-Indolyl- |
| 37027 | $HOCH_2$— | p-AcNHPh |
| 37028 | $HOCH_2$— | 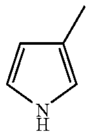 |
| 37029 | $HOCH_2$— | 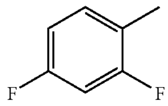 |
| 37030 | $HOCH_2$— | 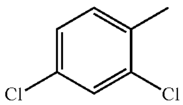 |

TABLE 38

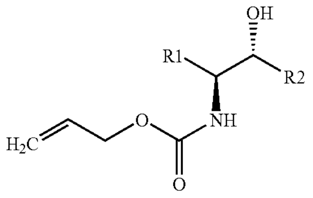

| Example Compound No. | R1— | R3— |
|---|---|---|
| 38001 | $CH_3$— | p-HOPh— |
| 38002 | $CH_3$— | p-$PhCH_2OPh$— |
| 38003 | $CH_3$— | p-$MeOCH_2CH_2OPh$— |
| 38004 | $CH_3$— | p-MeOPh— |
| 38005 | $CH_3$— | o-MeOPh— |
| 38006 | $CH_3$— | m-MeOPh— |
| 38007 | $CH_3$— | p-MePh— |
| 38008 | $CH_3$— | p-$(CH_3)_2NPh$— |
| 38009 | $CH_3$— | Ph— |
| 38010 | $CH_3$— | p-FPh |
| 38011 | $CH_3$— | 3-Indolyl- |
| 38012 | $CH_3$— | p-AcNHPh |
| 38013 | $CH_3$— | 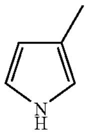 |
| 38014 | $CH_3$— | 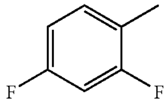 |
| 38015 | $CH_3$— | 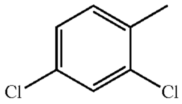 |
| 38016 | $(CH_3)_2CH$— | p-HOPh— |
| 38017 | $(CH_3)_2CH$— | p-$PhCH_2OPh$— |
| 38018 | $(CH_3)_2CH$— | p-$MeOCH_2CH_2OPh$— |
| 38019 | $(CH_3)_2CH$— | p-MeOPh— |
| 38020 | $(CH_3)_2CH$— | o-MeOPh— |
| 38021 | $(CH_3)_2CH$— | m-MeOPh— |
| 38022 | $(CH_3)_2CH$— | p-MePh— |
| 38023 | $(CH_3)_2CH$— | p-$(CH_3)_2NPh$— |
| 38024 | $(CH_3)_2CH$— | Ph— |
| 38025 | $(CH_3)_2CH$— | p-FPh |
| 38026 | $(CH_3)_2CH$— | 3-Indolyl- |
| 38027 | $(CH_3)_2CH$— | p-AcNHPh |
| 38028 | $(CH_3)_2CH$— | 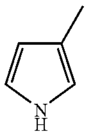 |
| 38029 | $(CH_3)_2CH$— | 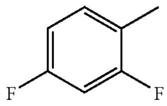 |
| 38030 | $(CH_3)_2CH$— | 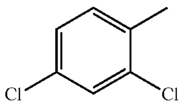 |

TABLE 39

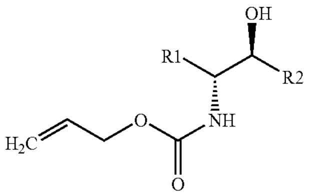

| Example Compound No. | R1— | R3— |
|---|---|---|
| 39001 | $PhCH_2$— | p-HOPh— |
| 39002 | $PhCH_2$— | p-$PhCH_2OPh$— |
| 39003 | $PhOH_2$— | p-$MeOCH_2CH_2OPh$— |
| 39004 | $PhCH_2$— | p-MeOPh— |
| 39005 | $PhCH_2$— | o-MeOPh— |
| 39006 | $PhCH_2$— | m-MeOPh— |
| 39007 | $PhCH_2$— | p-MePh— |
| 39008 | $PhCH_2$— | p-$(CH_3)_2NPh$— |
| 39009 | $PhCH_2$— | Ph— |
| 39010 | $PhCH_2$— | p-FPh |
| 39011 | $PhCH_2$— | 3-Indolyl- |
| 39012 | $PhCH_2$— | p-AcNHPh |
| 39013 | $PhCH_2$— | 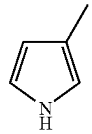 |
| 39014 | $PhCH_2$— | 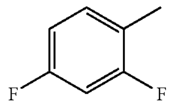 |
| 39015 | $PhCH_2$— | 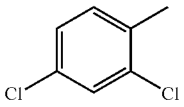 |
| 39016 | $HOCH_2$— | p-HOPh— |
| 39017 | $HOCH_2$— | p-$PhCH_2OPh$— |
| 39018 | $HOCH_2$— | p-$MeOCH_2CH_2OPh$— |
| 39019 | $HOCH_2$— | p-MeOPh— |
| 39020 | $HOCH_2$— | o-MeOPh— |
| 39021 | $HOCH_2$— | m-MeOPh— |
| 39022 | $HOCH_2$— | p-MePh— |
| 39023 | $HOCH_2$— | p-$(CH_3)_2NPh$— |
| 39024 | $HOCH_2$— | Ph— |
| 39025 | $HOCH_2$— | p-FPh |
| 39026 | $HOCH_2$— | 3-Indolyl- |
| 39027 | $HOCH_2$— | p-AcNHPh |
| 39028 | $HOCH_2$— | 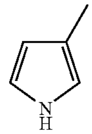 |
| 39029 | $HOCH_2$— | 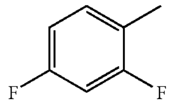 |
| 39030 | $HOCH_2$— | 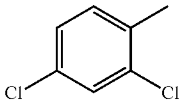 |

There will be described representative preparation processes according to this invention.

In a process for preparing a compound represented by general formula (5) or (6) from a compound represented by general formula (1) as a starting material in this invention, the meaning of the phrase "configuration of $R^1$ attached to the carbon at 4-position and the substituent represented by a nitrogen atom in the optically active 5-oxazolidinone is not changed throughout these reactions and relative configuration between the amino group and the hydroxy group in the optically active aminoalcohol represented by general formula (5) is erythro" may be described in the following reaction equations 1 and 2 in detail:

Reaction equation 1

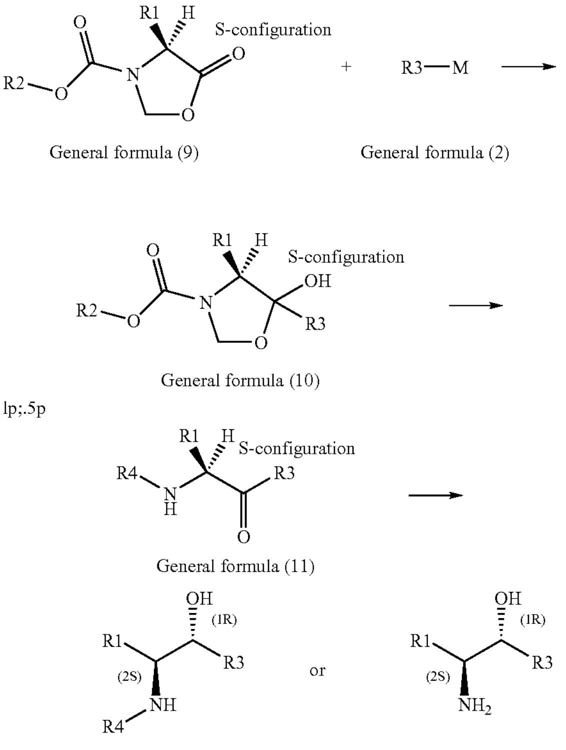

General formula (9)
General formula (2)
General formula (10)
lp;.5p
General formula (11)
General formula (12)
General formula (13)

Reaction equation 2

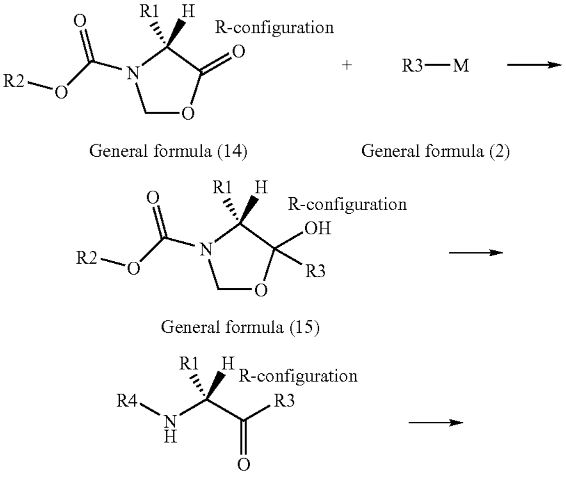

General formula (14)
General formula (2)
General formula (15)
General formula (16)

-continued

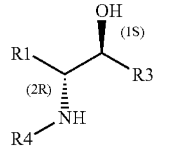

or

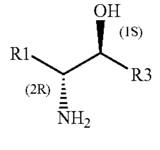

General formula (17) General formula (18)

Specifically, as shown in reaction equation 1, S-form optically active 5-oxazolidinone derivative represented by general formula (9) selectively gives a 1R,2S-optically active aminoalcohol derivative of erythro configuration represented by general formula (12) or (13). Furthermore, as shown in reaction formula 2, an R-form optically active 5-oxazolidinone derivative represented by general formula (14) can provide a 1S,2R-optically active aminoalcohol derivative of erythro configuration represented by general formula (17) or (18).

Each preparation step will be detailed.

Preparation of an Optically Active 5-Oxazolidinone Derivative Represented by General Formula (1)

An optically active 5-oxazolidinone derivative represented by general formula (1) can be provided according to a well-known process where an N-urethane protected compound derived from a readily available and inexpensive natural α-amino acid is reacted with paraformaldehyde in the presence of a catalytic amount of an acid (J. Am. Chem. Soc. 1957, 79, 5736).

Preparation of an Organometallic Reagent Represented by General Formula (2)

An organometallic reagent represented by general formula (2) may be easily prepared by a well-known process; for example, oxidative addition of a metal to a corresponding halogenated compound or transmetallation with an organometallic reagent.

In preparation of an organometallic reagent, there is no limitation of the solvent, as long as it is inert to the reaction, and, for example, ethers such as tetrahydrofuran, diethyl ether, dioxane and diglyme; toluene; and xylenes can be used. Among these, preferred is tetrahydrofuran alone or a mixture of tetrahydrofuran and another solvent in the light of solubility of a substrate. A reaction temperature may be generally −78° C. to a boiling point of the solvent used. Furthermore, an organometallic reagent, particularly a Grignard reagent can be used to give good results in a preparation process according to this invention.

A Grignard reagent may be easily prepared by, for example, adding dropwise a halogenated compound represented by $R^3X$ where X is as defined above, after initiating the reaction by adding a catalytic amount of an initiator such as 1,2-dibromoethane, ethyl bromide and iodine to magnesium dispersed in a solvent.

Preparation of an Optically Active 5-Hydroxyoxazolidine Derivative Represented by General Formula (3)

In a reaction of an optically active 5-oxazolidinone derivative represented by general formula (1) with an organometallic reagent represented by general formula (2), a reaction solvent may be, but not limited to, the same solvent as that used in preparing the organometallic reagent or a solvent mixture which does not significantly affect the reaction. The amount of the organometallic reagent is preferably, but not limited to, an equal to a five-fold moles, more preferably 1.0 to 2-fold moles per one mole of the 5-oxazolidinone derivative as a substrate. A reaction temperature may be preferably, but not limited to, an ambient temperature, room temperature, to −78° C. In this reaction, there are no restrictions to the order of adding the optically active 5-oxazolidinone derivative and the organometallic reagent. That is, the organometallic reagent may be added to the optically active 5-oxazolidinone derivative or vice versa. At the end of the reaction, for obtaining the optically active 5-hydroxyoxazolidine derivative produced, the excessive organometallic reagent in the reaction solution is decomposed using, for example, an aqueous diluted hydrochloric acid, diluted sulfuric acid, acetic acid, ammonium chloride, citric acid or potassium hydrogen sulfate solution and then the product can be isolated from the resulting mixture by a common separation/purification process such as extraction, concentration, neutralization, filtration, recrystallization and column chromatography.

Furthermore, as described above, a Grignard reagent can be used as an organometallic reagent to give particularly good results in this reaction. When using a Grignard reagent as an organometallic reagent, the conditions including a reaction solvent, the amount of the materials used, a reaction temperature, the order of adding the reagents, work-up of the reaction and isolation and purification of the product are as described for the above general preparation process when using an organometallic reagent.

The optically active 5-oxazolidine derivative prepared as described above is generally obtained as a mixture of two diastereomers because both R- and S-forms are formed for configuration at the 5-position in the oxazolidine. Depending on the conditions, high performance liquid chromatography or nuclear magnetic spectrometry may be performed to determine a diastereomer ratio. A diastereomer ratio may vary depending on the reaction conditions and properties of the product, and the diastereomers may be individually isolated or may be obtained as a mixture. However, a diastereomer mixture may be converted into an optically active aminoketone derivative represented by the same general formula (4) by, for example, treatment with an acid described below. It is, therefore, not necessary to separate the diastereomers as production intermediates in the light of a production cost.

Preparation of an Optically Active Aminoketone Derivative Represented by General Formula (4)

A process for converting an optically active 5-hydroxyoxazolidine derivative into an optically active aminoketone derivative represented by general formula (4) under an acidic condition can be generally conducted in a solvent. Examples of a solvent which can be used include, but not limited to, alcohols such as methanol and ethanol; acetonitrile; tetrahydrofuran; benzene; toluene; and water. These solvents may be used alone or in combination of two or more in a given mixing ratio. Examples of an acid which can be used include, but not limited to, inorganic acids such as hydrochloric acid, sulfuric acid and perchloric acid; organic acids such as p-toluenesulfonic acid and methanesulfonic acid; acidic resins such as Amberlite IR-120 and Amberlist; and Lewis acids such as boron trifluoride and zinc chloride. The amount of an acid used is an equal to 30-fold moles, preferably 1.5- to 10-fold moles per one mole of the optically active 5-hydroxyoxazolidine derivative. When using a resin, its amount is 5 to 200% by weight, preferably 10 to 100% by weight. A reaction temperature may be −30° C. to a boiling point of a solvent, particularly 0° C. to 100° C. An aminoketone derivative may be easily isolated from a reaction mixture by a common separation/purification method such as extraction, concentration, neutralization, filtration, recrystallization and column chromatography.

Preparation of an Optically Active Aminoalcohol Derivative Represented by General Formula (5)

A process for reducing an aminoketone derivative represented by general formula (4) with a reducing agent to give an optically active alcohol derivative represented by general formula (5) is generally conducted in a solvent. Examples of the solvent, which can be used include, but not limited to, methanol, ethanol, 2-propanol, tetrahydrofuran and water. These solvents may be used alone or in combination of two or more in a given mixing ratio.

Examples of the reducing agent include borane reagents such as borane-tetrahydrofuran complex; borohydride reagents such as sodium borohydride, zinc borohydride and sodium trimethoxyborohydride; alkylaluminum reagents such as diisopropylaluminum hydride; aluminum hydride reagents such as lithium aluminum hydride and lithium trialkoxyaluminum hydride; silane reagents such as trichlorosilane and triethylsilane; sodium metal in liquid ammonia; and magnesium metal in an alcohol. In particular, borohydride reagents such as sodium borohydride, zinc borohydride and sodium trimethoxyborohydride are suitable.

The amount of the reducing agent may be an equal to 10-fold moles per one mole of a material to be reduced. A reaction temperature is appropriately selected within the range of −78° C. to a boiling point of the solvent, preferably −40° C. to 80° C.

Alternatively, an aminoketone derivative represented by general formula (4) may be catalytically hydrogenated in the presence of an appropriate metal catalyst in an appropriate solvent under an atmosphere of hydrogen, to give an optically active aminoalcohol derivative represented by general formula (5). A hydrogen pressure may be, but not limited to, an ambient pressure to 3 MPa, preferably 0.3 MPa to 1 MPa. Any solvent may be used as long as it does not adversely affect the reaction; for example, methanol, ethanol, n-propanol, 2-propanol, n-butanol and water. These solvents may be used alone or in combination of two or more in a given mixing ratio. The amount of a solvent is 1 to 50 parts (wt/wt), preferably 3 to 20 parts per one part of the compounds.

Examples of the metal catalyst which can be used include nickel catalysts such as Raney nickel; platinum catalysts such as platinum-alumina, platinum-carbon and platinum oxide; palladium catalysts such as palladium-alumina, palladium-carbon and palladium hydroxide-carbon; ruthenium catalysts such as ruthenium oxide; and rhodium catalysts such as chlorotris(triphenylphosphine)rhodium which is also known as a Wilkinson catalyst, more suitably palladium catalysts. A reaction temperature may be, but not limited to, −20 to 200° C., preferably 0 to 60° C.

A process for deprotecting a compound represented by general formula (5) having a protected amino group as appropriate to give a free amine derivative represented by general formula (6) may be conducted by, for example, hydrolysis using an acid or base. Examples of an acid, which can be used include, but not limited to, inorganic acids such as hydrochloric acid, sulfuric acid and hydrobromic acid; and organic acids such as trifluoromethanesulfonic acid, is trifluoroacetic acid, p-toluenesulfonic acid and acetic acid. Examples of a base, which can be used, include inorganic bases such as sodium hydrogen carbonate, potassium carbonate, lithium hydroxide and sodium hydroxide; and organic bases such as triethylamine, morpholine, tetrabutylammonium fluoride and tetraethylammonium hydroxide.

An optically active aminoalcohol derivative represented by general formula (5) or (6) thus obtained may be isolated as crystals of the free amine or as a salt by adding, if necessary, an appropriate acid. A diastereomeric purity or optical purity of the compound may be improved by recrystallization.

When the compound is obtained as crystals of a free amine, any solvent which is suitable to such purification can be used for crystallization. Examples of such a solvent include alcohols such as methanol, ethanol, n-propanol and 2-propanol; esters such as ethyl acetate and butyl acetate; halogenated solvents such as chloroform and methylene chloride; ethers such as 1,4-dioxane and tetrahydrofuran; water; acetonitrile; 2-butanone; and toluene, which can be used alone or in combination of two or more.

Any acid which can form a crystalline salt suitable for purification may be used for salt formation. Examples of such an acid include inorganic acids such as hydrochloric acid, hydrobromic acid, sulfuric acid, nitric acid, sulfuric acid and phosphoric acid; and organic acids such as acetic acid, tartaric acid, citric acid, fumaric acid, methanesulfonate and p-toluenesulfonate.

Any solvent which is suitable for purification may be used for recrystallization. Examples of such solvent include alcohols such as methanol, ethanol, n-propanol and 2-propanol; esters such as ethyl acetate and butyl acetate; halogenated solvents such as chloroform and methylene chloride; ethers such as 1,4-dioxane and tetrahydrofuran; water; acetonitrile; 2-butanone; and toluene, which may be used alone or in combination of two or more.

A salt purified by recrystallization may be treated with an alkaline solution by a common procedure to be isolated as a free amine.

EXAMPLES

This invention will be more specifically described with reference to, but not limited to, Reference Examples and Examples.

Reference Example 1

Preparation of (4S)-N-benzyloxycarbonyl-4-methyl-5-oxazolidinone

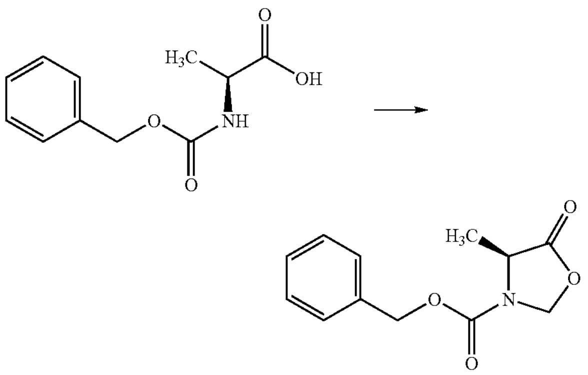

Benzyloxycarbonyl-L-alanine (19.3 g), paraformaldehyde (6.56 g) and p-toluenesulfonic acid monohydrate (0.17 g) were suspended in toluene (190 mL), and the mixture was heated at reflux while removing water produced. At the end of the reaction, the reaction mixture was cooled to room temperature, washed with saturated aqueous sodium hydrogen carbonate solution and then saturated saline. The toluene solution was dried over anhydrous sodium sulfate. The solvent was evaporated under a reduced pressure, the resulting crystals were filtrated to give the title compound (19.0 g) as white crystals in an yield of 93%.

Melting point: 91–93° C. $^1$H NMR ($CDCl_3$, 400 MHz) δ ppm: 1.54 (d, 3H, J=6.4 Hz), 4.29–4.31 (m, 1H), 5.18 (s, 2H), 5.28–5.29 (m, 1H), 5.47 (br, 1H), 7.33–7.41 (m, 5H); IR (KBr) $\nu_{max}$ 1778, 1685 cm$^{-1}$.

Reference Example 2

Preparation of 4-benzyloxybromobenzene

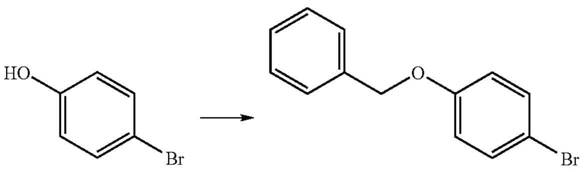

p-Bromophenol (25.0 g) and anhydrous potassium carbonate (20.0 g) were suspended in N,N-dimethylformamide (250 mL). To the suspension was added dropwise benzyl chloride (20.2 g) at room temperature. After heating at 95 to 100° C. for one hour, the reaction mixture was cooled to room temperature and water (400 mL) was added. After extraction with ethyl acetate, the organic layer was washed with saturated saline and dried over anhydrous sodium sulfate. The solvent was evaporated under a reduced pressure to give the title compound (34.3 g) as milk-white crystals in a yield of 90%.

Melting point: 55–57° C.; $^1$H-NMR ($CDCl_3$, 400 MHz) δ ppm: 5.04 (s, 2H), 6.83–6.87 (m, 2H), 7.31–7.43 (m, 2H).

Example 1

Preparation of (4S)-N-benzyloxycarbonyl-5-(4-benzyloxyphenyl)-4-methyl-5-hydroxyoxazolidine (Compound No. 1001)

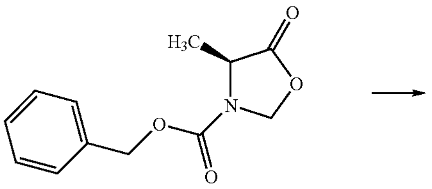

-continued

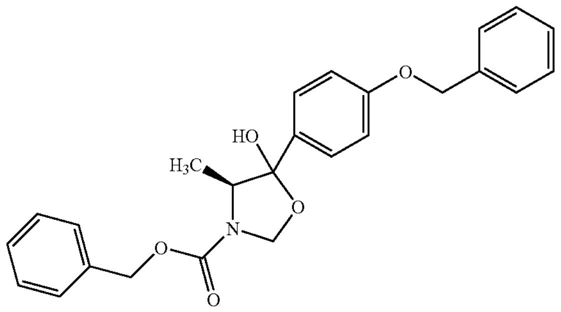

Preparation of a Grignard Reagent

To magnesium metal (1.16 g) in anhydrous tetrahydrofuran (20 mL) was added ethyl bromide (0.26 g) under nitrogen atmosphere, and the mixture was stirred at room temperature for 1 hour. At reflux of the solvent, a solution of 4-benzyloxybromobenzene (10.5 g) prepared in Reference Example 2 dissolved in anhydrous tetrahydrofuran (20 mL) was added dropwise over about 1 hour. At the end of addition, the mixture was stirred at reflux for further 40 min to prepare a Grignard reagent.

Grignard Reaction

In anhydrous tetrahydrofuran (40 mL) was dissolved (4S)-N-benzyloxycarbonyl-4-methyl-5-oxazolidinone (7.84 g) prepared in Reference Example 1 and the solution was cooled to −20° C. To the solution under nitrogen atmosphere was added dropwise the Grignard reagent prepared above while maintaining the internal temperature at −20° C. At the end of addition, the mixture was stirred for further 1 hour at that temperature, and then treated with an aqueous 5% hydrochloric acid solution. The solution was warmed to room temperature and extracted with ethyl acetate. The organic layer was dried over anhydrous sodium sulfate. The solution was concentrated in vacuo. The residue was purified by silica column chromatography (eluent: chloroform) to give the title compound (9.85 g) as a diastereomer mixture as white crystals in a yield of 71%.

Melting point: 83–86° C. $^1$H-NMR ($CDCl_3$, 400 MHz) indicated that a diastereomer ratio was about 2:1.

Major Diastereomer Product $^1$H-NMR ($CDCl_3$, 400 MHz) δ ppm: 1.47 (d, 3H, J=7.3 Hz), 3.81–3.84 (m, 1H), 4.79–5.07 (m, 2H), 5.14 (s, 2H), 5.14 (d, 1H, J=8.4 Hz), 5.20 (d, 1H, J=8.4 Hz), 5.87 (q, 1H, J=7.3 Hz), 7.02 (d, 2H, J=8.8 Hz), 7.23–7.44 (m, 10H), 8.01 (d, 2H, J=8.8 Hz)

Sub Diastereomer Product $^1$H-NMR ($CDCl_3$, 400 MHz) δ ppm: 1.49 (d, 3H, J=7.3 Hz), 3.60–3.70 (m, 1H), 4.79–5.15 (m, 4H), 5.13 (s, 2H), 5.57 (q, 1H, J=7.3 Hz), 6.91 (d, 2H, J=8.8 Hz), 7.23–7.44 (m, 10H), 7.83 (d, 2H, J=8.8 Hz); IR (neat) $\nu_{max}$ 3436, 3033, 1671, 1603, 1508 cm$^{-1}$.

Example 2

Preparation of (2S)-2-(benzyloxycarbonyl)amino-1-(4-benzyloxyphenyl)-1-propanone (Compound No.: 22001)

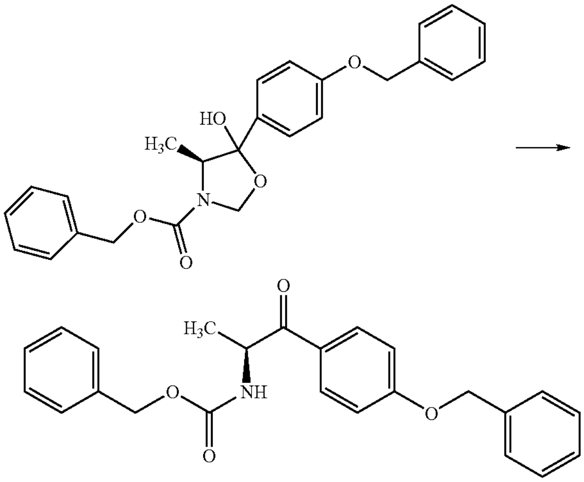

In toluene (50 mL) was dissolved (4S)-N-benzyloxycarbonyl-5-(4-benzyloxyphenyl)-4-methyl-5-hydroxyoxazolidine (3.8 g) prepared in Example 1. After adding Amberlist (300 mg), the mixture was reacted at room temperature. At the end of the reaction, Amberlist was filtered off, the filtrate was concentrated in vacuo. The residue was purified by silica column chromatography (eluent: chloroform) to give the title compound (3.1 g) as pale yellow crystals in a yield of 88%.

Melting point: 89–91° C.; $^1$H-NMR ($CDCl_3$, 400 MHz) δ ppm: 1.43 (d, 3H, J=6.83 Hz), 5.13 (s, 2H), 5.15 (s, 2H), 5.28–5.31 (m, 1H), 5.88 (br, 1H), 7.03 (d, 2H, J=9.0 Hz), 7.31–7.44 (m, 10H), 7.96 (d, 2H, J=9.0 Hz); IR (KBr) $\nu_{max}$ 3374, 1712, 1690 $cm^{-1}$;

Optical purity: 93%ee

HPLC Analysis Conditions:

Column: Daicel Chiral-Pak AD-RH (4.6 mmϕ×150 mm);

Mobile phase: methanol;

Flow rate: 0.5 mL/min;

Wavelength: 254 nm;

Temperature: room temperature;

$t_R$: (2S-form); 19.8 min;

(2R-form); 24.3 min.

Example 3

Preparation of (2S)-2-(benzyloxycarbonyl)amino-1-(4-benzyloxyphenyl)-1-propanone (Compound No. 22001)

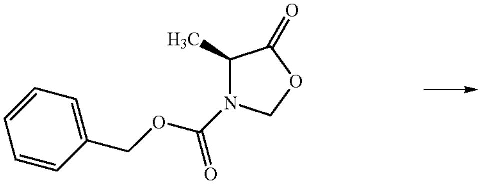

-continued

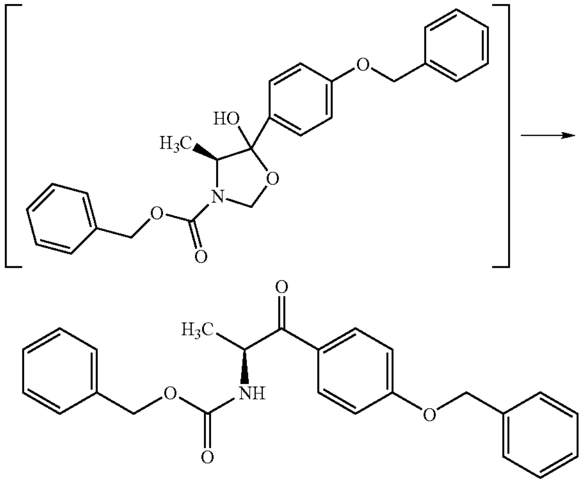

Preparation of a Grignard Reagent

To anhydrous tetrahydrofuran (15 mL) under nitrogen atmosphere were added magnesium metal (1.16 g) and ethyl bromide (0.05 g), and the mixture was stirred at room temperature for 30 min. To the mixture at reflux of the solvent was added dropwise a solution of 4-benzyloxybromobenzene (10.92 g) prepared in Reference Example 2 dissolved in anhydrous tetrahydrofuran (10 mL) over about 1 hour. At the end of addition, the mixture was stirred at reflux for further 30 min to prepare a Grignard reagent.

Grignard Reaction

In anhydrous tetrahydrofuran (26 mL) was dissolved (4S)-N-benzyloxycarbonyl-4-methyl-5-oxazolidinone (6.97 g) prepared in Reference Example 1 and the mixture was cooled to −20° C. To the solution under nitrogen atmosphere was added dropwise the Grignard reagent prepared above while maintaining the internal temperature at −20° C. At the end of addition, the mixture was stirred for further 1 hour at that temperature.

Deformylation

To the mixture was added a 6.5% aqueous hydrochloric acid solution, and the reaction was stirred at 35 to 40° C. for 6 hours. The aqueous layer was discarded after separation. Then to the organic layer was added a 5% aqueous hydrochloric acid solution, and the mixture was stirred at 45 to 50° C. for 4 hours. The reaction mixture was extracted with toluene and the organic layer was washed with water. The solution was concentrated in vacuo, 2-propanol (70 g) was added, and then the mixture was stirred at room temperature for 6 hours. The reaction mixture was cooled to 0 to 5° C. to precipitate crystals, which were then filtered to give the title compound (8.61 g) as pale yellow crystals in a yield of 80%.

Melting point: 89–91° C.; $^1$H-NMR ($CDCl_3$, 400 MHz) δ ppm: 1.43 (d, 3H, J=6.8 Hz), 5.13 (s, 2H), 5.15 (s, 2H), 5.28–5.31 (m, 1H), 5.88 (br, 1H), 7.03 (d, 2H, J=9.0 Hz), 7.31–7.44 (m, 10H), 7.96 (d, 2H, J=9.3 Hz); IR (KBr) $\nu_{max}$ 3374, 1712, 1690 $cm^{-1}$; Specific rotation: $[\alpha]^D_{24}$=+26° (C=1.00, $CHCl_3$) Optical purity: 99%ee (analytical conditions are as described in Example 2).

Example 4

Preparation of erythro-(1R,2S)-p-hydroxynorephedrine (Compound No. 28001)

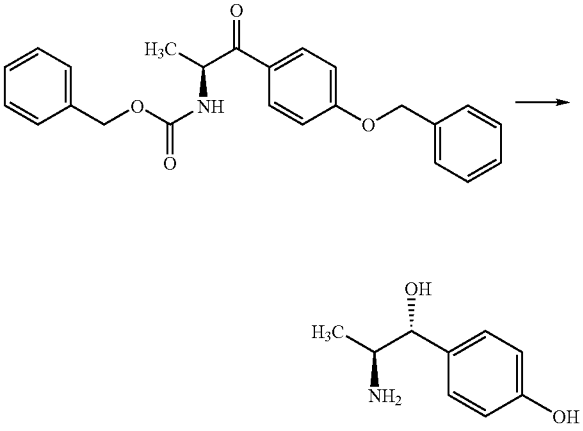

A mixture of (2S)-2-(benzyloxycarbonyl)amino-1-(4-benzyloxyphenyl)-1-propanone (4.8 g) prepared in Example 2 or 3, methanol (100 mL), water (50 mL) and 5% Pd/C (50% water-containing) (1.0 g) was stirred below 20° C. under hydrogen atmosphere (0.5 MPa) for 28 hours. The catalyst was filtered off, the filtrate was concentrated in vacuo, and the residue was slushed with 2-propanol to give the title compound (1.44 g) as white crystals in a yield of 70%.

Melting point: 163–165° C.; $^1$H-NMR (DMSO-$d_6$, 400 MHz) δ ppm: 0.85 (d, 3H, J=6.3 Hz), 2.77–2.83 (m, 1H), 4.17 (d, 1H, J=5.3 Hz), 4.96 (brs, 1H), 6.70 (d, 2H, J=8.3 Hz), 7.09 (d, 2H, J=8.3 Hz), 8.31 (s, 1H); IR (KBr) $\nu_{max}$ 3470, 1593, 1484, 1242 $cm^{-1}$; Specific rotation: $[\alpha]^D_{24}$=−18° (C=0.2, MeOH);

Erythro:threo=99.5:0.5;

HPLC Analysis Conditions:

Column: YMC TMS A-102 (6 mmφ×150 mm)

Mobile phase: acetonitrile:water=3:97 (each of $NaH_2PO_4$ and $Na_2HPO_4$ is 10 mM, pH 6.9);

Detection wavelength: 275 nm;

Flow rate: 0.5 mL/min;

Column temperature: 40° C.;

$t_R$: erythro form; 6.9 min;

threo form; 7.1 min;

Optical purity: 99%ee

HPLC Analysis Conditions:

Column: Daicel Crown-Pak CR(−) (4 mmφ×150 mm);

Mobile phase: $HClO_4$ aq (pH 3.5);

Detection wavelength: 275 nm;

Flow rate: 0.1 mL/min;

Column temperature: 25° C.

Example 5

Preparation of erythro-(1R,2S)-2-(benzyloxycarbonyl)amino-1-(4-benzyloxyphenyl)-1-propanol (Compound No.: 36002)

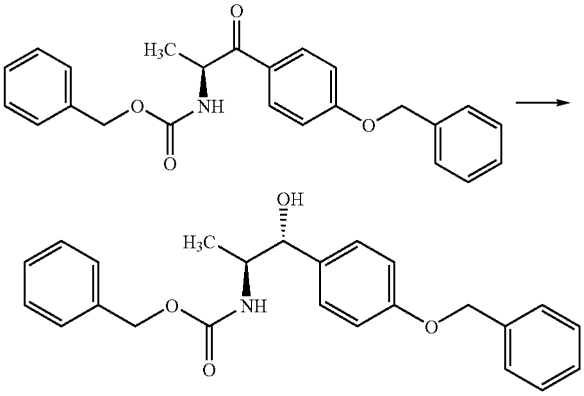

To methanol (25 mL) was added sodium borohydride (0.32 g), and the mixture was cooled to 0 to 5° C. To the solution was added (2S)-2-(benzyloxycarbonyl)amino-1-(4-benzyloxyphenyl)-1-propanone (2.00 g) prepared in Example 2 or 3, and the mixture was stirred at room temperature. Precipitated crystals were filtered, washed with methanol and then dried to give the title compound (1.39 g) as white crystals in a yield of 69%.

Melting point: 85–91° C.; $^1$H-NMR (DMSO-$d_6$, 400 MHz) δ ppm: 0.99 (d, 3H, J=6.59 Hz), 3.61–3.62 (m, 1H), 4.46–4.49 (m, 1H), 4.95 (s, 2H), 5.07 (s, 2H), 5.23 (m, 1H), 6.93 (d, 2H, J=7.08), 7.19–7.40 (m, 10H), 7.44 (d, 2H, J=7.08), 8.30 (s, 1H); IR (KBr) $\nu_{max}$ 3334, 1690 $cm^{-1}$.

Example 6

Preparation of erythro-(1R,2S)-p-hydroxynorephedrine (Compound No.: 28001)

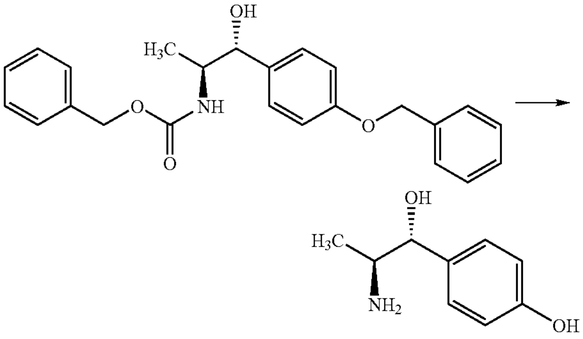

In methanol was dissolved erythro-(1R,2S)-2-(benzyloxycarbonyl)amino-1-(4-benzyloxyphenyl)-1-propanol (1.39 g) prepared in Example 5, and the solution was stirred with 5% Pd/C (50% water-containing) (0.03 g) under hydrogen atmosphere (ambient pressure) at room temperature for 2 hours. After removing the catalyst by filtration, the filtrate was concentrated in vacuo. The residue was crystallized with 2-propanol to give the title compound (0.65 g) as white crystals in a yield of 75%.

Melting point: 163–165° C.; $^{1}$H-NMR (DMSO-$d_6$, 400 MHz) δ ppm: 0.85 (d, 3H, J=6.3 Hz), 2.77–2.83 (m, 1H), 4.17 (d, 1H, J=5.3 Hz), 4.96 (brs, 1H), 6.70 (d, 2H, J=8.3 Hz), 7.09 (d, 2H, J=8.3 Hz), 8.31 (s, 1H); IR (KBr) $\nu_{max}$ 3470, 1593, 1484, 1242 $cm^{-1}$; Specific rotation: $[\alpha]^{D}_{24}$=−18° (C=0.2, MeOH); Erythro:threo=97.5:2.5 (analysis conditions are as described in Example 4);

Optical purity: 99%ee (analysis conditions are as described in Example 4).

Reference Example 3

Preparation of (4S)-N-tert-butoxycarbonyl-4-methyl-5-oxazolidinone

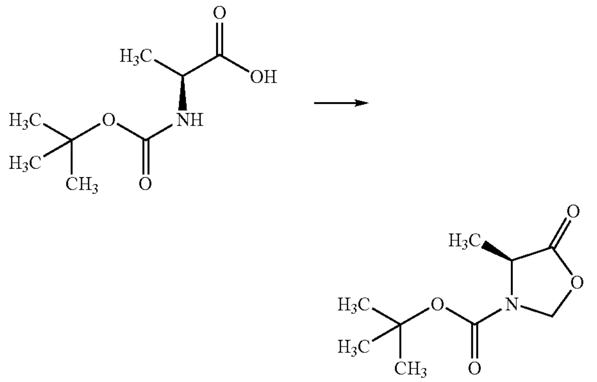

In toluene (250 mL) were suspended tert-butoxycarbonyl-L-alanine (18.9 g), paraformaldehyde (6.70 g) and p-toluenesulfonic acid monohydrate (0.19 g), and the suspension was heated at reflux while removing water produced. At the end of the reaction, the mixture was cooled to room temperature, washed with saturated aqueous sodium hydrogen carbonate solution and saturated saline. The toluene solution was dried over anhydrous sodium sulfate. The solvent was evaporated under a reduced pressure, and the crystals obtained were filtered to give the title compound (14.2 g) white crystals in a yield of 71%.

Melting point: 66–68° C.; $^{1}$H NMR ($CDCl_3$, 400 MHz) δ ppm: 1.49 (s, 9H), 1.52 (d, 2H, J=7.1 Hz), 4.23 (br, 1H), 5.23 (br, 1H), 5.41 (br, 1H); IR (KBr) $\nu_{max}$ 1798, 1698 $cm^{-1}$.

Example 7

Preparation of (4S)-5-(4-benzyloxyphenyl)-N-tert-butoxycarbonyl-4-methyl-5-hydroxyoxazolidine (Compound No.: 1015)

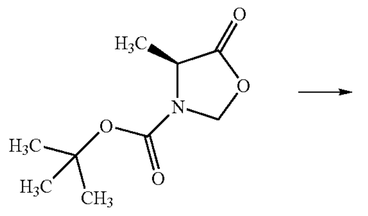

-continued

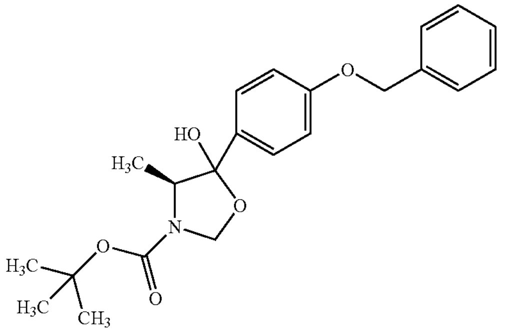

In anhydrous tetrahydrofuran (40 mL) was dissolved (4S)-N-tert-butoxycarbonyl-4-methyl-5-oxazolidinone (6.64 g) prepared in Reference Example 3, and the solution was cooled to −20° C. To the solution under nitrogen atmosphere was added dropwise a Grignard reagent prepared as described in Example 1 while maintaining the internal temperature at −20° C. At the end of addition, the mixture was stirred at that temperature for 1 hour and then treated with a 5% aqueous hydrochloric acid solution. The solution was warmed to room temperature and extracted with ethyl acetate. The organic layer was dried over anhydrous sodium sulfate. The solution was concentrated in vacuo and the residue was purified by silica column chromatography (eluent: chloroform) to give the title compound (10.2 g) as a diastereomer mixture as a pale yellow syrup in an yield of 80%.

$^{1}$H-NMR ($CDCl_3$, 400 MHz) δ ppm: 1.35–1.38 (m, 3H), 1.44–1.49 (m, 9H), 4.90–5.85 (m, 5H), 6.99–7.03 (m, 2H), 7.35–7.44 (m, 5H), 7.80–8.00 (m, 2H); IR (KBr) $\nu_{max}$ 3422, 1683 $cm^{-1}$.

Reference Example 4

Preparation of (4S)-N-benzyloxycarbonyl-4-isopropyl-5-oxazolidinone

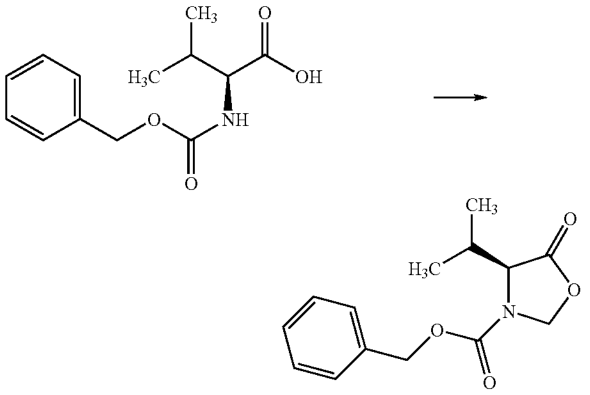

In toluene (250 mL) were suspended benzyloxycarbonyl-L-valine (25.1 g), paraformaldehyde (6.70 g) and p-toluenesulfonic acid monohydrate (0.19 g), and the suspension was heated at reflux while removing water produced. At the end of the reaction, the mixture was cooled to room temperature, washed with saturated aqueous sodium hydrogen carbonate solution and saturated saline. The toluene solution was dried over anhydrous sodium sulfate. The solvent was evaporated under a reduced pressure to give the title compound (23.7 g) as colorless transparent syrup in an yield of 90%.

$^1$H-NMR ($CDCl_3$, 400 MHz) δ ppm: 1.00 (d, 3H, J=6.6 Hz), 1.07 (d, 3H, J=6.6 Hz), 2.30–2.40 (m, 1H), 4.22 (bs, 1H), 5.15–5.22 (m, 3H), 5.56 (bs, 1H), 7.15–7.40 (m, 5H); IR (KBr) $\nu_{max}$ 1798, 1698 $cm^{-1}$.

Example 8

Preparation of (4S)-5-(4-benzyloxyphenyl)-N-benzyloxycarbonyl-4-isopropyl-5-hydroxyoxazolidine (Compound No.: 2001)

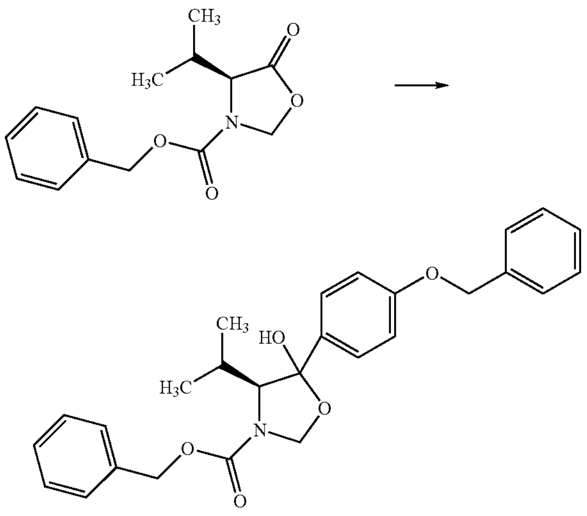

In anhydrous tetrahydrofuran (22 mL) was dissolved (4S)-benzyloxycarbonyl-4-isopropyl-5-oxazolidinone (5.20 g) prepared in Reference Example 4, and the solution was cooled to −20° C. To the solution under nitrogen atmosphere was added dropwise a Grignard reagent prepared as described in Example 1 while maintaining the internal temperature at −10 to 20° C. At the end of addition, the mixture was stirred at that temperature for 1 hour and then treated with a 12.5% aqueous hydrochloric acid solution. The solution was warmed to room temperature, extracted with toluene. The organic layer was dried over anhydrous magnesium sulfate. The solution was concentrated in vacuo. The residue was purified by silica column chromatography (eluent: hexane/ethyl acetate=2/1) to give the title compound (4.72 g) as a diastereomer mixture as a pale yellow syrup in an yield of 53%.

$^1$H-NMR ($CDCl_3$, 400 MHz) indicated that a diastereomer ratio was about 1.9:1.

Major Diastereomer Product $^1$H-NMR ($CDCl_3$, 400 MHz) δ ppm: 0.85 (d, 3H, J=6.6 Hz), 0.98 (d, 2H, J=6.6), 2.29–2.40 (m, 1H), 3.29 (m, 1H), 4.79 (m, 1H), 5.10–5.50 (m, 6H), 7.02 (d, 2H, J=8.7 Hz), 7.28–7.45 (m, 10H), 8.11 (d, 2H, J=8.7 Hz);

Sub Diastereomer Product $^1$H-NMR ($CDCl_3$, 400 MHz) δ ppm: 0.83 (d, 3H, J=6.2 Hz), 1.00 (d, 2H, J=6.2), 2.29–2.40 (m, 1H), 3.55 (m, 1H), 4.79 (m, 1H), 5.10–5.50 (m, 6H), 6.81 (d, 2H, J=9.0 Hz), 7.28–7.45 (m, 10H), 7.85 (d, 2H, J=9.0 Hz); IR (KBr) $\nu_{max}$ 3422, 1683 $cm^{-1}$ Example 9

Preparation of (2S)-2-(benzyloxycarbonyl)amino-1-(4-benzyloxyphenyl)-3-methyl-1-butanone (Compound No.: 23001)

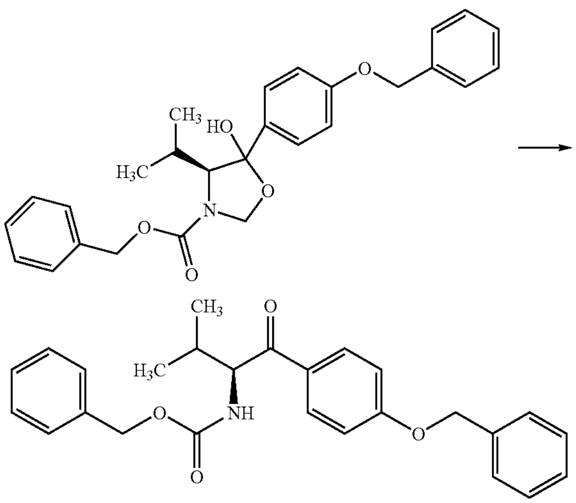

In tetrahydrofuran (4 mL) was dissolved (4S)-N-benzyloxycarbonyl-5-(4-benzyloxyphenyl)-4-isopropyl-5-hydroxyoxazolidine (1.38 g) prepared in Example 8, and to the solution were added water (5 mL) and conc. hydrochloric acid (2 mL). The mixture was stirred at room temperature for 24 hours. The reaction was diluted with toluene and the aqueous layer was discarded. The organic layer was washed with water three times. The organic layer was dried over anhydrous magnesium sulfate and then concentrated in vacuo. The residue was purified by silica column chromatography (eluent: hexane/ethyl acetate=2/1) to give the title compound (466 mg) as pale yellow crystals in a yield of 36%.

Melting point: 75–77° C.; $^1$H-NMR ($CDCl_3$, 400 MHz) δ ppm: 0.76 (d, 3H, J=6.8 Hz), 1.04 (d, 3H, J=6.8 Hz), 2.16 (m, 1H), 5.11 (s, 1H), 5.14 (s, 1H), 5.24 (dd, 1H, J=8.8, 4 Hz), 5.70 (d, 1H, J=8.8 Hz), 7.03 (d, 2H, J=8.8 Hz), 7.30–7.45 (m, 10H), 7.96 (d, 2H, J=8.8 Hz); IR (KBr) $\nu_{max}$ 3422, 1683 $cm^{-1}$.

Example 10

Preparation of (4S)-N-benzyloxycarbonyl-5-(4-methoxyphenyl)-4-methyl-5-hydroxyoxazolidine (Compound No.: 1020)

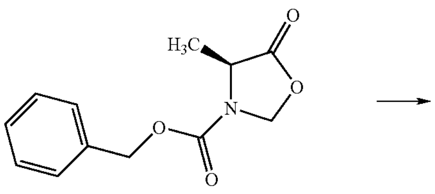

-continued

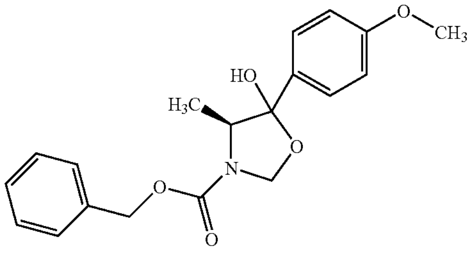

Preparation of a Grignard Reagent

To anhydrous tetrahydrofuran (20 mL) under nitrogen atmosphere were added magnesium metal (756 mg) and ethyl bromide (0.1 g), and the mixture was stirred at room temperature for 1 hour. To the mixture at reflux of the solvent was added dropwise a solution of 4-bromoanisole (3.76 g) dissolved in anhydrous tetrahydrofuran (20 mL) over 1 hour. At the end of addition, the mixture was stirred at reflux for further 40 min to prepare a Grignard reagent.

Grignard Reaction

In anhydrous tetrahydrofuran (30 mL) was dissolved (4S)-N-benzyloxycarbonyl-4-methyl-5-oxazolidinone (7.70 g) prepared in Reference Example 1, and the solution was cooled to −20° C. To the solution under nitrogen atmosphere was added dropwise the Grignard reagent while maintaining the internal temperature at −20° C. At the end of addition, the mixture was stirred for 1 hour at that temperature and then treated with a 5% aqueous hydrochloric acid solution. The solution was warmed to room temperature and extracted with ethyl acetate. The organic layer was dried over anhydrous sodium sulfate. The solution was concentrated in vacuo. The residue was purified by silica column chromatography (eluent: hexane/ethyl acetate=2/1 to 3/2), to give the title compound (4.56 g) as a diastereomer mixture as a colorless transparent syrup in a yield of 66%.

$^1$H-NMR ($CDCl_3$, 400 MHz) indicated that a diastereomer ratio was about 2:1.

Major Diastereomer Product $^1$H-NMR ($CDCl_3$, 400 MHz) δ ppm: 1.47 (d, 3H, J=7 Hz), 3.70–3.75 (m, 1H), 3.87 (s, 3H), 4.80–5.20 (m, 2H), 5.16 (d, 1H, J=12.4 Hz), 5.25 (d, 1H, J=12.4 Hz), 5.88 (q, 1H, J=7 Hz), 6.95 (d, 2H, J=9.0 Hz), 7.23–7.36 (m, 5H), 8.02 (d, 2H, J=9.0 Hz);

Minor Diastereomer Product $^1$H-NMR ($CDCl_3$, 400 MHz) δ ppm: 1.48 (d, 3H, J=7 Hz), 3.70–3.75 (m, 1H), 3.86 (s, 3H), 4.80–5.20 (m, 2H), 5.16 (d, 1H, J=12.4 Hz), 5.25 (d, 1H, J=12.4 Hz), 5.57 (q, 1H, J=7 Hz), 6.83 (d, 2H, J=8.8 Hz), 7.23–7.36 (m, 5H), 8.83 (d, 2H, J=8.8 Hz) IR (neat) $\nu_{max}$ 3443, 1697, 1601 $cm^{-1}$.

Example 11

Preparation of (2S)-2-(benzyloxycarbonyl)amino-1-(4-methoxyphenyl)-1-propanone (Compound No.: 22020)

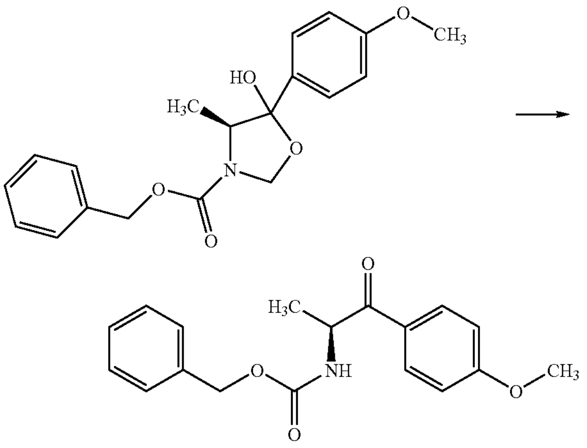

In tetrahydrofuran (4 mL) was dissolved (4S)-N-benzyloxycarbonyl-5-(4-methoxyphenyl)-4-methyl-5-hydroxyoxazolidine (1.72 g) prepared in Example 10 and then water (5 mL) and conc. hydrochloric acid (2 mL) were added. The mixture was stirred at room temperature for 24 hours. The reaction was diluted with toluene, the aqueous layer was discarded, and then the organic layer was dried over anhydrous magnesium sulfate. After concentration under a reduced pressure, the residue was purified by silica column chromatography (eluent: hexane/ethyl acetate=3/1) to give the title compound (1.40 mg) as white crystals in a yield of 89%.

Melting point: 46–48° C.; $^1$H-NMR ($CDCl_3$, 400 MHz) δ ppm: 1.43 (d, 3H, J=6.8 Hz), 3.88 (s, 3H), 5.13 (s, 2H), 5.30 (dq, 1H, J=7.1, 6.8 Hz), 5.91 (d, 1H, J=7.1 Hz), 6.96 (d, 2H, J=8.8 Hz), 7.29–7.37 (m, 5H), 7.96 (d, 2H, J=8.8 Hz); IR (KBr) $\nu_{max}$ 3458, 2958, 1714, 1676, 1597, 1527 $cm^{-1}$.

Example 12

Preparation of (4S)-N-benzyloxycarbonyl-5-(2,4-difluorophenyl)-4-methyl-5-hydroxyoxazolidine (Compound No.: 1030)

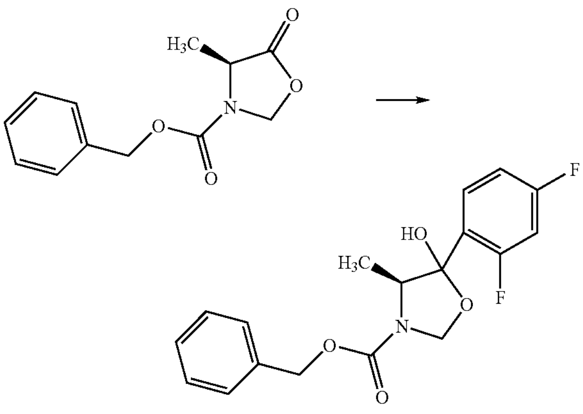

Preparation of a Grignard Reagent

To anhydrous tetrahydrofuran (20 mL) under nitrogen atmosphere were added magnesium metal (2.56 g) and iodine (30 mg). To the mixture at room temperature was added one-fifth of a solution of 2,4-difluorobromobenzene (19.3 g) dissolved in anhydrous tetrahydrofuran (60 mL) in one portion. Five minutes after addition, Grignard reagent formation was initiated as indicated by temperature rising of the reaction. While maintaining a reaction temperature below 45° C., the remaining four-fifths of the reagent was added dropwise over about 30 min. At the end of addition, the mixture was stirred at 25 to 40° C. for 30 min to give a Grignard reagent.

Grignard Reaction

In anhydrous tetrahydrofuran (68 mL) was dissolved (4S)-N-benzyloxycarbonyl-4-methyl-5-oxazolidinone (21.2 g) prepared in Reference Example 1, and the solution was cooled to −20° C. To the solution under nitrogen atmosphere was added dropwise the Grignard reagent prepared while maintaining the internal temperature at −20° C. At the end of addition, the mixture was stirred at that temperature for one hour and treated with a 5% aqueous hydrochloric acid solution. The solution was warmed to room temperature and extracted with toluene. The organic layer was dried over anhydrous magnesium sulfate. The solution was concentrated in vacuo. The residue was purified by silica column chromatography (eluent: hexane/ethyl acetate=2/1) to give the title compound (21.4 g) as a diastereomer mixture as a pale yellow syrup in a yield of 68%.

$^{1}$H-NMR ($CDCl_3$, 400 MHz) δ ppm: 1.52 and 1.51 (2d, 3H, J=6.8 Hz), 3.20–3.45 (m, 1H), 4.30–4.50 (m, 1H), 4.70–5.45 (m, 4H), 6.55–6.90 (m, 2H), 7.30–7.40 (m, 5H), 7.50–7.90 (m, 1H); IR (KBr) $\nu_{max}$ 3402, 1803, 1701, 1614 $cm^{-1}$.

Example 13

Preparation of (2S)-2-(benzyloxycarbonyl)amino-1-(2,4-difluorophenyl)-1-propanone (Compound No.: 22030)

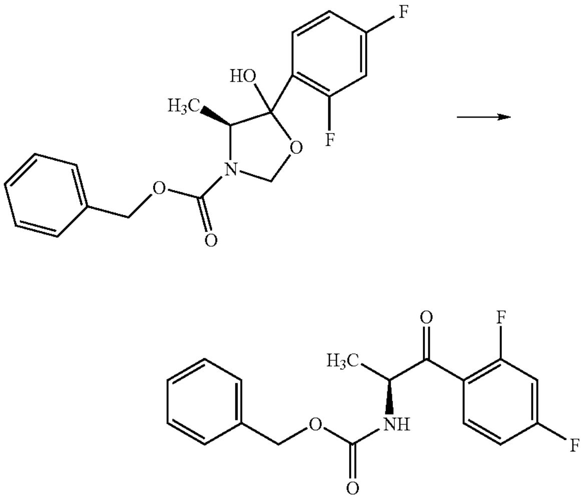

In tetrahydrofuran (70 mL) was dissolved (4S)-2-(benzyloxycarbonyl)amino-5-(2,4-difluorophenyl)-4-methyl-5-hydroxyoxazolidine (14.0 g) prepared in Example 12, and water (50 mL) and conc. hydrochloric acid (20 mL) were added. The mixture was stirred at room temperature for 24 hours. The reaction mixture was diluted with toluene, the aqueous layer was discarded, and the organic layer was washed with water three times. The organic layer was dried over anhydrous magnesium sulfate and concentrated in vacuo. The residue was purified by silica column chromatography (eluent: hexane/ethyl acetate=3/1) to give the title compound (11.7 g) as a pale yellow syrup in a yield of 92%.

$^{1}$H-NMR ($CDCl_3$, 400 MHz) δ ppm: 1.40 (d, 3H, J=7.0 Hz), 5.10 (s, 2H), 5.05–5.20 (m, 1H), 5.75–5.80 (m, 1H), 6.88–6.94 (m, 1H), 6.98–7.02 (m, 1H), 7.30–7.37 (m, 5H), 7.95–8.01 (m, 1H); IR (neat) $\nu_{max}$ 3358, 1718, 1681, 1611, 1532 $cm^{-1}$, Optical purity: 90%ee;

HPLC Analysis Conditions

Column: Daicel Chiral-Pak AD-RH (4.6 mmφ×150 mm);

Mobile phase: methanol;

Flow rate: 0.5 mL/min;

Wavelength: 254 nm;

Temperature: room temperature;

$t_R$: (2R-form); 6.5 min (2S-form); 7.5 min.

Reference Example 5

Preparation of (4R)-N-benzyloxycarbonyl-4-methyl-5-oxazolidinone

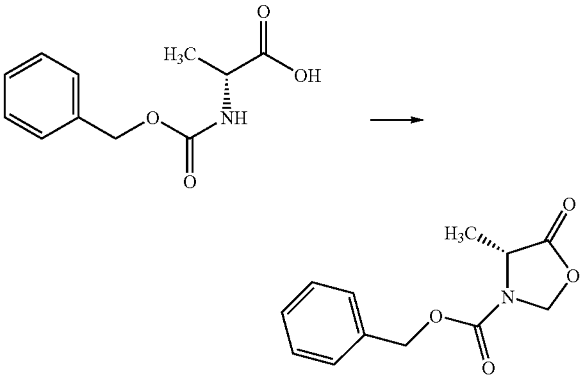

In toluene (190 mL) were suspended benzyloxycarbonyl-D-alanine (19.3 g), paraformaldehyde (6.56 g) and p-toluenesulfonic acid monohydrate (0.17 g), and the mixture was heated at reflux while removing water produced. At the end of the reaction, the mixture was cooled to room temperature, and washed with saturated aqueous sodium hydrogen carbonate solution and saturated saline. The toluene solution was dried over anhydrous sodium sulfate. The solvent was evaporated under a reduced pressure. The precipitated crystals were filtered to give the title compound (17.4 g) as white crystals in a yield of 85%.

Melting point: 89–91° C.; $^{1}$H NMR ($CDCl_3$, 400 MHz) δ ppm: 1.54 (d, 3H, J=6.4 Hz), 4.29–4.31 (m, 1H), 5.18 (s, 2H), 5.28–5.29 (m, 1H), 5.47 (br, 1H), 7.33–7.41 (m, 5H); IR (KBr) $\nu_{max}$ 1778, 1685 $cm^{-1}$.

Example 14

Preparation of (4R)-N-benzyloxycarbonyl-5-(4-benzyloxyphenyl)-4-methyl-5-hydroxyoxazolidine (Compound No.: 19001)

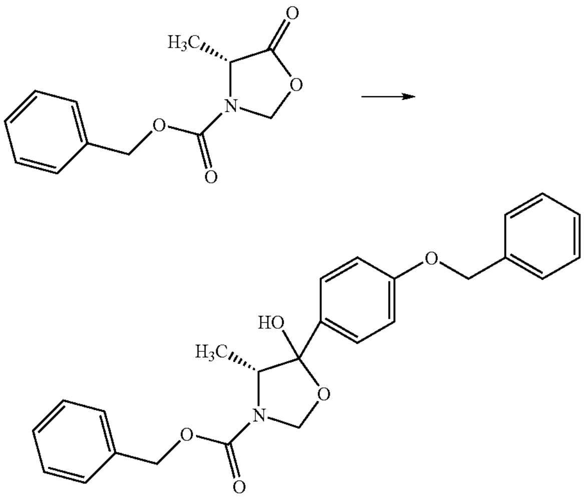

(4R)-N-Benzyloxycarbonyl-4-methyl-5-oxazolidinone (2.61 g) prepared in Reference Example 5 was processed as described in Example 1 to give the title compound (9.0 g) as a diastereomer mixture as white crystals in an yield of 65%.

Melting point: 82–86° C. $^1$H-NMR ($CDCl_3$, 400 MHz) indicated that a diastereomer ratio was about 2:1.

Major Diastereomer Product $^1$H-NMR ($CDCl_3$, 400 MHz) δ ppm: 1.47 (d, 3H, J=7.3 Hz), 3.81–3.84 (m, 1H), 4.79–5.07 (m, 2H), 5.14 (s, 2H), 5.14 (d, 1H, J=8.4 Hz), 5.20 (d, 1H, J=8.4 Hz), 5.87 (q, 1H, J=7.3 Hz), 7.02 (d, 2H, J=8.8 Hz), 7.23–7.44 (m, 10H), 8.01 (d, 2H, J=8.8 Hz);

Sub Diastereomer Product $^1$H-NMR ($CDCl_3$, 400 MHz) δ ppm: 1.49 (d, 3H, J=7.3 Hz), 3.60–3.70 (m, 1H), 4.79–5.15 (m, 4H), 5.13 (s, 2H), 5.57 (q, 1H, J=7.3 Hz), 6.91 (d, 2H, J=8.8 Hz), 7.23–7.44 (m, 10H), 7.83 (d, 2H, J=8.8 Hz); IR (neat) $\nu_{max}$ 3436, 3033, 1671, 1603, 1508 $cm^{-1}$.

Example 15

Preparation of (2R)-2-(benzyloxycarbonyl)amino-1-(4-benzyloxyphenyl)-1-propanone (Compound No. 25001)

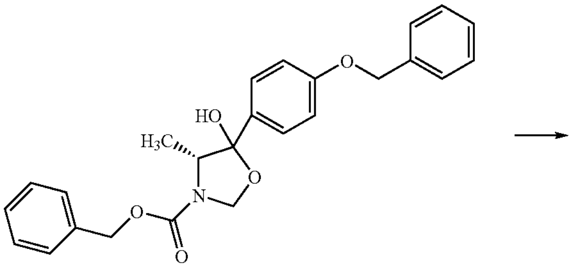

-continued

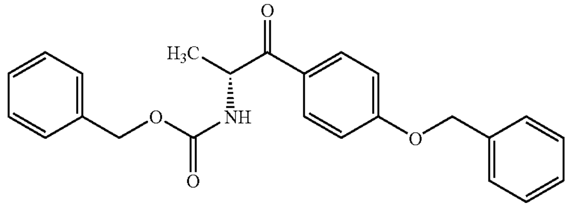

(4R)-N-Benzyloxycarbonyl-5-(4-benzyloxyphenyl)-4-methyl-5-hydroxyoxazolidine (2.1 g) prepared in Example 14 was processed as described in Example 9 to give the title compound (1.85 g) as pale yellow crystals in an yield of 95%.

Melting point: 88–90° C.; $^1$H-NMR ($CDCl_3$, 400 MHz) δ ppm: 1.43 (d, 3H, J=6.83 Hz), 5.13 (s, 2H), 5.15 (s, 2H), 5.28–5.31 (m, 1H), 5.88 (br, 1H), 7.03 (d, 2H, J=9.0 Hz), 7.31–7.44 (m, 10H), 7.96 (d, 2H, J=9.0 Hz); IR (KBr) $\nu_{max}$ 3374, 1712, 1690 $cm^{-1}$; Specific rotation: $[\alpha]^D{}_{24}$=−25° (C=1.00, $CHCl_3$); Optical purity: 98%ee (analysis conditions are as described in Example 3).

Example 16

Preparation of (4R)-N-benzyloxycarbonyl-5-(2,4-difluorophenyl)-4-methyl-5-hydroxyoxazolidine (Compound No.: 19030)

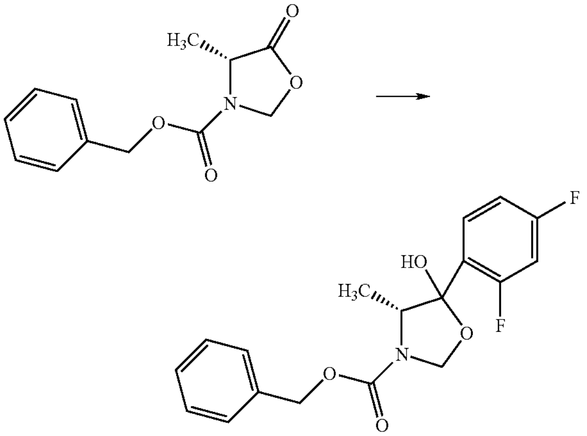

Preparation of a Grignard Reagent

To anhydrous tetrahydrofuran (10 mL) under nitrogen atmosphere were added magnesium metal (1.28 g) and iodine (20 mg). A solution of 2,4-difluorobromobenzene (9.65 g) in anhydrous tetrahydrofuran (30 mL) at room temperature was used as described in Example 12 to give a Grignard reagent.

Grignard Reaction

In anhydrous tetrahydrofuran (34 mL) was dissolved (4R)-N-benzyloxycarbonyl-4-methyl-5-oxazolidinone (10.6 g). The mixture was processed as described in Example 12 to give the title compound (10.7 g) as a diastereomer mixture as a pale yellow syrup in a yield of 68%.

$^1$H-NMR ($CDCl_3$, 400 MHz) δ ppm: 1.52 and 1.51 (2d, 3H, J=6.8 Hz), 3.20–3.45 (m, 1H), 4.30–4.50 (m, 1H), 4.70–5.45 (m, 4H), 6.55–6.90 (m, 2H), 7.30–7.40 (m, 5H), 7.50–7.90 (m, 1H); IR (KBr) $\nu_{max}$ 3402, 1803, 1701, 1614 $cm^{-1}$.

Example 17

Preparation of (2R)-2-(benzyloxycarbonyl)amino-1-(2,4-difluorophenyl)-1-propanone (Compound No.: 25030)

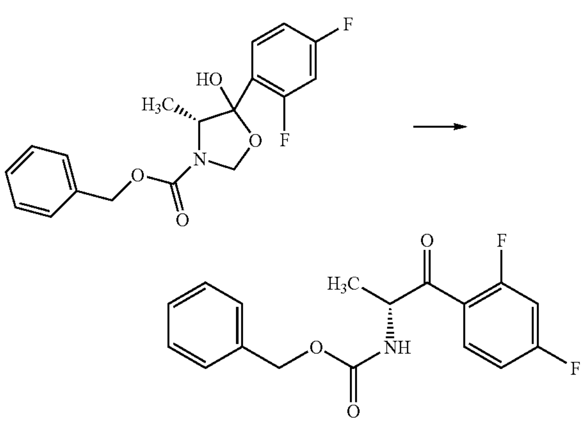

In tetrahydrofuran (35 mL) was dissolved (4R)-2-(benzyloxycarbonyl)amino-5-(2,4-difluorophenyl)-4-methyl-5-hydroxyoxazolidine (6.98 g) prepared in Example 16, and water (25 mL) and conc. hydrochloric acid (10 mL) were added. The mixture was processed as described in Example 13 to give the title compound (5.87 g) as pale yellow syrup in a yield of 92%.

$^1$H-NMR ($CDCl_3$, 400 MHz) δ ppm: 1.40 (d, 3H, J=7.0 Hz), 5.10 (s, 2H), 5.05–5.20 (m, 1H), 5.75–5.80 (m, 1H), 6.88–6.94 (m, 1H), 6.98–7.02 (m, 1H), 7.30–7.37 (m, 5H), 7.95–8.01 (m, 1H); IR (neat) $\nu_{max}$ 3358, 1718, 1681, 1611, 1532 $cm^{-1}$; Optical purity: 90%ee (analysis conditions are as described in Example 12).

INDUSTRIAL APPLICABILITY

According to the present invention, an optically active aminoalcohol derivative represented by general formula (5) or (6), which is useful as a production intermediate for a medicine or agricultural agent, can be produced stably in a large scale with an industrially adequate optical purity and a lower cost. This invention also provides an optically active 5 -hydroxyoxazolidine derivative represented by general formula (3) as an important intermediate for production of the above optically active aminoalcohol derivative or other optically active amine derivatives and a generally usable preparation process therefor, as well as an optically aminoketone derivative represented by general formula (4) and a generally usable preparation process therefor. The production technique may be extensively applicable to preparation of optically active amine derivatives in addition to preparation of the above optically active aminoalcohol derivative, and thus is industrially excellent technique.

What is claimed is:

1. A process for preparing an optically active aminoalcohol wherein an optically active 5-oxazolidinone derivative represented by general formula (1):

(1)

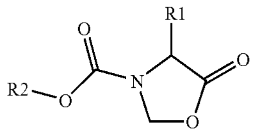

wherein $R^1$ represents an unprotected or optionally protected side chain in a natural α-amino acid; and $R^2$ represents optionally substituted aryl, optionally substituted alkyl, or optionally substituted aralkyl, is reacted with an organometallic reagent represented by general formula (2):

$R^3$—M (2)

wherein $R^3$ represents optionally substituted aryl or optionally substituted heterocycle; M represents one selected from the group consisting of Li, MgX, ZnX, $TiX_3$ and CuX; and X represents halogen, to form an optically active 5-hydroxyoxazolidine derivative represented by general formula (3):

(3)

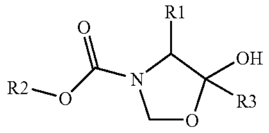

wherein $R^1$, $R^2$ and $R^3$ are as defined above, which is then treated under acidic conditions to give an optically active aminoketone derivative represented by general formula (4):

(4)

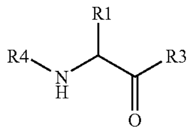

wherein $R^1$ and $R^3$ are as defined above; and $R^4$ represents hydrogen or optionally substituted alkyloxycarbonyl, optionally substituted aryloxycarbonyl or optionally substituted aralkyloxycarbonyl as a protective group, which is then treated with a reducing agent or catalytically hydrogenated with a metal catalyst to stereoselectively provide an optically active aminoalcohol derivative represented by general formula (5):

(5)

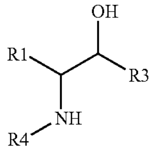

wherein $R^1$, $R^3$ and $R^4$ are as defined above;

provided that configuration of $R^1$ attached to the asymmetric carbon at 4-position and the substituent represented by a nitrogen atom in the optically active 5-oxazolidinone represented by general formula (1) is not changed throughout these reactions and relative configuration between the amino group and the hydroxy group in the optically active aminoalcohol represented by general formula (5) is an erythro configuration.

2. A process for preparing an aminoalcohol wherein an optically active 5-oxazolidinone derivative represented by a general formula (1):

(1)

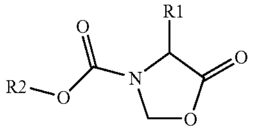

wherein $R^1$ represents an unprotected or optionally protected side chain in a natural α-amino acid; and $R^2$ represents optionally substituted aryl, optionally substituted alkyl, or optionally substituted aralkyl, is reacted with an organometallic reagent represented by general formula (2):

$R^3$—M (2)

wherein $R^3$ represents optionally substituted aryl or optionally substituted heterocycle; M represents one selected from the group consisting of Li, MgX, ZnX, $TiX_3$ and CuX; and X represents halogen, to form an optically active 5-hydroxyoxazolidine derivative represented by general formula (3):

(3)

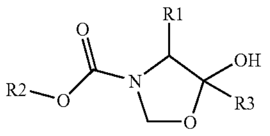

wherein $R^1$, $R^2$ and $R^3$ are as defined above, which is then treated under acidic conditions to give an optically active aminoketone derivative represented by general formula (4):

(4)

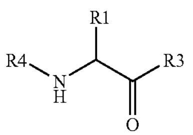

wherein $R^1$ and $R^3$ are as defined above; and $R^4$ represents hydrogen or optionally substituted alkyloxycarbonyl, optionally substituted aryloxycarbonyl or optionally substituted aralkyloxycarbonyl as a protective group, which is then treated with a reducing agent or catalytically hydrogenated with a metal catalyst to provide an optically active aminoalcohol derivative represented by general formula (5):

(5)

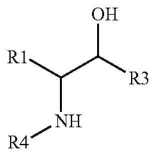

wherein $R^1$, $R^3$ and $R^4$ are as defined above, and then, when $R^4$ is a protective group, the amino group in the product is deprotected to give an optically active aminoalcohol derivative represented by general formula (6):

(6)

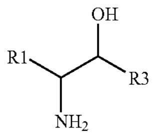

wherein $R^1$ and $R^3$ are as defined above;

provided that configuration of $R^1$ attached to the asymmetric carbon at 4-position and the substituent represented by a nitrogen atom in the optically active 5-oxazolidinone represented by general formula (1) is not changed throughout these reactions and relative configuration between the amino group and the hydroxy group in the optically active aminoalcohol represented by general formula (6) is an erythro configuration.

3. The process for preparing an optically active aminoalcohol as claimed in claim 1 or 2 wherein $R^1$ represents methyl, isopropyl, isobutyl, benzyl, hydroxymethyl, benzyloxymethyl, phenylthiomethyl, methylthiomethyl, alkyloxycarbonylmethyl or alkyloxycarbonylethyl; $R^2$ represents benzyl, tert-butyl, methyl, ethyl, isopropyl or 9-fluorenylmethyl.

4. The process for preparing an optically active aminoalcohol as claimed in claim 1 or 2 wherein $R^3$ is represented by general formula (7):

(7)

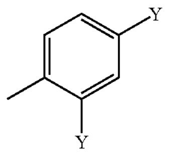

wherein Y represents halogen; or by general formula (8):

(8)

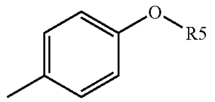

wherein $R^5$ represents hydrogen, optionally substituted alkyl, optionally substituted cycloalkyl, optionally substituted aralkyl, optionally substituted phenyl, optionally substituted heterocycle or optionally substituted heterocycloalkyl.

5. The process for preparing an optically active aminoalcohol derivative as claimed in claim 1 or 2 wherein $R^1$ represents methyl; and $R^3$ is represented by general formula (8):

(8)

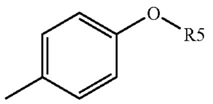

wherein $R^5$ represents hydrogen, optionally substituted alkyl, optionally substituted cycloalkyl, optionally substituted aralkyl, optionally substituted phenyl, optionally substituted heterocycle or optionally substituted heterocyclealkyl.

6. An optically active 5-hydroxyoxazolidine derivative represented by general formula (3):

(3)

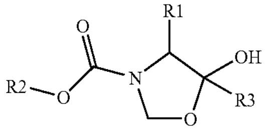

wherein $R^1$ represents an unprotected side chain or optionally protected side chain in a natural α-amino acid; and wherein $R^2$ represents benzyl, tert-butyl, methyl, ethyl, isopropyl or 9-fluorenylmethyl.

7. The optically active 5-hydroxyoxazolidine derivative as claimed in claim 6 wherein $R^3$ is represented by general formula (7):

(7)

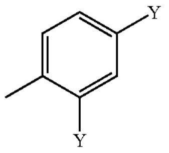

wherein Y represents halogen; or general formula (8):

(8)

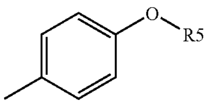

wherein $R^5$ represents hydrogen, optionally substituted alkyl, optionally substituted cycloalkyl, optionally substituted aralkyl, optionally substituted phenyl, optionally substituted heterocycle or optionally substituted heterocyclealkyl.

8. The optically active 5-hydroxyoxazolidine derivative as claimed in claim 7 wherein $R^1$ is methyl.

9. A process for preparing an optically active 5-hydroxyoxazolidine derivative wherein an optically active 5-oxazolidinone derivative represented by general formula (1):

(1)

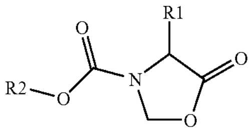

wherein $R^1$ represents an unprotected side chain or optionally protected side chain in a natural α-amino acid; wherein $R^2$ represents benzyl, tert-butyl, methyl, ethyl, isopropyl or 9-fluorenylmethyl, is reacted with an organometallic reagent represented by general formula (2):

$R^3$—M (2)

wherein $R^3$ represents optionally substituted aryl or optionally substituted heterocycle; M is one selected from the group consisting of Li, MgX, ZnX, $TiX_3$ and CuX; and X represents halogen, to provide an optically active 5-hydroxyoxazolidine derivative represented by general formula (3):

(3)

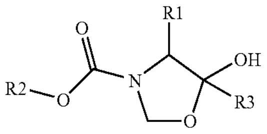

wherein $R^1$, $R^2$ and $R^3$ are as defined above.

10. The process for preparing an optically active 5-hydroxyoxazolidine derivative as claimed in claim 9 wherein $R^3$ is represented by general formula (7):

(7)

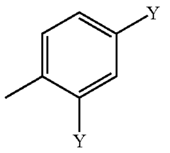

wherein Y represents halogen; or general formula (8):

(8)

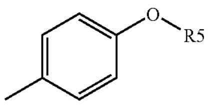

wherein $R^5$ represents hydrogen, optionally substituted alkyl, optionally substituted cycloalkyl, optionally substituted aralkyl, optionally substituted phenyl, optionally substituted heterocycle or optionally substituted heterocyclealkyl.

11. The process for preparing an optically active 5-hydroxyoxazolidine derivative as claimed in claim 10 wherein $R^1$ is methyl.

12. The process for preparing an optically active 5-hydroxyoxazolidine derivative as claimed in claim 9 wherein M in general formula (2) is MgX wherein X is as defined above.

13. An aminoketone derivative represented by (4a)

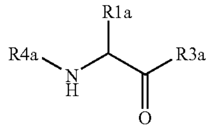

general formula (4a):

wherein $R^{1a}$ represents methyl; $R^{4a}$ represents hydrogen, benzyloxycarbonyl, tert-butoxycarbonyl or 9-fluorenylmethoxycarbonyl; $R^{3a}$ represents 4-benzyloxyphenyl, 4-methoxyphenyl, 2,4-difluorophenyl, 2,4-dichlorophenyl or 3-indolyl.

14. A process for preparing an aminoketone derivative wherein a 5-hydroxyoxazolidine derivative represented by general formula (3):

(3)

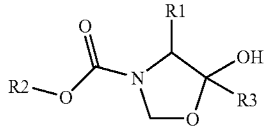

wherein $R^1$ represents an unprotected side chain or optionally protected side chain in a natural α-amino acid; $R^2$ represents optionally substituted alkyl, optionally substituted aryl or optionally substituted aralkyl; and $R^3$ represents optionally substituted aryl or optionally substituted heterocycle, is treated under acidic conditions to form an aminoketone derivative represented by general formula (4):

(4)

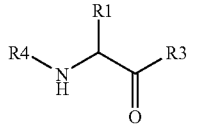

wherein $R^1$ and $R^3$ are as defined above; $R^4$ represents hydrogen or optionally substituted alkyloxycarbonyl, optionally substituted aryloxycarbonyl or optionally substituted aralkyloxycarbonyl as a protective group.

15. An optically active alcohol derivative represented by general formula (5a):

(5a)

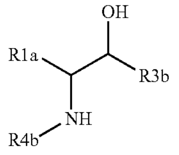

wherein $R^{1a}$ represents methyl; $R^{3b}$ represents 4-benzyloxyphenyl; $R^{4b}$ represents benzyloxycarbonyl; and configuration between the amino group and the hydroxy group is an erythro configuration.

16. A process for preparing an optically active aminoalcohol derivative wherein an optically active aminoketone derivative represented by general formula (4b):

(4b)

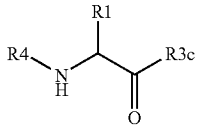

wherein $R^1$ represents an unprotected side chain or optionally protected side chain in a natural α-amino acid; $R^4$ represents hydrogen or optionally substituted alkyloxycarbonyl, optionally substituted aryloxycarbonyl or optionally substituted aralkyloxycarbonyl as a protective group; $R^{3c}$ is represented by general formula (8):

(8)

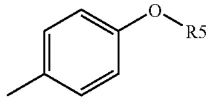

wherein, $R^5$ represents hydrogen, optionally substituted alkyl, optionally substituted cycloalkyl, optionally substituted aralkyl, optionally substituted phenyl, optionally substituted heterocycle or optionally substituted heterocyclealkyl, is catalytically hydrogenated with a metal catalyst, to stereoselectively form an optically active aminoalcohol derivative (5b)

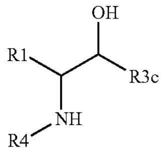

represented by general formula (5b):

wherein $R^1$, $R^{3c}$ and $R^4$ are as defined above;

provided that configuration of $R^1$ attached to the asymmetric carbon at 2-position and the substituent represented by a nitrogen atom in the optically active aminoketone derivative represented by general formula (4b) is not changed throughout these reactions and relative configuration between the amino group and the hydroxy group in the optically active aminoalcohol derivative represented by general formula (5b) is an erythro configuration.

17. A process for preparing an optically active aminoalcohol derivative wherein an optically active aminoketone derivative represented by general formula (4b):

(4b)

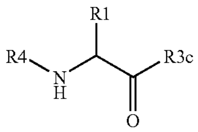

wherein $R^1$ represents an unprotected side chain or optionally protected side chain in a natural α-amino acid; $R^4$ represents hydrogen or optionally substituted alkyloxycarbonyl, optionally substituted aryloxycarbonyl or optionally substituted aralkyloxycarbonyl as a protective group; $R^{3c}$ is represented by general formula (8):

(8)

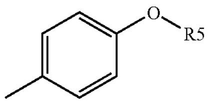

wherein, $R^5$ represents hydrogen, optionally substituted alkyl, optionally substituted cycloalkyl, optionally substituted aralkyl, optionally substituted phenyl, optionally substituted heterocycle or optionally substituted heterocyclealkyl, is catalytically hydrogenated with a metal catalyst, to stereoselectively form an optically active aminoalcohol represented by general formula (5b):

(5b)

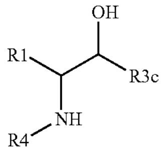

wherein $R^1$, $R^{3c}$ and $R^4$ are as defined above, and when $R^4$ is a protective group, the amino group in the product is deprotected to give an optically active aminoalcohol derivative represented by general formula (6a):

(6a)

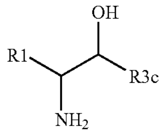

wherein $R^1$ and $R^{3c}$ are as defined above;

provided that configuration of $R^1$ attached to the asymmetric carbon at 2-position and the substituent represented by a nitrogen atom in the optically active aminoketone derivative represented by general formula (4b) is not changed throughout these reactions and relative configuration between the amino group and the hydroxy group in the optically active aminoalcohol derivative represented by general formula (6a) is an erythro configuration.

* * * * *

UNITED STATES PATENT AND TRADEMARK OFFICE

CERTIFICATE OF CORRECTION

PATENT NO. : 7,026,515 B2
APPLICATION NO. : 10/416185
DATED : April 11, 2006
INVENTOR(S) : Hidetoshi Tsunoda et al.

It is certified that error appears in the above-identified patent and that said Letters Patent is hereby corrected as shown below:

Please add the following:

Title page, item [30] Foreign Application Priority Data

Nov. 9, 2000 [JP] Japan ........................... 2000-341767
Nov. 9, 2000 [JP] Japan ........................... 2000-341906

Signed and Sealed this

Seventeenth Day of October, 2006

JON W. DUDAS
*Director of the United States Patent and Trademark Office*